US012622980B2

(12) United States Patent
Segura et al.

(10) Patent No.: US 12,622,980 B2
(45) Date of Patent: May 12, 2026

(54) NUCLEIC ACID LOADED FLOWABLE HYDROGELS AND COMPOSITIONS, SYSTEMS AND METHODS RELATED THERETO

(71) Applicant: DUKE UNIVERSITY, Durham, NC (US)

(72) Inventors: Tatiana Segura, Durham, NC (US); Evan Kurt, Durham, NC (US)

(73) Assignee: DUKE UNIVERSITY, Durham, NC (US)

( * ) Notice: Subject to any disclaimer, the term of this patent is extended or adjusted under 35 U.S.C. 154(b) by 1152 days.

(21) Appl. No.: 17/627,440

(22) PCT Filed: Jul. 15, 2020

(86) PCT No.: PCT/US2020/042131
§ 371 (c)(1),
(2) Date: Jan. 14, 2022

(87) PCT Pub. No.: WO2021/011648
PCT Pub. Date: Jan. 21, 2021

(65) Prior Publication Data
US 2022/0409746 A1     Dec. 29, 2022

Related U.S. Application Data

(60) Provisional application No. 62/874,074, filed on Jul. 15, 2019.

(51) Int. Cl.
| | |
|---|---|
| *C12N 15/85* | (2006.01) |
| *A61K 9/06* | (2006.01) |
| *A61K 9/19* | (2006.01) |
| *A61K 9/50* | (2006.01) |
| *A61K 47/59* | (2017.01) |
| *A61K 48/00* | (2006.01) |
| *A61L 27/54* | (2006.01) |
| *C12N 15/87* | (2006.01) |

(52) U.S. Cl.
CPC ........ *A61K 48/0041* (2013.01); *A61K 9/5036* (2013.01); *C12N 15/85* (2013.01); *C12N 2830/48* (2013.01)

(58) Field of Classification Search
None
See application file for complete search history.

(56) References Cited

U.S. PATENT DOCUMENTS

| | | |
|---|---|---|
| 2010/0260846 A1 | 10/2010 | McGonigle et al. |
| 2014/0227327 A1 | 8/2014 | Bencherif et al. |
| 2018/0021441 A1 | 1/2018 | Ma et al. |

FOREIGN PATENT DOCUMENTS

KR         101871241 B1 * 6/2018 ............. A61K 47/36

OTHER PUBLICATIONS

Kim YM, Park MR, and Soo-Chang Song, Injectable Polyplex Hydrogel for Localized and Long-Term Delivery of siRNA, ACS Nano 2012 6 (7), 5757-5766, DOI: 10.1021/nn300842a (Year: 2012).*

Li Y, Maciel D, Rodrigues J, Shi X, and Tomás H, Biodegradable Polymer Nanogels for Drug/Nucleic Acid Delivery, Chemical Reviews 2015 115 (16), 8564-8608, DOI: 10.1021/cr500131f (Year: 2015).*

Li J, Mooney DJ. Designing hydrogels for controlled drug delivery. Nat Rev Mater. Dec. 2016;1(12):16071. doi: 10.1038/natrevmats. 2016.71. Epub Oct. 18, 2016. PMID: 29657852; PMCID: PMC5898614. (Year: 2016).*

O'Rorke S et al: "Non-viral polyplexes: Scaffold mediated delivery for gene therapy", Progress in Polymer Science, Pergamon Press, Oxford, GB, vol. 35, No. 4, Apr. 1, 2010 (Apr. 1, 2010), pp. 441-458.

Jha, et al., "Hierarchically structured, hyaluronic acid-based hydrogel matrices via the covalent integration of microgels into macroscopic networks", Soft Matter, Jun. 15, 2010; 6(20); 5045-5055.

International Search Report and Written Opinion mailed Jan. 15, 2021 in corresponding International Patent Application No. PCT/US2020/042131.

Sideris et al., "Particle Hydrogels Based on Hyaluronic Acid Building Blocks", ACS Biomater, Sci. Eng. 2016, 2, 2034-2041.

Bonaguidi MA, et al. (2008). Noggin expands neural stem cells in the adult hippocampus. J. Neurosci. 28, 919-9204.

Carmichael ST. (2010). Targets for neural repair therapies after stroke. Stroke 41:S124-S126.

Griffin DR, et al. (2015). Accelerated wound healing by injectable microporous gel scaffolds assembled from annealed building blocks. Nat. Mater. 14:737-744.

Kaplitt MG, et al. (2007). Safety and tolerability of gene therapy with an adeno-associated virus (AAV) borne GAD gene for Parkinson's disease: an open label, phase I trial. Lancet 369:2097-2105.

Lei Y, et al. (2011). Hyaluronic acid and fibrin hydrogels with concentrated DNA/PEI polyplexes for local gene delivery. J. Control. Release. 153:255-261.

Nih LR, et al. (2017). Injection of Microporous Annealing Particle (MAP) Hydrogels in the Stroke Cavity Reduces Gliosis and Inflammation and Promotes NPC Migration to the Lesion. Adv. Mater. 29:1606471.

Petersen MA, et al. (2017). Fibrinogen Activates BMP Signaling in Oligodendrocyte Progenitor Cells and Inhibits Remyelination after Vascular Damage. Neuron. 96:1003-1012.e7.

Truong NF, et al. (2018) Sustained Transgene Expression via Hydrogel-Mediated Gene Transfer Results from Multiple Transfection Events. ACS Biomater. Sci. Eng. 4:981-987.

(Continued)

*Primary Examiner* — Anna Skibinsky
*Assistant Examiner* — Catherine L Mccormick
(74) *Attorney, Agent, or Firm* — Polsinelli PC

(57) ABSTRACT

The present disclosure provides, in part, nucleic acid loaded flowable hydrogels and compositions, systems and methods related thereto, to effectively deliver nucleic acids to cells that contact the flowable hydrogels.

20 Claims, 33 Drawing Sheets

Specification includes a Sequence Listing.

(56)            References Cited

OTHER PUBLICATIONS

Truong NF, et al. (2019). Microporous annealed particle hydrogel stiffness, void space size, and adhesion properties impact cell proliferation, cell spreading, and gene transfer. Acta Biomater. 94:160-172.

Truong NF, et al. (2018). Pathways Governing Polyethylenimine Polyplex Transfection in Microporous Annealed Particle Scaffolds. Bioconjug. Chem. 30(2):476-486.

U.S. Food and Drug Administration. (2018) FDA approves first-of-its kind targeted RNA-based therapy to treat a rare disease. at https://www.fda.gov/newsevents/newsroom/pressannouncements/ucm616518.htm.

U.S. Food and Drug Administration. (2017) FDA approves novel gene therapy to treat patients with a rare form of inherited vision loss. U.S. Dep. Heal. Hum. Serv. 4-7.

Wang HX, et al. (2017) W. CRISPR/Cas9-Based Genome Editing for Disease Modeling and Therapy: Challenges and Opportunities for Nonviral Delivery. Chem. Rev. 117:9874-9906.

* cited by examiner

HA coatings

Unmodified HA

HA-Ac

HA-Norb

●— PEI-only, fresh

▲— HA-NB coated, freh

■— PEI-only, CnE

▼— NA-NB coated, CnE

FIG. 9(b)

Alginate/PEI (w/w)

NUCLEIC ACID LOADED FLOWABLE HYDROGELS AND COMPOSITIONS, SYSTEMS AND METHODS RELATED THERETO

CROSS-REFERENCE TO RELATED APPLICATIONS

This application is a national phase application of International Application No. PCT/US2020/042131 filed Jul. 15, 2020, which claims the benefit under 35 U.S.C. § 119 of the U.S. Provisional Patent Application No. 62/874,074, filed Jul. 15, 2019, which applications are hereby incorporated by reference in their entirety.

STATEMENT REGARDING FEDERALLY SPONSORED RESEARCH OR DEVELOPMENT

This invention was made with Government support under Federal Grant No. R01NS094599 awarded by the National Institutes of Health. The Federal Government has certain rights to this invention.

INCORPORATION BY REFERENCE OF SEQUENCE LISTING PROVIDED ELECTRONICALLY

This application is being filed electronically via EFS-Web and includes an electronically submitted Sequence Listing in .txt format. The .txt file contains a sequence listing titled "20-1056-WO_SEQ-LISTING_ST25.txt" created on Jul. 19, 2022 and is 2 kilobytes in size. The Sequence Listing contained in this .txt file is part of the specification and is hereby incorporated by reference herein in its entirety.

FIELD

The present disclosure relates to nucleic acid loaded flowable hydrogels and compositions, systems and methods related thereto, to effectively deliver nucleic acids to cells that contact or infiltrate the flowable hydrogels.

BACKGROUND

Nucleic acid delivery has the potential to up-regulate and/or down-regulate any gene known to have bioactivity in humans to impact human health, introduce transgenes encoding recombinant proteins not otherwise present in a cell, or that encode the native bioactive signal, and more. Nucleic acid delivery has applications ranging from tissue engineering to vaccine development to infectious disease. This goal has driven the field of gene therapy for over two decades. A key goal of nucleic acid delivery is to achieve effective delivery into human cells. Most approaches to deliver nucleic material involve the systemic intravenous delivery of condensed nucleic acid (e.g., within a virus or a synthetic particle). However, this approach suffers from immune recognition, accumulation in first pass organs, and rapid clearance. This includes the FDA approved gene therapies onasemnogene abeparvovec (AAV injected intravenously) and patisiran (siRNA lipoplex delivered intravenously). To circumvent these limitations, local delivery approaches that inject and retain the nucleic acid cargo at desired locations are beneficial. For example, the FDA approved gene therapy voretigene neparvovec delivers AAV directly into the eye by subretinal injection, bypassing immune recognition, first pass organ accumulation, and rapid clearance. While the eye is an enclosed environment and has low risk for gene therapies diffusing to the rest of the body, this is not the case for most organs, which requires an alternative delivery method.

SUMMARY

The Summary is provided to introduce a selection of concepts that are further described below in the Detailed Description. This Summary is not intended to identify key or essential features of the claimed subject matter, nor is it intended to be used as an aid in limiting the scope of the claimed subject matter.

Accordingly, one aspect of the present disclosure provides a scaffold comprising hydrogel particles, wherein the particles comprise one or more polyplexes, which polyplexes comprise one or more copies of one or more nucleic acids and one or more nucleic acid complexing agents. In some embodiments, one or more particles originates from a bulk hydrogel, and in some embodiments, one or more particles can also be discretely polymerized, and mixtures thereof. In some embodiments, polyplexes are substantially evenly distributed throughout particles that originate from a bulk hydrogel, and in some embodiments, at least one particle comprises an irregular shape. In some embodiments, particles comprise regular and irregular shapes.

In some embodiments, the scaffold comprises one or more particles devoid of nucleic acid, nucleic acid complexing agent and/or polyplexes, with the proviso that not all particles are devoid of nucleic acid, nucleic acid complexing agent and/or polyplexes.

In some embodiments, the scaffold comprises particles of two or more types.

In some embodiments, particles comprise an irregular shape with an average surface area that can range from about $100 \ \mu m^2$ and $1000000 \ \mu m^2$, as well as other size ranges. In some embodiments, the irregularly shaped particles comprise shred particles. In some embodiments, two or more particles are annealed together, wherein annealed together comprises covalent, electrostatic, hydrophobic, mechanical and transamination annealing.

In some embodiments, nucleic acids comprise DNA and RNA, and in some embodiments, the nucleic acid complexing agent comprises a cationic polymer, cationic peptide, cationic lipid, or mixtures. In some embodiments, the nucleic acid and the nucleic acid complexing agent are mixed at a N/P ratio, which ratio comprises between about 1 and 100 and other relevant ratios.

In some embodiments, the polyplexes further comprise a coating layer, which can comprise one or more coating layer agents, which, in some embodiments, comprise one or more biocompatible polymers, one or more mineral salts, and mixtures thereof.

In some embodiments, the polymer is bound to one or more peptides comprising at least three consecutive amino acids from an extracellular matrix protein, which peptide, in some embodiments, comprises an integrin binding peptide, and in some embodiments, comprises an RGD peptide. In some embodiments, the polymer is bound to one or more peptides comprising K-peptide and Q-peptide.

In some embodiments, the one or more nucleic acid complexing agents and one or more coating layer agents are mixed at a coating/complexing ratio, which ratio, in some embodiments, comprises between about 0.1 and 100, as well as other ratios In some embodiments, the polyplexes comprise lyophilized polyplexes, and in some embodiments, further comprise a cryoprotectant.

In some embodiments, the concentration of the nucleic acid is at least about 0.1 mg/ml, to about 20 mg/ml, and additional concentrations.

Another aspect of the disclosure provides a structure for localized and controlled release of nucleic acids, comprising a scaffold comprising hydrogel particles, wherein the particles comprise one or more polyplexes, which polyplexes comprise one or more copies of one or more nucleic acids and one or more nucleic acid complexing agents, wherein the one or more nucleic acids is present at a total concentration of at least about 0.1 mg/ml, and further wherein the scaffold is characterized in that, when the structure is placed in contact with cells of a subject so that the scaffold contacts the cells, the nucleic acid is released with a profile characterized by one or more of (a) a burst-free release; (b) a sustained release; and (c) exhibiting in vitro and/or in vivo biological effectiveness.

In some embodiments, scaffold comprises one or more particles that is devoid of nucleic acids, nucleic acid complexing agents and/or polyplexes, with the proviso that not all particles are devoid of nucleic acid and nucleic acid complexing agent. In some embodiments, the concentration of the nucleic acid is at least about 0.1 mg/ml, to about 20 mg/ml, and additional concentrations.

In some embodiments, the burst-free release is characterized by releasing less than about 5%, about 10%, about 15%, about 20%, about 25%, about 30%, about 35%, about 40%, about 45% or about 50% of the nucleic acid agent in the first 24 hours after placement on or in the subject. In some embodiments, the burst-free release is characterized by nucleic acids release originating from only those particles in contact with cells of a subject. In some embodiments, the sustained release is characterized by the nucleic acid being released from the scaffold over an extended period of time up to about one year.

In some embodiments, one or more particles originates from a bulk hydrogel, and in some embodiments, one or more particles can also be discretely polymerized, and mixtures thereof. In some embodiments, polyplexes are substantially evenly distributed throughout particles that originate from a bulk hydrogel, and in some embodiments, at least one particle comprises an irregular shape. In some embodiments, particles comprise regular and irregular shapes.

In some embodiments, the scaffold comprises hydrogel particles of two or more types.

In some embodiments, the scaffold comprises the particles comprise an irregular shape with an average surface area that can range from about 100 μm² and 1000000 μm², as well as other size ranges. In some embodiments, the irregularly shaped particles comprise shred particles. In some embodiments, two or more particles are annealed together, wherein annealed together comprises covalent, electrostatic, hydrophobic and mechanical annealing.

In some embodiments, nucleic acids comprise DNA and RNA, and in some embodiments, the nucleic acid complexing agent comprises a cationic polymer, cationic peptide, cationic lipid, or mixtures. In some embodiments, the nucleic acid and the nucleic acid complexing agent are mixed at a N/P ratio, which ratio comprises between about 1 and 100 and other relevant ratios.

In some embodiments, the polyplexes further comprise a coating layer, which can comprise one or more coating layer agents, which, in some embodiments, comprise one or more biocompatible polymers, one or more mineral salts, and mixtures thereof.

In some embodiments, the polymer is bound to one or more peptides comprising at least three consecutive amino acids from an extracellular matrix protein, which peptide, in some embodiments, comprises an integrin binding peptide, and in some embodiments, comprises an RGD peptide.

In some embodiments, the one or more nucleic acid complexing agents and one or more coating layer agents are mixed at a coating/complexing ratio, which ratio, in some embodiments, comprises between about 0.1 and 100, as well as other ratios In some embodiments, the polyplexes comprise lyophilized polyplexes, and in some embodiments, further comprise a cryoprotectant.

In some embodiments, the concentration of the nucleic acid is at least about 0.1 mg/ml, to about 20 mg/ml, and additional concentrations.

Another aspect of the disclosure provides a pharmaceutical composition of hydrogel particles comprising one or more polyplexes, which polyplexes encapsulate a therapeutically effective amount of at least one bioactive nucleic acid.

In some embodiments, the pharmaceutical composition comprises one or more particles that is devoid of bioactive nucleic acids and nucleic acid complexing agents, with the proviso that not all particles are devoid of bioactive nucleic acid and nucleic acid complexing agent.

In some embodiments, the pharmaceutical composition comprises hydrogel particles of two or more types.

In some embodiments, one or more particles originates from a bulk hydrogel, and in some embodiments, one or more particles can also be discretely polymerized, and mixtures thereof. In some embodiments, polyplexes are substantially evenly distributed throughout particles that originate from a bulk hydrogel, and in some embodiments, at least one particle comprises an irregular shape. In some embodiments, particles comprise regular and irregular shapes.

In some embodiments, the particles comprise an irregular shape with an average surface area that can range from about 100 μm² and 1000000 μm², as well as other size ranges. In some embodiments, the irregularly shaped particles comprise shred particles. In some embodiments, two or more particles are annealed together, wherein annealed together comprises covalent, electrostatic, hydrophobic and mechanical annealing.

In some embodiments, nucleic acids comprise DNA and RNA, and in some embodiments, the nucleic acid complexing agent comprises a cationic polymer, cationic peptide, cationic lipid, or mixtures. In some embodiments, the nucleic acid and the nucleic acid complexing agent are mixed at a N/P ratio, which ratio comprises between about 1 and 100 and other relevant ratios.

In some embodiments, the polyplexes further comprise a coating layer, which can comprise one or more coating layer agents, which, in some embodiments, comprise one or more biocompatible polymers, one or more mineral salts, and mixtures thereof.

In some embodiments, the polymer is bound to one or more peptides comprising at least three consecutive amino acids from an extracellular matrix protein, which peptide, in some embodiments, comprises an integrin binding peptide, and in some embodiments, comprises an RGD peptide.

In some embodiments, the one or more nucleic acid complexing agents and one or more coating layer agents are mixed at a coating/complexing ratio, which ratio, in some embodiments, comprises between about 0.1 and 100, as well as other ratios In some embodiments, the polyplexes comprise lyophilized polyplexes, and in some embodiments, further comprise a cryoprotectant.

In some embodiments, the concentration of the nucleic acid is at least about 0.1 mg/ml, to about 20 mg/ml, and additional concentrations.

Another aspect of the disclosure provides a method of nucleic acid delivery to a cell, comprising contacting a cell with two or more hydrogel particles, wherein the particles comprise one or more polyplexes, which polyplexes comprise one or more copies of one or more nucleic acids and one or more nucleic acid complexing agents.

In some embodiments, one or more particles originates from a bulk hydrogel, and in some embodiments, one or more particles can also be discretely polymerized, and mixtures thereof. In some embodiments, polyplexes are substantially evenly distributed throughout particles that originate from a bulk hydrogel, and in some embodiments, at least one particle comprises an irregular shape. In some embodiments, particles comprise regular and irregular shapes.

In some embodiments, the scaffold comprises one or more particles devoid of nucleic acid, nucleic acid complexing agent and/or polyplexes, with the proviso that not all particles are devoid of nucleic acid, nucleic acid complexing agent and/or polyplexes.

In some embodiments, the scaffold comprises particles of two or more types.

In some embodiments, the particles comprise an irregular shape with an average surface area that can range from about 100 $\mu$m$^2$ and 1000000 $\mu$m$^2$, as well as other size ranges. In some embodiments, the irregularly shaped particles comprise shred particles. In some embodiments, two or more particles are annealed together, wherein annealed together comprises covalent, electrostatic, hydrophobic and mechanical annealing. In some embodiments, the one or more hydrogel particles is annealed together after contacting the cell.

In some embodiments, nucleic acids comprise DNA and RNA, and in some embodiments, the nucleic acid complexing agent comprises a cationic polymer, cationic peptide, cationic lipid, or mixtures. In some embodiments, the nucleic acid and the nucleic acid complexing agent are mixed at a N/P ratio, which ratio comprises between about 1 and 100 and other relevant ratios.

In some embodiments, the polyplexes further comprise a coating layer, which can comprise one or more coating layer agents, which, in some embodiments, comprise one or more biocompatible polymers, one or more mineral salts, and mixtures thereof.

In some embodiments, the polymer is bound to one or more peptides comprising at least three consecutive amino acids from an extracellular matrix protein, which peptide, in some embodiments, comprises an integrin binding peptide, and in some embodiments, comprises an RGD peptide.

In some embodiments, the one or more nucleic acid complexing agents and one or more coating layer agents are mixed at a coating/complexing ratio, which ratio, in some embodiments, comprises between about 0.1 and 100, as well as other ratios In some embodiments, the polyplexes comprise lyophilized polyplexes, and in some embodiments, further comprise a cryoprotectant.

In some embodiments, the concentration of the nucleic acid is at least about 0.1 mg/ml, to about 20 mg/ml, and additional concentrations.

In some embodiments of the methods of this aspect of the disclosure, contacting a cell comprises all relevant methods of administration, e.g., topically, intravascularly, intravenously, injection, infusion, orally, enterally, rectally, pulmonarily, inhalation, nasally, topically, transdermally, buccally, sublingually, intravesically, intravitreally, intraperitoneally, vaginally, brain, intra-cerebroventricularly, intra-cerebrally, intrasynovially, intracutaneously, intraarticularly, intraarterially, intrathecally, perispinally, intra-spinally, parenterally, subcutaneously, intrasternally, intralesionally, intramuscularly, intravenously, intradermally, transmucosally, sublingually, and the like.

Another aspect of the disclosure provides a method for making a scaffold according to some aspects and embodiments of the disclosure, comprising: (i.) combining the nucleic acid and the nucleic acid complexing agent at a N/P ratio to form one or more polyplexes; (ii.) combining the polyplexes with one or more coating layer agents to form a coating layer on the polyplexes; (iii.) mixing polyplexes comprising a coating layer with a hydrogel; (iv.) crosslinking the hydrogel-polyplex mixture to form a bulk hydrogel; (v.) fractionating the crosslinked hydrogel into two or more pieces to make hydrogel particles; and (vi.) combining the hydrogel particles to make a scaffold. In some embodiments, steps iii. and iv. occur simultaneously.

In some embodiments, fractionating comprises passing the crosslinked hydrogel through a sieve or mesh with an average pore size, which sieve or mesh in some embodiments comprises a cell strainer. In some embodiments, the average pore size comprises between about 1 $\mu$m and 1000 $\mu$m, as well as other suitable pore sizes.

In some embodiments, one or more particles can also be discretely polymerized, and mixtures thereof. In some embodiments, polyplexes are substantially evenly distributed throughout particles that originate from a bulk hydrogel, and in some embodiments, at least one particle comprises an irregular shape. In some embodiments, particles comprise regular and irregular shapes.

In some embodiments of the method the particles comprise two or more types. In some embodiments, the method further comprises combining one or more hydrogel particles devoid of nucleic acid, nucleic acid complexing agent, and/or polyplexes with the hydrogel particles of step vi. to make a scaffold. In some embodiments, the method further comprises combining one or more hydrogel particles of a different type from those prepared according to this aspect of the disclosure with the hydrogel particles of step vi. to make a scaffold. In some embodiments, the different type comprises discretely polymerized particles. In some embodiments, the method further comprises combining a first batch of one or more hydrogel particles prepared according to this aspect of the disclosure with a second batch of one or more hydrogel particles also prepared according to this aspect of the disclosure, with the proviso that at least one of nucleic acid, nucleic acid complexing agent, coating layer agents, or hydrogel, is different between batch one and batch two.

In some embodiments, particles comprise an irregular shape with an average surface area that can range from about 100 $\mu$m$^2$ and 1000000 $\mu$m$^2$, as well as other size ranges. In some embodiments, the irregularly shaped particles comprise shred particles. In some embodiments, two or more particles are annealed together, wherein annealed together comprises covalent, electrostatic, hydrophobic and mechanical annealing.

In some embodiments, nucleic acids comprise DNA and RNA, and in some embodiments, the nucleic acid complexing agent comprises a cationic polymer, cationic peptide, cationic lipid, or mixtures. In some embodiments, the nucleic acid and the nucleic acid complexing agent are mixed at a N/P ratio, which ratio comprises between about 1 and 100 and other relevant ratios.

In some embodiments, the polyplexes further comprise a coating layer, which can comprise one or more coating layer agents, which, in some embodiments, comprise one or more biocompatible polymers, one or more mineral salts, and mixtures thereof.

In some embodiments, the polymer is bound to one or more peptides comprising at least three consecutive amino acids from an extracellular matrix protein, which peptide, in some embodiments, comprises an integrin binding peptide, and in some embodiments, comprises an RGD peptide.

In some embodiments, the one or more nucleic acid complexing agents and one or more coating layer agents are mixed at a coating/complexing ratio, which ratio, in some embodiments, comprises between about 0.1 and 100, as well as other ratios In some embodiments, the polyplexes comprise lyophilized polyplexes, and in some embodiments, further comprise a cryoprotectant.

In some embodiments, the concentration of the nucleic acid is at least about 0.1 mg/ml, to about 20 mg/ml, and additional concentrations.

The compositions, systems, and methods provided herein will help improve non-viral gene delivery methods from hydrogel scaffolds to enhance transfection and tissue repair in vivo.

BRIEF DESCRIPTION OF THE DRAWINGS

The foregoing aspects and other features of the disclosure are explained in the following description, taken in connection with the accompanying drawings, herein:

FIG. 4 shows aggregation stability of DNA/PEI polyplexes (N/P of 20, 1 μg/100 μL) after lyophilization and resuspension in 150 mM NaCl. The data is presented as a heat map of nanoparticle diameter (DLS data) over time as modeled using factorial DOE. The y-axis represents different N/P (PEI/DNA ratios) and the x-axis are different coating ratios with HA-NB. Dark represents aggregation and light shades represent stable particles. The dotted line represents the data presented in FIG. 3. The box represents the region that was found to result in the most stable particles.

FIG. 7 shows FLIP scaffold properties.

FIG. 10 shows annealing and mechanical properties of FLIP scaffolds loaded with L-PEI plasmid DNA containing lyophilized polyplexes ("LyPP").

FIG. 11 shows Loaded nucleic acid polyplex distribution in bulk HA-Ac hydrogel precursor solution. Bulk gels were prepared as described, with DNA stained and imaged on confocal microscopy.

FIG. 14 shows Retention of lyophilized polyplexes within FLIP scaffolds.

FIG. 16 shows FLIP transfection comparison for the presence of sucrose.

in which different gel layers containing transgenes for either GFP and mCherry are used in 3D culture, and cells seeded within the scaffold. Transgene expression was assessed with flow cytometry on degraded gels for cell extraction, showing highly specific gene expression for only the given reporter in each layer (denoted in the microscopy image of reporter-expressing cells by the percentage).

Figure 20:
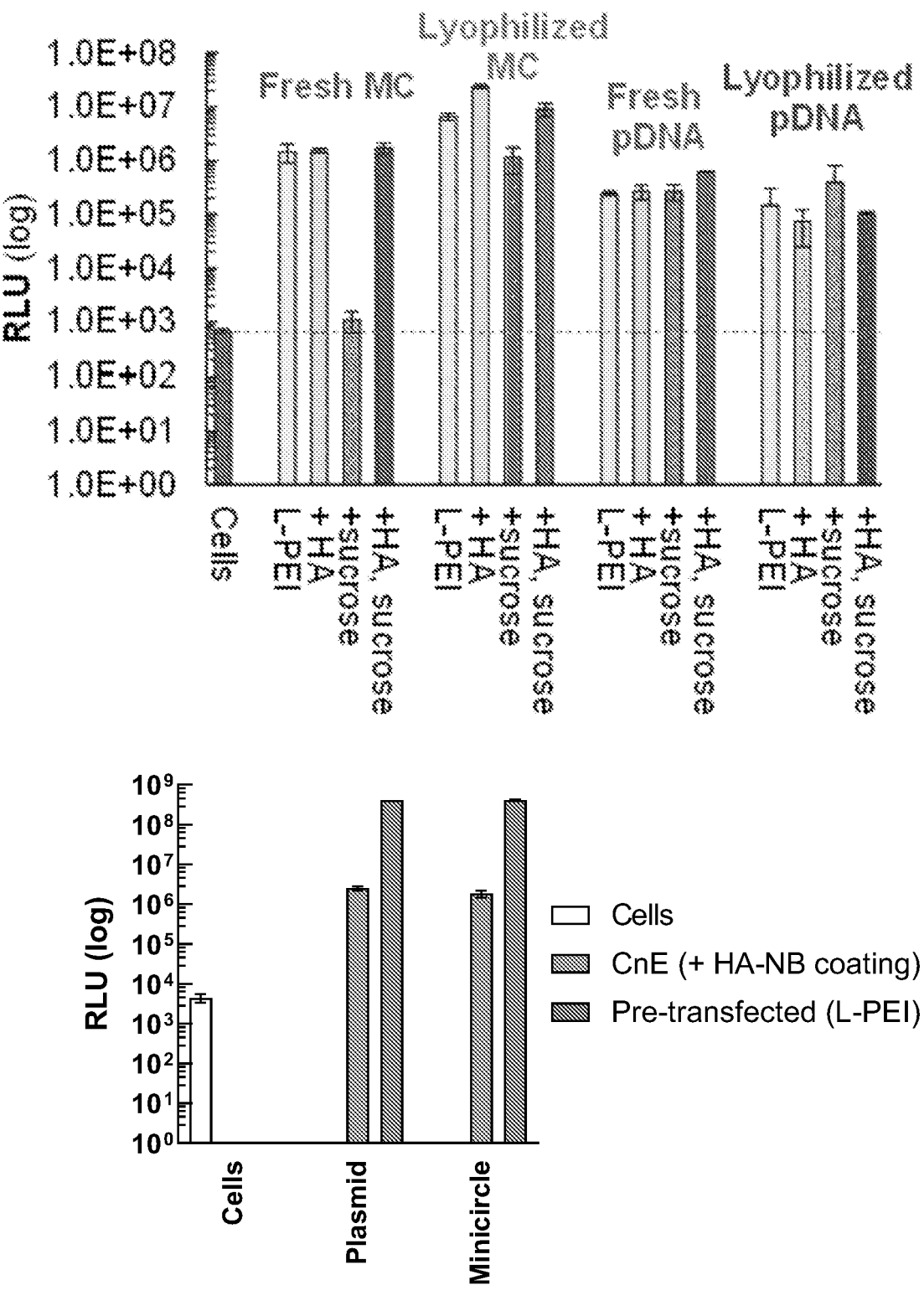

FIG. 20 shows that DNA minicircle transfection is enhanced by HA coating of PEI-DNA polyplexes in 2D and 3D culture. (Top panel) 2D comparison of freshly prepared polyplexes, with and without HA coating and sucrose, to lyophilized polyplexes with sucrose and HA coating. Minicircles (MC) were compared to their original plasmid vector as a control for all conditions. HA coating and lyophilization enhanced minicircle transfection relative to fresh polyplexes, with sucrose inclusion not required to benefit from the HA coating, and in addition to giving higher transgene expression than all plasmid conditions. (Bottom panel) 3D FLIP transfection of HA coated polyplexes, from plasmid and minicircle DNA. HA coating gave similar levels between both vectors, with no loss of transfection for minicircle DNA.

DETAILED DESCRIPTION OF THE INVENTION

For the purposes of promoting an understanding of the principles of the present disclosure, reference will now be made to preferred embodiments and specific language will be used to describe the same. It will nevertheless be understood that no limitation of the scope of the disclosure is thereby intended, such alteration and further modifications of the disclosure as illustrated herein, being contemplated as would normally occur to one skilled in the art to which the disclosure relates.

Articles "a" and "an" are used herein to refer to one or to more than one (i.e. at least one) of the grammatical object of the article. By way of example, "an element" means at least one element and can include more than one element.

"About" is used to provide flexibility to a numerical range endpoint by providing that a given value may be "slightly above" or "slightly below" the endpoint without affecting the desired result.

The use herein of the terms "including," "comprising," or "having," and variations thereof, is meant to encompass the elements listed thereafter and equivalents thereof as well as additional elements. As used herein, "and/or" refers to and encompasses any and all possible combinations of one or more of the associated listed items, as well as the lack of combinations where interpreted in the alternative ("or").

As used herein, the transitional phrase "consisting essentially of" (and grammatical variants) is to be interpreted as encompassing the recited materials or steps "and those that do not materially affect the basic and novel characteristic(s)" of the claimed invention. Thus, the term "consisting essentially of" as used herein should not be interpreted as equivalent to "comprising."

Moreover, the present disclosure also contemplates that in some embodiments, any feature or combination of features set forth herein can be excluded or omitted. To illustrate, if the specification states that a complex comprises components A, B and C, it is specifically intended that any of A, B or C, or a combination thereof, can be omitted and disclaimed singularly or in any combination.

Recitation of ranges of values herein are merely intended to serve as a shorthand method of referring individually to each separate value falling within the range, unless otherwise-Indicated herein, and each separate value is incorporated into the specification as if it were individually recited herein. For example, if a concentration range is stated as 1% to 50%, it is intended that values such as 2% to 40%, 10% to 30%, or 1% to 3%, etc., are expressly enumerated in this specification. These are only examples of what is specifically intended, and all possible combinations of numerical values between and including the lowest value and the highest value enumerated are to be considered to be expressly stated in this disclosure.

As used herein, "treatment," "therapy" and/or "therapy regimen" refer to the clinical intervention made in response to a disease, disorder or physiological condition manifested by a patient or to which a patient may be susceptible. The aim of treatment includes the alleviation or prevention of symptoms, slowing or stopping the progression or worsening of a disease, disorder, or condition and/or the remission of the disease, disorder or condition.

The term "effective amount" or "therapeutically effective amount" refers to an amount sufficient to effect beneficial or desirable biological and/or clinical results.

As used herein, the term "subject" and "patient" are used interchangeably herein and refer to both human and nonhuman animals. The term "nonhuman animals" of the disclosure includes all vertebrates, e.g., mammals and non-mammals, such as nonhuman primates, sheep, dog, cat, horse, cow, chickens, amphibians, reptiles, and the like.

As used herein, the term "nucleic acid" refers to isolated, purified, natural, recombinant, synthetic deoxyribonucleotides or ribonucleotides and polymers thereof in either single- or double-stranded form, composed of monomers (nucleotides) containing a sugar, phosphate and a base that is either a purine or pyrimidine. Unless specifically limited, the term encompasses nucleic acids containing known analogs of natural nucleotides that have similar binding properties as the reference nucleic acid and are metabolized in a manner similar to naturally occurring nucleotides. Unless otherwise indicated, a particular nucleic acid sequence also implicitly encompasses conservatively modified variants thereof (e.g., degenerate codon substitutions) and complementary sequences as well as the reference sequence explicitly indicated.

The term "oligonucleotide" as used herein is defined as a molecule comprised of two or more deoxyribonucleotides or ribonucleotides, preferably more than three, and usually more than ten. There is no precise upper limit on the size of an oligonucleotide. However, in general, an oligonucleotide is shorter than about 250 nucleotides, preferably shorter than about 200 nucleotides and more preferably shorter than about 100 nucleotides. The exact size will depend on many factors, which in turn depends on the ultimate function or use of the oligonucleotide. The oligonucleotide may be generated in any manner, including chemical synthesis, DNA replication, reverse transcription, or a combination thereof.

As used herein, the term "bioactive nucleic acid" refers to a nucleic acid that may bind or otherwise interact with a target gene or a nucleotide sequence comprising the same in vitro or in vivo, thereby activating or inhibiting the characteristic function of the target gene (e.g., transcript expression or protein expression) or regulating splicing of pre-mRNA (e.g., exon skipping), or any other means of activation, inhibition or other regulation of activity or function of a cellular target.

As used herein, the term "burst free release" refers to the characteristics of nucleic acid release from hydrogel particles upon contact with and invasion by one or more cells.

Nucleic acids of the disclosure are not released with a "burst" as air from a balloon upon encountering a needle. Rather, nucleic acid is released slowly as cells infiltrate the scaffold or plurality of hydrogel particles. Not to be limited by theory, but cells invading a scaffold can secrete matrix metalloproteinases, which degrade/remodel the scaffold and release the encapsulated nucleic acid nanoparticles locally where the cells are in contact with and/or invading the scaffold.

As used herein, the term "FLIP" scaffold refers to scaffolds comprising Flowable Linked Irregular Particles.

As used herein, the term "sHMP" refers to shredded hydrogel microparticles, or particles prepared by physical separation of larger bulk hydrogels as described herein.

As used herein, the term "shred particles" refers to the particles created by passing a crosslinked hydrogel through a sieve or mesh (e.g., a cell strainer) with an average pore size smaller than the hydrogel. The crosslinked hydrogel is fractionated into pieces sized according to the average pore size of the sieve or mesh. Exemplary average pore sizes can be about 1000 μm, about 750 μm, about 500 μm, about 400 μm, about 300 μm, about 200 μm, about 150 μm, about 100 μm, about 85 μm, about 70 μm, about 60 μm, about 50 μm, about 40 μm, about 30 μm, about 20 μm, about 10 μm, or about 1 μm.

As used herein, the term "substantially evenly distributed" refers to no 20% portion of a bulk gel being devoid of at least one polyplex.

As used herein, the term "nucleic acid complexing agent" refers to a molecule, compound or chemical moiety that interacts with one or more nucleic acids to enable packaging in hydrogel particles with reduced, minimized or prevented aggregation or other characteristics detrimental to packaging and delivery of such nucleic acid to a cell.

As used herein, the term "N/P ratio" or "N/P" refers to the ratio of positively-chargeable polymer amine (N=nitrogen) groups to negatively-charged nucleic acid phosphate (P) groups, and is a way to define mixture ratios for polymer-based nucleic acid delivery vehicles.

As used herein, the term "coating/complexing ratio" refers to the weight/weight ratio of coating layer agent to nucleic acid complexing agent, and is another way, according to this disclosure, to define mixture ratios for polymer-based nucleic acid delivery vehicles.

As used herein, the term "polyplex" refers to a complex of a polymer and nucleic acid designed to protect and/or assist in the delivery of the nucleic acid when used in a nucleic acid therapy.

As used herein, "nucleic acid therapy" refers to the transfer or insertion of nucleic acid molecules into certain cells, which may be referred to as target cells, to produce specific gene products that are involved in correcting or modulating diseases or disorders and/or promote beneficial biological processes. The nucleic acid is introduced into the selected target cells in a manner such that the nucleic acid is expressed and a product encoded thereby is produced. Alternatively, the nucleic acid may in some manner mediate the expression of nucleic acid that encodes a therapeutic product. This product may be a therapeutic compound, which is produced in therapeutically effective amounts or at a therapeutically useful time. It may also encode a product, such as a peptide or RNA, that in some manner mediates, directly or indirectly, expression of a therapeutic product. Expression of the nucleic acid by the target cells within an organism afflicted with a disease or disorder thereby provides a way to modulate the disease or disorder or beneficial biological processes. The nucleic acid encoding the therapeutic product may be modified prior to introduction into the target cell in order to enhance or otherwise alter the product or expression thereof. Nucleic acid therapy also refers to administration or in situ generation of a nucleic acid or a derivative thereof which specifically hybridizes (e.g., binds) under cellular conditions with the cellular mRNA and/or genomic DNA encoding one of a target polypeptides so as to inhibit production of that protein, e.g., by inhibiting transcription and/or translation. The binding may be by conventional base pair complementarity, or, for example, in the case of binding to DNA duplexes, through specific interactions in the major groove of the double helix.

For use in nucleic acid therapy, cells can be transfected in vitro via methods of the disclosure, followed by introduction of the transfected cells into the body of a subject. This is often referred to as ex vivo nucleic acid therapy. Alternatively, the cells can be transfected directly in vivo within the body of a subject.

As used herein, "heterologous" or "foreign" with reference to nucleic acids, DNA and RNA are used interchangeably and refer to nucleic acid, DNA or RNA that does not occur naturally as part of the genome in which it is present or which is found in a location(s) or in an amount in the genome that differs from that in which it occurs in nature. It is nucleic acid that has been exogenously introduced into the cell. Thus, heterologous nucleic acid is nucleic acid not normally found in the host genome in an identical context. Examples of heterologous nucleic acids include, but are not limited to, DNA that encodes a gene product or gene product(s) of interest, introduced for purposes of gene therapy or for production of an encoded protein. Other examples of heterologous DNA include, but are not limited to, DNA that encodes a selectable marker, DNA that encodes therapeutically effective substances, such as anti-cancer agents, enzymes and hormones, and DNA that encodes other types of proteins, such as antibodies.

As used herein, "expression" refers to the process by which nucleic acid, e.g., DNA, is transcribed into mRNA and translated into peptides, polypeptides, or proteins. If the nucleic acid is derived from genomic DNA, expression may, if an appropriate eukaryotic host cell or organism is selected, include splicing of the mRNA.

As used herein, "transformation" or "transfection" refers to the process by which nucleic acids are introduced into cells. Transfection refers to the taking up of exogenous nucleic acid, by a host cell whether or not any coding sequences are in fact expressed. Methods and compositions of the disclosure are effective for transformation or transfection. Successful transfection is generally recognized by detection of the presence of the heterologous nucleic acid within the transfected cell, such as, for example, any visualization of the heterologous nucleic acid or any indication of the operation of a such nucleic acid within the host cell.

Unless otherwise defined, all technical terms used herein have the same meaning as commonly understood by one of ordinary skill in the art to which this disclosure belongs.

One aspect of the present disclosure provides a scaffold comprising hydrogel particles, wherein the particles comprise one or more polyplexes, which polyplexes comprise one or more copies of one or more nucleic acids and one or more nucleic acid complexing agents. In some embodiments, one or more particles originates from a bulk hydrogel. For example, one or more polyplexes can be incorporated, poured, cast, polymerized into, and the like, in, into, or within a bulk hydrogel, which bulk hydrogel comprises a size larger than a desired size for hydrogel particles to make a scaffold of the disclosure. Such bulk hydrogels can be fractionated into two or more pieces until a desired hydrogel particle size is achieved. In some embodiments, one or more particles can also be discretely polymerized. For example, one or more polyplexes can be incorporated, poured, cast, polymerized into, and the like, in, into, or within a hydrogel, which hydrogel comprises a desired size upon formation. Further fractionation is not necessary. In some embodiments, one or more particles originate from a bulk hydrogel and one or more particles is discretely polymerized. In some embodiments, polyplexes are substantially evenly distributed throughout particles that originate from a bulk hydrogel. In some embodiments, at least one particle comprises an irregular shape. For example, dividing a bulk hydrogel into two or more pieces may introduce irregular lines of separation between pieces (i.e., "jagged edges") and irregular shapes. Discrete polymerization of particles typically does not form such jagged edges and irregular shapes. In some embodiments, particles comprise both regular and irregular shapes.

In some embodiments, the scaffold comprises one or more particles devoid of nucleic acid, nucleic acid complexing agent and/or polyplexes, with the proviso that not all particles are devoid of nucleic acid, nucleic acid complexing agent and/or polyplexes. For particles that originate from a bulk hydrogel and for particles that are discretely polymerized, some particles may comprise hydrogel devoid ("empty particles") of nucleic acid, nucleic acid complexing agent and/or polyplexes depending on the concentration of polyplexes used and relative size of end particles. Such particles are contemplated and useful for use along with particles that comprise one or more polyplexes ("loaded particles"). In some embodiments, empty and loaded particles can be organized, layered, placed and otherwise arranged in 2D and 3D space to accomplish different goals. Particles with different hydrogel compositions, different polyplex compositions (both nucleic acids and nucleic acid complexing agent(s)), empty and loaded for each case, discretely polymerized, originating from a bulk hydrogel or both, can be specifically arranged. For example, different (or not) nucleic acids could be delivered to different (or not) cells in different (or not) regions of a scaffold with different (or not) efficiencies based on the compositions of each component of the scaffold of the disclosure. Thus, in some embodiments, the scaffold comprises particles of two or more types.

In some embodiments, the one or more particles that comprise an irregular shape comprise an average surface area that can range from between about 100 $\mu m^2$ and 1000000 $\mu m^2$, or between about 500 $\mu m^2$ and 500000 $\mu m^2$, or between about 1000 $\mu m^2$ and 250000 $\mu m^2$, or between about 2500 $\mu m^2$ and 100000 $\mu m^2$, or between about 5000 $\mu m^2$ and 50000 $\mu m2$, or between about 7500 $\mu m^2$ and 40000 $\mu m^2$, or between about 10000 $\mu m^2$ and 25000 $\mu m^2$. In some embodiments, the irregularly shaped particles that originate from a bulk hydrogel comprise "shred particles". Shred particles comprise, for example, particles that are created by separating a bulk hydrogel by physical force. Manual separation may suffice, as well as mechanical means, such as forcing a bulk hydrogel through a sieve or grate with pores of a size that yields the desired particle size. For example, a cell strainer can be used with a centrifuge to force a bulk hydrogel through the grate, creating shredded, or "shred" particles.

Figure 7A:
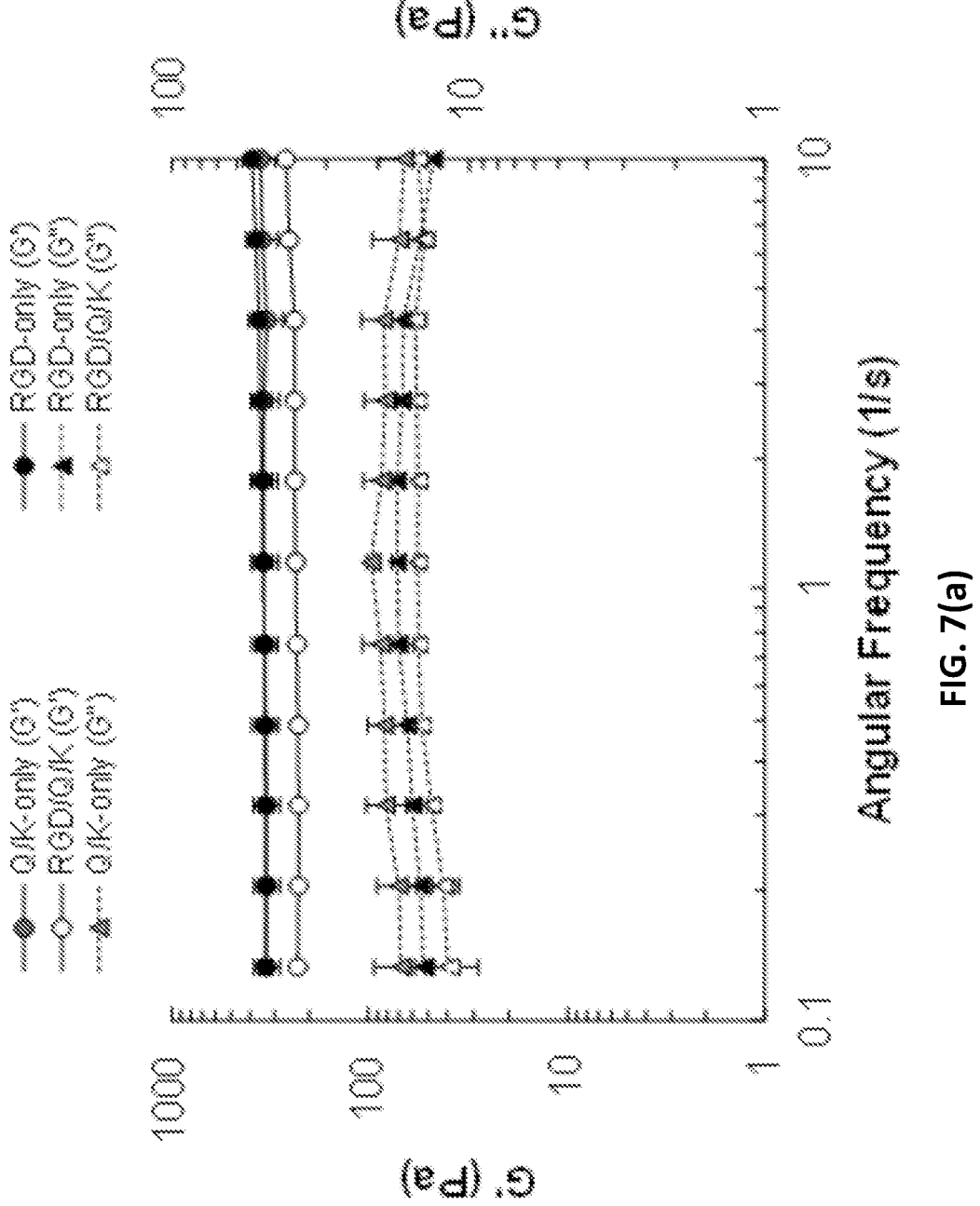
(FIG. 7A) Rheology of FLIP scaffolds from 70 μm sieving, with and without annealing chemistry (lack of Q/K peptides for FXIII-mediated annealing).
Figure 7B:
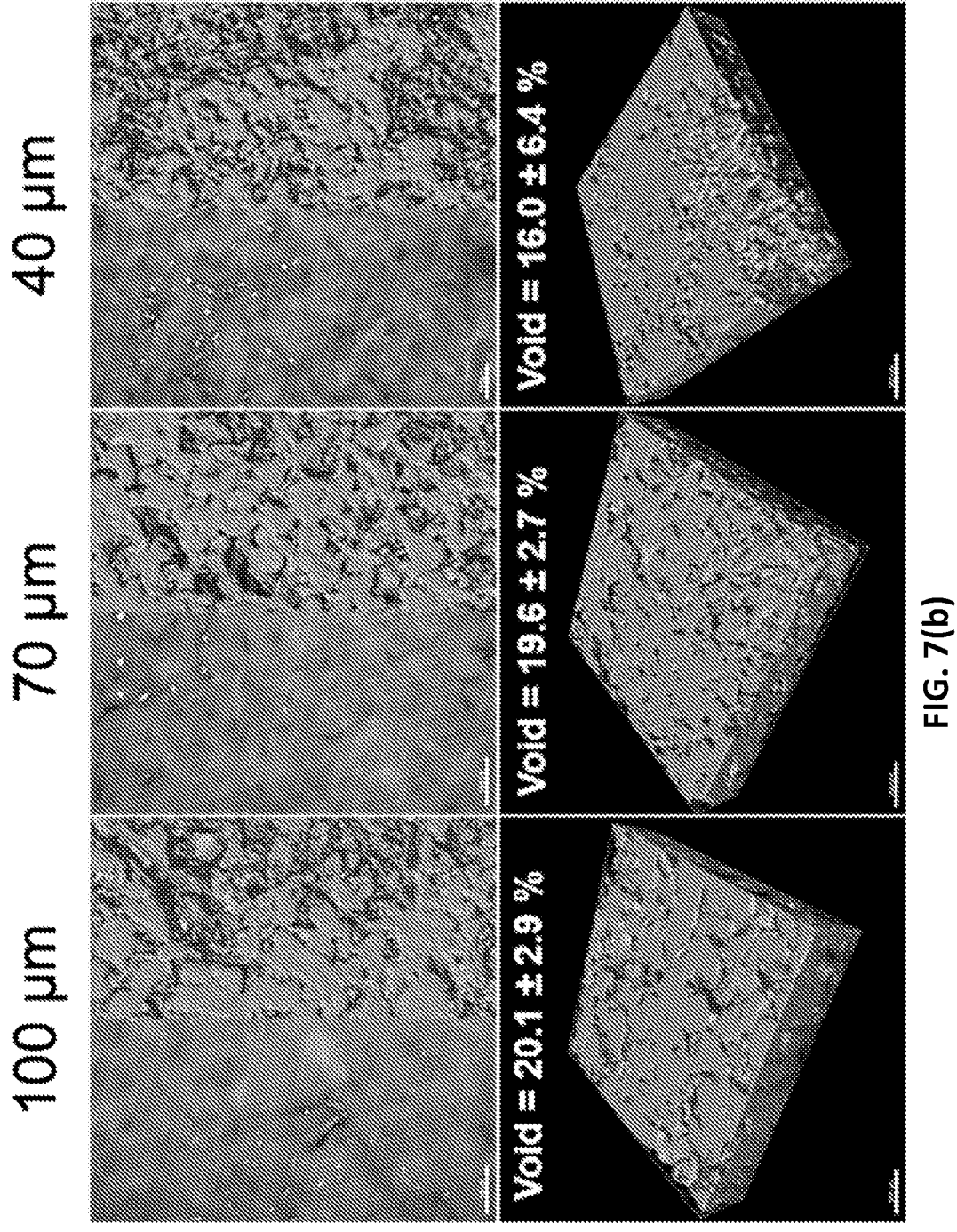
(FIG. 7B) Annealed FLIP scaffolds from different sieve sizes, with dextran imaging of the interstitial void space to quantify porosity, n=3. Renderings performed from confocal microscopy images in IMARIS, with half corresponding to maximum intensity projection, and half from model volume filling.
Figure 8A:
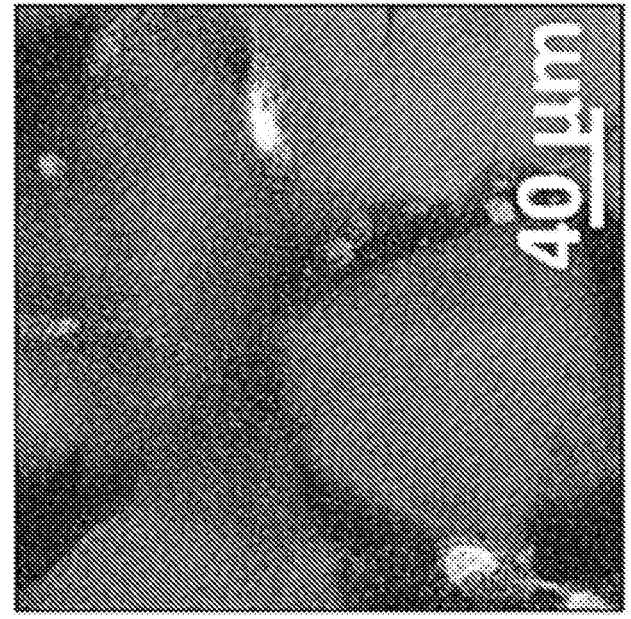
FIG. 8 shows that Cells are encapsulated without loss of viability. (Left) Top-down view of actin stained cells for spreading within the FLIP scaffold, imaged half-way into the gel following seeding on top. (Right) IMARIS rendering of confocal images across a z-stack array to observe cell infiltration and spreading within the annealed scaffold.
Figure 8A:
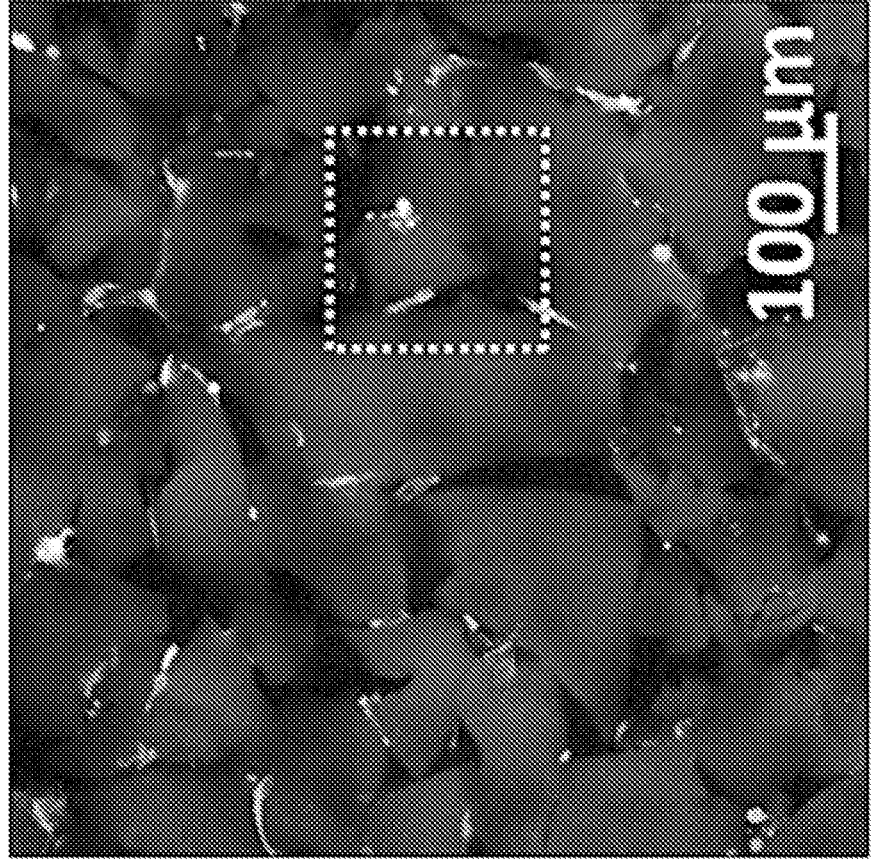
Figure 8B:
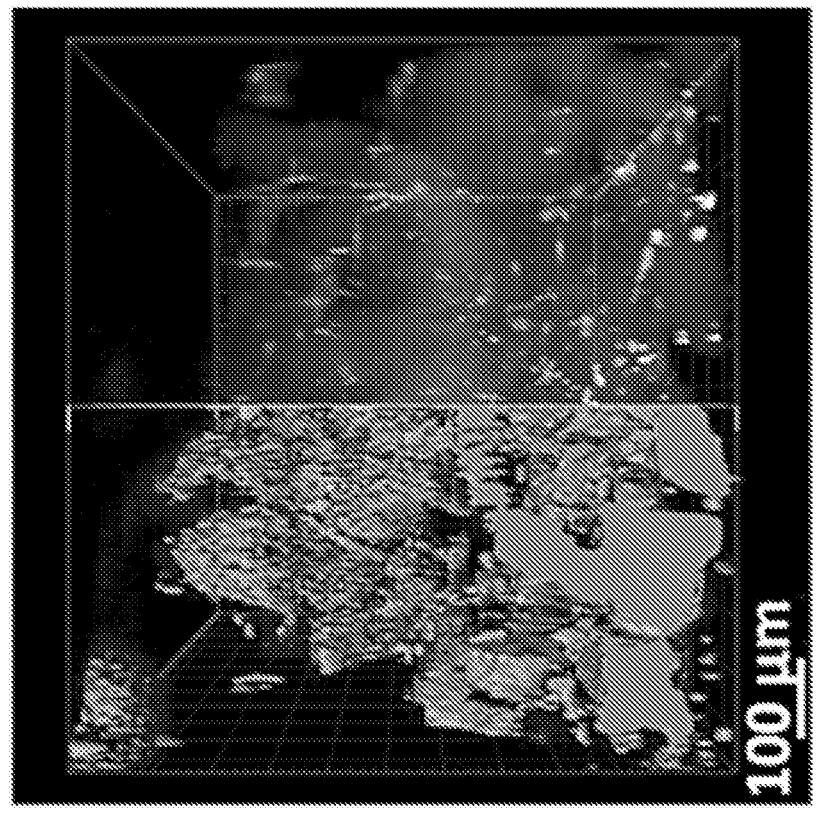
Figure 8B:
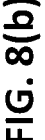
Figure 8B:
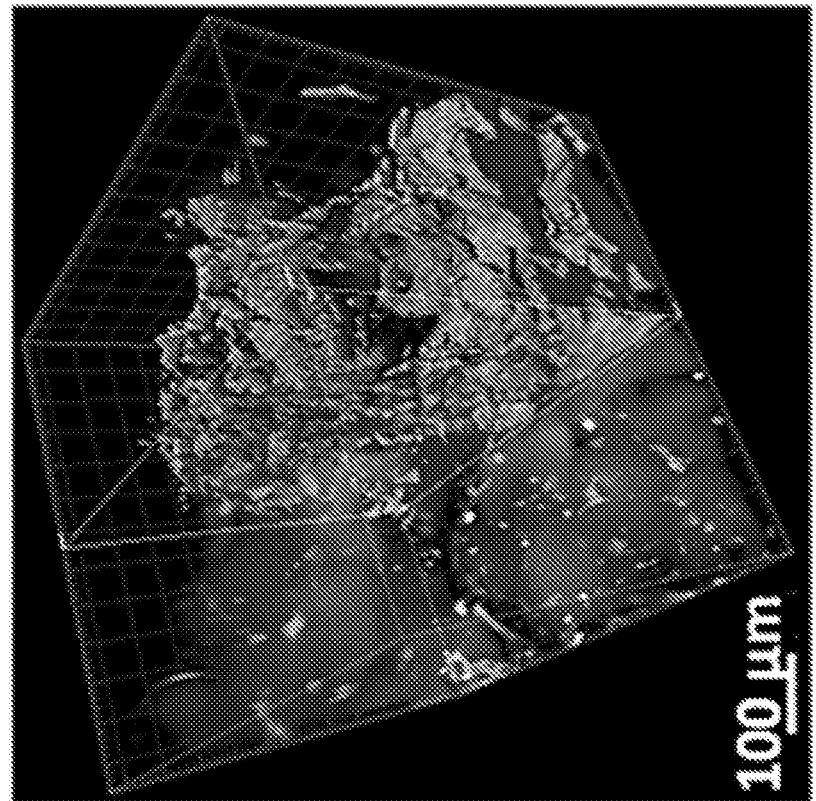

In some embodiments, two or more particles, of any composition as described above, are annealed together, wherein annealed together comprises covalent, electrostatic, hydrophobic and mechanical annealing. As seen in, e.g., FIG. 7, non-annealed scaffolds also can possess physical properties like stiffness in the range of some annealed scaffolds. Both annealed and non-annealed scaffolds are contemplated and useful for aspects and embodiments of the disclosure.

In some embodiments, nucleic acids comprise DNA and RNA. DNA comprises all forms of natural, synthetic, purified, isolated, recombinant, or combinations thereof, of deoxyribonucleic acid, e.g., plasmid DNA, ssDNA, dsDNA, cDNA and minicircle DNA. RNA comprises all forms of natural, synthetic, purified, isolated, recombinant, or combinations thereof, of ribonucleic acid, e.g., mRNA, pre-mRNA, siRNA, shRNA, ssRNA, antisense RNA oligonucleotide, antisense miRNA, trans-splicing RNA, guide RNA, single-guide RNA, crRNA, tracrRNA and trans-splicing RNA.

Naked nucleic acid can be used in aspects and embodiments of the disclosure, directly packaged into a hydrogel particle. Complexing nucleic acids with other compounds to, as one example, counteract or balance its negative charge, can offer advantages of delivery efficiency (of nucleic acid to a target cell), half-life, and others. In some embodiments, nucleic acid is combined with one or more nucleic acid complexing agents. In some embodiments, the one or more nucleic acid complexing agents comprises a cationic polymer, cationic peptide, cationic lipid, a functional equivalent of any of the preceding, or mixtures thereof.

In some embodiments, the cationic polymer comprises linear and branched poly(ethyleneimine) (PEI), poly(beta-amino esters), Poly(2-(dimethylamino)ethyl methacrylate) (pDMEAMA); poly(amido amine) (PAMAM), chitosan, imine-containing polyamines, polyurethans, cyclodextrin, disulfide-containing poly(amido amine), a functional equivalent of any of the preceding, and mixtures thereof.

In some embodiments, the cationic peptide comprises one or more of KALA, GALA, MAP, LAH4, Melittin-derived peptide, p5RHH, poly(L-lysine) (PLL), poly(D-lysine) (PDL), poly(L-histidine), poly(D-histidine), protonatable amine-containing peptide, a functional equivalent of any of the preceding, and mixtures thereof.

In some embodiments, the cationic lipid comprises lipofectamine, DOSPA, DOPE, DSPE, DSTAP, DOTAP, DOTMA, DORIE, DMRIE, DOTIM, GAP-DLRIE, DDAB, DC-6-14, DODAP, DOTC, DOGS, a functional equivalent of any of the preceding, and mixtures thereof.

In some embodiments, the nucleic acid and the nucleic acid complexing agent are mixed at a N/P ratio, which describes a ratio of positively-chargeable polymer amine (N=nitrogen) groups to negatively-charged nucleic acid phosphate (P) groups. In some embodiments, the N/P ratio comprises between about 1 and 100, or between about 1 and 90, or between about 2 and 75, or between about 3 and 65, or between about 4 and 50. In some embodiments of the scaffold, the nucleic acid is DNA and the complexing agent is PEI, the N/P ratio comprises between about 5 and 35, or between about 15 and 25, or about 20.

In some embodiments, the polyplexes further comprise a coating layer. In some embodiments, the coating layer can comprise one or more coating layer agents, which, in some embodiments, comprise one or more biocompatible polymers, one or more mineral salts, and mixtures thereof.

In some embodiments, the one or more biocompatible polymers comprise unmodified hyaluronic acid (HA), modified HA, alginate, PEGylated anionic peptides, poly (HEMA), poly(vinyl alcohol), poly sulfates, dextran, collagen, gelatin, chitosan, a functional equivalent of any of the preceding and mixtures thereof.

In some embodiments, the modified HA comprises HA-norbornene, HA-acrylamide, HA-tetrazine, HA-sulfate, HA-cyclodextrin, HA-adamantane, HA-vinyl sulfone, HA-acrylate, HA-allyl, HA-azide, HA-alkyne, HA-thiol, HA-PEG, a functional equivalent of any of the preceding and mixtures thereof.

In some embodiments, the one or more mineral salts comprise calcium carbonate, magnesium sulfate, calcium sulfate and mixtures thereof.

In some embodiments, the polymer is bound to one or more peptides comprising at least three consecutive amino acids from an extracellular matrix protein. In some embodiments, the peptide comprises an integrin binding peptide, and in some embodiments, comprises an RGD peptide. In some embodiments, the polymer is bound to peptides of two or more different sequences.

In some embodiments, the one or more nucleic acid complexing agents and one or more coating layer agents are mixed at a coating/complexing ratio. The coating/complexing ratio represents a weight/weight ratio. In some embodiments, the coating/complexing ratio comprises between about 0.1 and 100, or between about 0.5 and 75, or between about 0.5 and 50, or between about 1 and 40, or between about 1 and 30, or between about 1 and 25, or between about 1 and 20. In some embodiments, of the scaffold the nucleic acid comprises DNA, the nucleic acid complexing agent comprises PEI, the N/P ratio comprises between about 2 and 7, or between about 3 and 5, and the coating/complexing ratio comprises between about 1 and 8, or between about 2 and 6, or between about 2 and 5.

In some embodiments, the polyplexes comprise lyophilized polyplexes, and in some embodiments, further comprise a cryoprotectant. In some embodiments, the cryoprotectant comprises one or more of sucrose, trehalose, proline, lysine, lactose, lactosucrose, low melting point agarose, taurine, a functional equivalent of any of the preceding, and combinations thereof. In some embodiments, the cryoprotectant comprises sucrose, and in some embodiments the sucrose comprises between about 10 to 500 μg per μg of nucleic acid, or between about 20 to 400 μg per μg of nucleic acid, or between about 25 to 350 μg per μg of nucleic acid, or between about 30 to 300 μg per μg of nucleic acid, or between about 35 to 250 μg per μg of nucleic acid, or between about 40 to 200 μg per μg of nucleic acid.

In some embodiments, the nucleic acid comprises DNA, the nucleic acid complexing agent comprises PEI, the N/P ratio comprises between about 15 to 25, the cryoprotectant comprises sucrose at between about 60 to 110 μg per μg DNA.

In some embodiments, the concentration of the nucleic acid comprises between about 0.1 mg/ml nucleic acid and 20 mg/ml nucleic acid, or between about 0.2 mg/ml nucleic acid and 18 mg/ml nucleic acid, or between about 0.25 mg/ml nucleic acid and 16 mg/ml nucleic acid, or between about 0.3 mg/ml nucleic acid and 14 mg/ml nucleic acid, or between about 0.4 mg/ml nucleic acid and 12 mg/ml nucleic acid, or between about 0.5 mg/ml nucleic acid and 10 mg/ml nucleic acid, or between about 0.5 mg/ml nucleic acid and 8 mg/ml nucleic acid, or between about 0.5 mg/ml nucleic acid and 7 mg/ml nucleic acid, or between about 0.5 mg/ml nucleic acid and 6 mg/ml nucleic acid, or between about 0.5 mg/ml nucleic acid and 5 mg/ml nucleic acid, or between about 0.6 mg/ml nucleic acid and 6 mg/ml nucleic acid, or between about 0.7 mg/ml nucleic acid and 7 mg/ml nucleic acid, or between about 0.8 mg/ml nucleic acid and 8 mg/ml nucleic acid, or between about 0.9 mg/ml nucleic acid and 9 mg/ml nucleic acid, or between about 1 mg/ml nucleic acid and 10 mg/ml nucleic acid, or between about 1 mg/ml nucleic acid and 7.5 mg/ml nucleic acid, or between about 1 mg/ml nucleic acid and 5 mg/ml nucleic acid.

Another aspect of the disclosure provides a structure for localized and controlled release of nucleic acids, comprising a scaffold comprising hydrogel particles, wherein the particles comprise one or more polyplexes, which polyplexes comprise one or more copies of one or more nucleic acids and one or more nucleic acid complexing agents, wherein the one or more nucleic acids is present at a total concentration of at least about 0.1 mg/ml, and further wherein the scaffold is characterized in that, when the structure is placed in contact with cells of a subject so that the scaffold contacts the cells, the nucleic acid is released with a profile characterized by one or more of (a) a burst-free release; (b) a sustained release; and (c) exhibiting in vitro and/or in vivo biological effectiveness.

In some embodiments, scaffold comprises one or more particles that is devoid of nucleic acids, nucleic acid complexing agents and/or polyplexes, with the proviso that not all particles are devoid of nucleic acid, nucleic acid complexing agent and/or polyplexes. As in some other embodiments, for particles that originate from a bulk hydrogel and for particles that are discretely polymerized, some particles may comprise empty particles. Such particles are contemplated and useful for use along with loaded particles. In some embodiments of this aspect of the disclosure, empty and loaded particles can be organized, layered, placed and otherwise arranged in 2D and 3D space to accomplish different goals. Particles with different hydrogel compositions, different polyplex compositions (both nucleic acids and nucleic acid complexing agent(s)), empty and loaded for each case, discretely polymerized, originating from a bulk hydrogel or both, can be specifically arranged. For example, a structure for localized and controlled release of nucleic acids can comprise different (or not) nucleic acids in different (or not) areas or regions of the structure to be delivered to different (or not) cells or tissues with different (or not) efficiencies based on the compositions of each component of the scaffold of the disclosure. Thus, in some embodiments, the scaffold comprises particles of two or more types. One or more same or different nucleic acids can be delivered to one or more cells and/or tissues to affect one or more biological targets.

In some embodiments, the concentration of the nucleic acid comprises at least about 0.1 mg/ml, about 0.2 mg/ml, about 0.3 mg/ml, about 0.4 mg/ml, about 0.5 mg/ml, about 0.6 mg/ml, about 0.7 mg/ml, about 0.8 mg/ml, about 0.9 mg/ml, about 1 mg/ml, about 1.5 mg/ml, about 2 mg/ml, about 2.5 mg/ml, about 3 mg/ml, about 3.5 mg/ml, about 4 mg/ml, about 4.5 mg/ml, about 5 mg/ml, about 5.5 mg/ml, about 6 mg/ml, about 6.5 mg/ml, about 7 mg/ml, about 7.5 mg/ml, about 8 mg/ml, about 8.5 mg/ml, about 9 mg/ml, about 9.5 mg/ml, about 10 mg/ml, about 11 mg/ml, about 12 mg/ml, about 13 mg/ml, about 14 mg/ml, about 15 mg/ml, about 16 mg/ml, about 17 mg/ml, about 18 mg/ml, about 19 mg/ml, about 20 mg/ml, and additional concentrations therein.

In some embodiments, the burst-free release is characterized by releasing less than about 5%, about 10%, about 15%, about 20%, about 25%, about 30%, about 35%, about 40%, about 45% or about 50% of the nucleic acid agent in the first 24 hours after placement on the subject In some embodiments, the sustained release is characterized by the nucleic acid being released from the scaffold over an extended period of time of at least about 3 days, about 5 days, about 7 days, about 10 days, about 15 days, about 30 days, about 1 month, about 2 months, about 3 months, about 6 months, or about 1 year.

In some embodiments, one or more particles originates from a bulk hydrogel, and in some embodiments, one or more particles can also be discretely polymerized, and mixtures thereof. In some embodiments, polyplexes are substantially evenly distributed throughout particles that originate from a bulk hydrogel, and in some embodiments, at least one particle comprises an irregular shape. In some embodiments, particles comprise regular and irregular shapes.

In some embodiments, the scaffold that comprises the structure for localized and controlled release of nucleic acids, comprises hydrogel particles of two or more types.

In some embodiments, the scaffold comprises one or more particles that comprise an irregular shape, which irregularly shaped particles comprise an average surface area that can range from between about 100 $\mu m^2$ and 1000000 $\mu m^2$, or between about 500 $\mu m^2$ and 500000 $\mu m^2$, or between about 1000 $\mu m^2$ and 250000 $\mu m^2$, or between about 2500 $\mu m^2$ and 100000 $\mu m^2$, or between about 5000 $\mu m^2$ and 50000 $\mu m^2$, or between about 7500 $\mu m^2$ and 40000 $\mu m^2$, or between about 10000 $\mu m^2$ and 25000 $\mu m^2$.

In some embodiments, the irregularly shaped particles comprise shred particles. In some embodiments, two or more particles of any type of the disclosure are annealed together, wherein annealed together comprises covalent, electrostatic, hydrophobic and mechanical annealing. In some embodiments, non-annealed scaffolds of two or more particles are contemplated and useful for aspects and embodiments of the disclosure.

In some embodiments, nucleic acids comprise DNA and RNA. DNA comprises all forms of natural, synthetic, purified, isolated, recombinant, or combinations thereof, of deoxyribonucleic acid, e.g., plasmid DNA, ssDNA, dsDNA, cDNA and minicircle DNA. RNA comprises all forms of natural, synthetic, purified, isolated, recombinant, or combinations thereof, of ribonucleic acid, e.g., mRNA, pre-mRNA, siRNA, shRNA, ssRNA, antisense RNA oligonucleotide, antisense miRNA, trans-splicing RNA, guide RNA, single-guide RNA, crRNA, tracrRNA and trans-splicing RNA.

Naked nucleic acid can be used in aspects and embodiments of the disclosure, directly packaged into a hydrogel particle. In some embodiments, nucleic acid is combined with one or more nucleic acid complexing agents. In some embodiments, the one or more nucleic acid complexing agents comprises a cationic polymer, cationic peptide, cationic lipid, a functional equivalent of any of the preceding, or mixtures thereof.

In some embodiments, the cationic polymer comprises linear and branched poly(ethyleneimine) (PEI), poly(beta-amino esters), Poly(2-(dimethylamino)ethyl methacrylate) (pDMEAMA); poly(amido amine) (PAMAM), chitosan, imine-containing polyamines, polyurethans, cyclodextrin, disulfide-containing poly(amido amine), a functional equivalent of any of the preceding, and mixtures thereof.

In some embodiments, the cationic peptide comprises one or more of KALA, GALA, MAP, LAH4, Melittin-derived peptide, p5RHH, poly(L-lysine) (PLL), poly(D-lysine) (PDL), poly(L-histidine), poly(D-histidine), protonatable amine-containing peptide, a functional equivalent of any of the preceding, and mixtures thereof.

In some embodiments, the cationic lipid comprises lipofectamine, DOSPA, DOPE, DSPE, DSTAP, DOTAP, DOTMA, DORIE, DMRIE, DOTIM, GAP-DLRIE, DDAB, DC-6-14, DODAP, DOTC, DOGS, a functional equivalent of any of the preceding, and mixtures thereof.

In some embodiments, the nucleic acid and the nucleic acid complexing agent are mixed at a N/P ratio, defined above. In some embodiments, the N/P ratio comprises between about 1 and 100, or between about 1 and 90, or between about 2 and 75, or between about 3 and 65, or between about 4 and 50. In some embodiments of the structure for localized and controlled release of nucleic acids, the nucleic acid is DNA and the complexing agent is PEI, the N/P ratio comprises between about 5 and 35, or between about 15 and 25, or about 20.

In some embodiments, the polyplexes further comprise a coating layer. In some embodiments, the coating layer can comprise one or more coating layer agents, which, in some embodiments, comprise one or more biocompatible polymers, one or more mineral salts, and mixtures thereof.

In some embodiments, the one or more biocompatible polymers comprise unmodified hyaluronic acid (HA), modified HA, alginate, PEGylated anionic peptides, poly (HEMA), poly(vinyl alcohol), poly sulfates, dextran, collagen, gelatin, chitosan, a functional equivalent of any of the preceding and mixtures thereof.

In some embodiments, the modified HA comprises HA-norbornene, HA-acrylamide, HA-tetrazine, HA-sulfate, HA-cyclodextrin, HA-adamantane, HA-vinyl sulfone, HA-acrylate, HA-allyl, HA-azide, HA-alkyne, HA-thiol, HA-PEG, a functional equivalent of any of the preceding and mixtures thereof.

In some embodiments, the one or more mineral salts comprise calcium carbonate, magnesium sulfate, calcium sulfate and mixtures thereof.

In some embodiments, the polymer is bound to one or more peptides comprising at least three consecutive amino acids from an extracellular matrix protein. In some embodiments, the peptide comprises an integrin binding peptide, and in some embodiments, comprises an RGD peptide. In some embodiments, the polymer is bound to peptides of two or more different sequences.

In some embodiments, the one or more nucleic acid complexing agents and one or more coating layer agents are mixed at a coating/complexing ratio. The coating/complexing ratio represents a weight/weight ratio. In some embodiments, the coating/complexing ratio comprises between about 0.1 and 100, or between about 0.5 and 75, or between about 0.5 and 50, or between about 1 and 40, or between about 1 and 30, or between about 1 and 25, or between about 1 and 20. In some embodiments, of the scaffold the nucleic acid comprises DNA, the nucleic acid complexing agent comprises PEI, the N/P ratio comprises between about 2 and 7, or between about 3 and 5, and the coating/complexing ratio comprises between about 1 and 8, or between about 2 and 6, or between about 2 and 5.

In some embodiments, the polyplexes comprise lyophilized polyplexes, and in some embodiments, further comprise a cryoprotectant. In some embodiments, the cryoprotectant comprises one or more of sucrose, trehalose, proline, lysine, lactose, lactosucrose, low melting point agarose, taurine, a functional equivalent of any of the preceding, and combinations thereof. In some embodiments, the cryoprotectant comprises sucrose, and in some embodiments the sucrose comprises between about 10 to 500 μg per μg of nucleic acid, or between about 20 to 400 μg per μg of nucleic acid, or between about 25 to 350 μg per μg of nucleic acid, or between about 30 to 300 μg per μg of nucleic acid, or between about 35 to 250 μg per μg of nucleic acid, or between about 40 to 200 μg per μg of nucleic acid.

In some embodiments, the nucleic acid comprises DNA, the nucleic acid complexing agent comprises PEI, the N/P ratio comprises between about 15 to 25, the cryoprotectant comprises sucrose at between about 60 to 110 μg per μg DNA.

In some embodiments, the structure for localized and controlled release of nucleic acids comprises an effective amount of one or more nucleic acids effective for nucleic acid therapy. In some embodiments, the structure for localized and controlled release of nucleic acids comprises an effective amount of one or more nucleic acids effective for tissue engineering. In some embodiments, the structure for localized and controlled release of nucleic acids comprises an effective amount of one or more nucleic acids effective for vaccine development.

Another aspect of the disclosure provides a pharmaceutical composition of hydrogel particles comprising one or more polyplexes, which polyplexes encapsulate a therapeutically effective amount of at least one bioactive nucleic acid.

In some embodiments, the pharmaceutical composition comprises one or more particles devoid of nucleic acid, nucleic acid complexing agent and/or polyplexes, with the proviso that not all particles are devoid of nucleic acid, nucleic acid complexing agent and/or polyplexes. As in some other embodiments, for particles that originate from a bulk hydrogel and for particles that are discretely polymerized, some particles may comprise empty particles. Such particles are contemplated and useful for use along with loaded particles. In some embodiments of this aspect of the disclosure, empty and loaded particles can be organized, layered, placed and otherwise arranged in 2D and 3D space to accomplish different goals. Particles with different hydrogel compositions, different polyplex compositions (both nucleic acids and nucleic acid complexing agent(s)), empty and loaded for each case, discretely polymerized, originating from a bulk hydrogel or both, can be specifically arranged. For example, a pharmaceutical composition can comprise different (or not) nucleic acids in different (or not) areas or regions of the pharmaceutical composition to be delivered to different (or not) cells or tissues with different (or not) efficiencies based on the compositions of each component of the pharmaceutical composition of the disclosure. Thus, in some embodiments, the pharmaceutical composition comprises particles of two or more types. One or more same or different bioactive nucleic acids can be delivered to one or more cells and/or tissues to affect one or more biological targets. A 2D example could be a pharmaceutical composition on the surface of or impregnated within a customized or standard bandage to treat a wound with one or more bioactive nucleic acids in different areas of the wound. If injected, the pharmaceutical composition could have different bioactive nucleic acids, particle or hydrogel compositions arranged within a 3D bolus (e.g., intramuscular, subcutaneous). Bioactive nucleic acids near the periphery of the 3D bolus could be of one composition for initial treatment, where more centrally located bioactive nucleic acids could be intended for second effector treatment. Thus, in some embodiments, the pharmaceutical composition comprises hydrogel particles of two or more types.

In some embodiments, one or more particles originates from a bulk hydrogel, and in some embodiments, one or more particles can also be discretely polymerized, and mixtures thereof. In some embodiments, polyplexes are substantially evenly distributed throughout particles that originate from a bulk hydrogel, and in some embodiments, at least one particle comprises an irregular shape. In some embodiments, particles comprise regular and irregular shapes.

In some embodiments of the pharmaceutical composition, the one or more particles that comprises an irregular shape further comprises an average surface area of between about 100 $\mu m^2$ and 1000000 $\mu m2$, or between about 500 $\mu m^2$ and 500000 $\mu m^2$, or between about 1000 $\mu m^2$ and 250000 $\mu m^2$, or between about 2500 $\mu m^2$ and 100000 $\mu m^2$, or between about 5000 $\mu m^2$ and 50000 $\mu m^2$, or between about 7500 $\mu m^2$ and 40000 $\mu m^2$, or between about 10000 $\mu m^2$ and 25000 $\mu m^2$. In some embodiments, the irregularly shaped particles comprise shred particles. In some embodiments, two or more particles are annealed together, wherein annealed together comprises covalent, electrostatic, hydrophobic and mechanical annealing. In some embodiments, non-annealed pharmaceutical compositions of two or more particles are contemplated and useful for aspects and embodiments of the disclosure.

In some embodiments, nucleic acids comprise DNA and RNA. DNA comprises all forms of natural, synthetic, purified, isolated, recombinant, or combinations thereof, of deoxyribonucleic acid, e.g., plasmid DNA, ssDNA, dsDNA, cDNA and minicircle DNA. RNA comprises all forms of natural, synthetic, purified, isolated, recombinant, or combinations thereof, of ribonucleic acid, e.g., mRNA, pre-mRNA, siRNA, shRNA, ssRNA, antisense RNA oligonucleotide, antisense miRNA, trans-splicing RNA, guide RNA, single-guide RNA, crRNA, tracrRNA and trans-splicing RNA.

Naked nucleic acid can be used in aspects and embodiments of the disclosure, directly packaged into a hydrogel particle. In some embodiments, nucleic acid is combined with one or more nucleic acid complexing agents. In some embodiments, the one or more nucleic acid complexing agents comprises a cationic polymer, cationic peptide, cationic lipid, a functional equivalent of any of the preceding, or mixtures thereof.

In some embodiments, the cationic polymer comprises linear and branched poly(ethyleneimine) (PEI), poly(beta-amino esters), Poly(2-(dimethylamino)ethyl methacrylate) (pDMEAMA); poly(amido amine) (PAMAM), chitosan, imine-containing polyamines, polyurethans, cyclodextrin, disulfide-containing poly(amido amine), a functional equivalent of any of the preceding, and mixtures thereof.

In some embodiments, the cationic peptide comprises one or more of KALA, GALA, MAP, LAH4, Melittin-derived peptide, p5RHH, poly(L-lysine) (PLL), poly(D-lysine) (PDL), poly(L-histidine), poly(D-histidine), protonatable amine-containing peptide, a functional equivalent of any of the preceding, and mixtures thereof.

In some embodiments, the cationic lipid comprises lipofectamine, DOSPA, DOPE, DSPE, DSTAP, DOTAP, DOTMA, DORIE, DMRIE, DOTIM, GAP-DLRIE, DDAB, DC-6-14, DODAP, DOTC, DOGS, a functional equivalent of any of the preceding, and mixtures thereof.

In some embodiments, the nucleic acid and the nucleic acid complexing agent are mixed at a N/P ratio, defined above. In some embodiments, the N/P ratio comprises between about 1 and 100, or between about 1 and 90, or between about 2 and 75, or between about 3 and 65, or between about 4 and 50. In some embodiments of the pharmaceutical composition, the nucleic acid is DNA and the complexing agent is PEI, the N/P ratio comprises between about 5 and 35, or between about 15 and 25, or about 20.

In some embodiments, the polyplexes further comprise a coating layer. In some embodiments, the coating layer can comprise one or more coating layer agents, which, in some embodiments, comprise one or more biocompatible polymers, one or more mineral salts, and mixtures thereof.

In some embodiments, the one or more biocompatible polymers comprise unmodified hyaluronic acid (HA), modified HA, alginate, PEGylated anionic peptides, poly (HEMA), poly(vinyl alcohol), poly sulfates, dextran, collagen, gelatin, chitosan, a functional equivalent of any of the preceding and mixtures thereof.

In some embodiments, the modified HA comprises HA-norbornene, HA-acrylamide, HA-tetrazine, HA-sulfate, HA-cyclodextrin, HA-adamantane, HA-vinyl sulfone, HA-acrylate, HA-allyl, HA-azide, HA-alkyne, HA-thiol, HA-PEG, a functional equivalent of any of the preceding and mixtures thereof.

In some embodiments, the one or more mineral salts comprise calcium carbonate, magnesium sulfate, calcium sulfate and mixtures thereof.

In some embodiments, the polymer is bound to one or more peptides comprising at least three consecutive amino acids from an extracellular matrix protein. In some embodiments, the peptide comprises an integrin binding peptide, and in some embodiments, comprises an RGD peptide. In some embodiments, the polymer is bound to peptides of two or more different sequences.

In some embodiments, the one or more nucleic acid complexing agents and one or more coating layer agents are mixed at a coating/complexing ratio. The coating/complexing ratio represents a weight/weight ratio. In some embodiments, the coating/complexing ratio comprises between about 0.1 and 100, or between about 0.5 and 75, or between about 0.5 and 50, or between about 1 and 40, or between about 1 and 30, or between about 1 and 25, or between about 1 and 20. In some embodiments, of the scaffold the nucleic acid comprises DNA, the nucleic acid complexing agent comprises PEI, the N/P ratio comprises between about 2 and 7, or between about 3 and 5, and the coating/complexing ratio comprises between about 1 and 8, or between about 2 and 6, or between about 2 and 5.

In some embodiments, the polyplexes comprise lyophilized polyplexes, and in some embodiments, further comprise a cryoprotectant. In some embodiments, the cryoprotectant comprises one or more of sucrose, trehalose, proline, lysine, lactose, lactosucrose, low melting point agarose, taurine, a functional equivalent of any of the preceding, and combinations thereof. In some embodiments, the cryoprotectant comprises sucrose, and in some embodiments the sucrose comprises between about 10 to 500 $\mu g$ per $\mu g$ of nucleic acid, or between about 20 to 400 $\mu g$ per $\mu g$ of nucleic acid, or between about 25 to 350 $\mu g$ per $\mu g$ of nucleic acid, or between about 30 to 300 $\mu g$ per $\mu g$ of nucleic acid, or between about 35 to 250 $\mu g$ per $\mu g$ of nucleic acid, or between about 40 to 200 $\mu g$ per $\mu g$ of nucleic acid.

In some embodiments, the nucleic acid comprises DNA, the nucleic acid complexing agent comprises PEI, the N/P ratio comprises between about 15 to 25, the cryoprotectant comprises sucrose at between about 60 to 110 $\mu g$ per $\mu g$ DNA.

In some embodiments, the concentration of the nucleic acid comprises between about 0.1 mg/ml nucleic acid and 20 mg/ml nucleic acid, or between about 0.2 mg/ml nucleic acid and 18 mg/ml nucleic acid, or between about 0.25 mg/ml nucleic acid and 16 mg/ml nucleic acid, or between about 0.3 mg/ml nucleic acid and 14 mg/ml nucleic acid, or between about 0.4 mg/ml nucleic acid and 12 mg/ml nucleic acid, or between about 0.5 mg/ml nucleic acid and 10 mg/ml nucleic acid, or between about 0.5 mg/ml nucleic acid and 8 mg/ml nucleic acid, or between about 0.5 mg/ml nucleic acid and 7 mg/ml nucleic acid, or between about 0.5 mg/ml nucleic acid and 6 mg/ml nucleic acid, or between about 0.5 mg/ml nucleic acid and 5 mg/ml nucleic acid, or between about 0.6 mg/ml nucleic acid and 6 mg/ml nucleic acid, or between about 0.7 mg/ml nucleic acid and 7 mg/ml nucleic acid, or between about 0.8 mg/ml nucleic acid and 8 mg/ml nucleic acid, or between about 0.9 mg/ml nucleic acid and 9 mg/ml nucleic acid, or between about 1 mg/ml nucleic acid and 10 mg/ml nucleic acid, or between about 1 mg/ml nucleic acid and 7.5 mg/ml nucleic acid, or between about 1 mg/ml nucleic acid and 5 mg/ml nucleic acid.

In some embodiments, the pharmaceutical composition comprises an effective amount of one or more nucleic acids effective for nucleic acid therapy. In some embodiments, the pharmaceutical composition comprises an effective amount of one or more nucleic acids effective for tissue engineering. In some embodiments, the pharmaceutical composition comprises an effective amount of one or more nucleic acids effective for vaccine development.

Another aspect of the disclosure provides a method of nucleic acid delivery to a cell, comprising contacting a cell with two or more hydrogel particles, wherein the particles comprise one or more polyplexes, which polyplexes comprise one or more copies of one or more nucleic acids and one or more nucleic acid complexing agents.

In some embodiments, the method of nucleic acid delivery to a cell comprises one or more particles that is devoid of nucleic acids, nucleic acid complexing agents and/or polyplexes, with the proviso that not all particles are devoid of nucleic acid, nucleic acid complexing agent and/or polyplexes. As in some other embodiments, for particles that originate from a bulk hydrogel and for particles that are discretely polymerized, some particles may comprise empty particles. Such particles are contemplated and useful for use along with loaded particles. In some embodiments of this aspect of the disclosure, empty and loaded particles can be organized, layered, placed and otherwise arranged in 2D and 3D space to accomplish different goals. Particles with different hydrogel compositions, different polyplex compositions (both nucleic acids and nucleic acid complexing agent(s)), empty and loaded for each case, discretely polymerized, originating from a bulk hydrogel or both, can be specifically arranged. For example, a method of nucleic acid delivery to a cell can comprise contacting a cell with different (or not) nucleic acids in different (or not) areas or regions of the composition to be delivered to different (or not) cells or tissues with different (or not) efficiencies based on the compositions of each component of the composition being utilized in the methods of the disclosure. Thus, in some embodiments, the method comprises particles of two or more types. One or more same or different nucleic acids can contact a cell or cells to affect one or more biological targets.

In some embodiments, one or more particles originates from a bulk hydrogel, and in some embodiments, one or more particles can also be discretely polymerized, and mixtures thereof. In some embodiments, polyplexes are substantially evenly distributed throughout particles that originate from a bulk hydrogel, and in some embodiments, at least one particle comprises an irregular shape. In some embodiments, particles comprise regular and irregular shapes.

In some embodiments of the method, the one or more particles that comprises an irregular shape further comprises an average surface area of between about 100 $\mu m^2$ and 1000000 $\mu m^2$, or between about 500 $\mu m^2$ and 500000 $\mu m^2$, or between about 1000 $\mu m^2$ and 250000 $\mu m^2$, or between about 2500 $\mu m^2$ and 100000 $\mu m^2$, or between about 5000 $\mu m^2$ and 50000 $\mu m^2$, or between about 7500 $\mu m^2$ and 40000 $\mu m^2$, or between about 10000 $\mu m^2$ and 25000 $\mu m^2$. In some embodiments, the irregularly shaped particles comprise shred particles. In some embodiments, two or more particles are annealed together, wherein annealed together comprises covalent, electrostatic, hydrophobic and mechanical annealing. In some embodiments, the two or more particles are not annealed, and such unannealed particles are contemplated and useful for aspects and embodiments of the disclosure.

In some embodiments, nucleic acids comprise DNA and RNA. DNA comprises all forms of natural, synthetic, purified, isolated, recombinant, or combinations thereof, of deoxyribonucleic acid, e.g., plasmid DNA, ssDNA, dsDNA, cDNA and minicircle DNA. RNA comprises all forms of natural, synthetic, purified, isolated, recombinant, or combinations thereof, of ribonucleic acid, e.g., mRNA, pre-mRNA, siRNA, shRNA, ssRNA, antisense RNA oligonucleotide, antisense miRNA, trans-splicing RNA, guide RNA, single-guide RNA, crRNA, tracrRNA and trans-splicing RNA.

Naked nucleic acid can be used in aspects and embodiments of the disclosure, directly packaged into a hydrogel particle. In some embodiments, nucleic acid is combined with one or more nucleic acid complexing agents. In some embodiments, the one or more nucleic acid complexing agents comprises a cationic polymer, cationic peptide, cationic lipid, a functional equivalent of any of the preceding, or mixtures thereof.

In some embodiments, the cationic polymer comprises linear and branched poly(ethyleneimine) (PEI), poly(beta-amino esters), Poly(2-(dimethylamino)ethyl methacrylate) (pDMEAMA); poly(amido amine) (PAMAM), chitosan, imine-containing polyamines, polyurethans, cyclodextrin, disulfide-containing poly(amido amine), a functional equivalent of any of the preceding, and mixtures thereof.

In some embodiments, the cationic peptide comprises one or more of KALA, GALA, MAP, LAH4, Melittin-derived peptide, p5RHH, poly(L-lysine) (PLL), poly(D-lysine) (PDL), poly(L-histidine), poly(D-histidine), protonatable amine-containing peptide, a functional equivalent of any of the preceding, and mixtures thereof.

In some embodiments, the cationic lipid comprises lipofectamine, DOSPA, DOPE, DSPE, DSTAP, DOTAP, DOTMA, DORIE, DMRIE, DOTIM, GAP-DLRIE, DDAB, DC-6-14, DODAP, DOTC, DOGS, a functional equivalent of any of the preceding, and mixtures thereof.

In some embodiments, the nucleic acid and the nucleic acid complexing agent are mixed at a N/P ratio, defined above. In some embodiments, the N/P ratio comprises between about 1 and 100, or between about 1 and 90, or between about 2 and 75, or between about 3 and 65, or between about 4 and 50. In some embodiments of the method, the nucleic acid is DNA and the complexing agent is PEI, the N/P ratio comprises between about 5 and 35, or between about 15 and 25, or about 20.

In some embodiments, the polyplexes further comprise a coating layer. In some embodiments, the coating layer can comprise one or more coating layer agents, which, in some embodiments, comprise one or more biocompatible polymers, one or more mineral salts, and mixtures thereof.

In some embodiments, the one or more biocompatible polymers comprise unmodified hyaluronic acid (HA), modified HA, alginate, PEGylated anionic peptides, poly (HEMA), poly(vinyl alcohol), poly sulfates, dextran, collagen, gelatin, chitosan, a functional equivalent of any of the preceding and mixtures thereof.

In some embodiments, the modified HA comprises HA-norbornene, HA-acrylamide, HA-tetrazine, HA-sulfate, HA-cyclodextrin, HA-adamantane, HA-vinyl sulfone, HA-acrylate, HA-allyl, HA-azide, HA-alkyne, HA-thiol, HA-PEG, a functional equivalent of any of the preceding and mixtures thereof.

In some embodiments, the one or more mineral salts comprise calcium carbonate, magnesium sulfate, calcium sulfate and mixtures thereof.

In some embodiments, the polymer is bound to one or more peptides comprising at least three consecutive amino acids from an extracellular matrix protein. In some embodiments, the peptide comprises an integrin binding peptide, and in some embodiments, comprises an RGD peptide. In some embodiments, the polymer is bound to peptides of two or more different sequences.

In some embodiments, the one or more nucleic acid complexing agents and one or more coating layer agents are mixed at a coating/complexing ratio. The coating/complexing ratio represents a weight/weight ratio. In some embodiments, the coating/complexing ratio comprises between about 0.1 and 100, or between about 0.5 and 75, or between about 0.5 and 50, or between about 1 and 40, or between about 1 and 30, or between about 1 and 25, or between about 1 and 20. In some embodiments, of the scaffold the nucleic acid comprises DNA, the nucleic acid complexing agent comprises PEI, the N/P ratio comprises between about 2 and 7, or between about 3 and 5, and the coating/complexing ratio comprises between about 1 and 8, or between about 2 and 6, or between about 2 and 5.

In some embodiments, the polyplexes comprise lyophilized polyplexes, and in some embodiments, further comprise a cryoprotectant. In some embodiments, the cryoprotectant comprises one or more of sucrose, trehalose, proline, lysine, lactose, lactosucrose, low melting point agarose, taurine, a functional equivalent of any of the preceding, and combinations thereof. In some embodiments, the cryoprotectant comprises sucrose, and in some embodiments the sucrose comprises between about 10 to 500 μg per μg of nucleic acid, or between about 20 to 400 μg per μg of nucleic acid, or between about 25 to 350 μg per μg of nucleic acid, or between about 30 to 300 μg per μg of nucleic acid, or between about 35 to 250 μg per μg of nucleic acid, or between about 40 to 200 μg per μg of nucleic acid.

In some embodiments, the nucleic acid comprises DNA, the nucleic acid complexing agent comprises PEI, the N/P ratio comprises between about 15 to 25, the cryoprotectant comprises sucrose at between about 60 to 110 μg per μg DNA.

In some embodiments, the concentration of the nucleic acid comprises between about 0.1 mg/ml nucleic acid and 20 mg/ml nucleic acid, or between about 0.2 mg/ml nucleic acid and 18 mg/ml nucleic acid, or between about 0.25 mg/ml nucleic acid and 16 mg/ml nucleic acid, or between about 0.3 mg/ml nucleic acid and 14 mg/ml nucleic acid, or between about 0.4 mg/ml nucleic acid and 12 mg/ml nucleic acid, or between about 0.5 mg/ml nucleic acid and 10 mg/ml nucleic acid, or between about 0.5 mg/ml nucleic acid and 8 mg/ml nucleic acid, or between about 0.5 mg/ml nucleic acid and 7 mg/ml nucleic acid, or between about 0.5 mg/ml nucleic acid and 6 mg/ml nucleic acid, or between about 0.5 mg/ml nucleic acid and 5 mg/ml nucleic acid, or between about 0.6 mg/ml nucleic acid and 6 mg/ml nucleic acid, or between about 0.7 mg/ml nucleic acid and 7 mg/ml nucleic acid, or between about 0.8 mg/ml nucleic acid and 8 mg/ml nucleic acid, or between about 0.9 mg/ml nucleic acid and 9 mg/ml nucleic acid, or between about 1 mg/ml nucleic acid and 10 mg/ml nucleic acid, or between about 1 mg/ml nucleic acid and 7.5 mg/ml nucleic acid, or between about 1 mg/ml nucleic acid and 5 mg/ml nucleic acid.

In some embodiments of the methods of this aspect of the disclosure, contacting a cell comprises all relevant methods of administration, e.g., topically, intravascularly, intravenously, injection, infusion, orally, enterally, rectally, pulmonarily, inhalation, nasally, topically, transdermally, buccally, sublingually, intravesically, intravitreally, intraperitoneally, vaginally, brain, intra-cerebroventricularly, intra-cerebrally, intrasynovially, intracutaneously, intraarticularly, intraarterially, intrathecally, perispinally, intra-spinally, parenterally, subcutaneously, intrastemally, intralesionally, intramuscularly, intravenously, intradermally, transmucosally, sublingually, and the like.

In some embodiments, the method comprises contacting a cell with an amount of one or more nucleic acids effective for nucleic acid therapy. In some embodiments, the method comprises contacting a cell with an amount of one or more nucleic acids effective for tissue engineering. In some embodiments, the method comprises contacting a cell with an amount of one or more nucleic acids effective for vaccine development.

Another aspect of the disclosure provides a method for making a scaffold according to some aspects and embodiments of the disclosure, comprising: (i.) combining the nucleic acid and the nucleic acid complexing agent at a N/P ratio to form one or more polyplexes; (ii.) combining the polyplexes with one or more coating layer agents to form a coating layer on the polyplexes; (iii.) mixing polyplexes comprising a coating layer with a hydrogel; (iv.) crosslinking the hydrogel-polyplex mixture to form a bulk hydrogel; (v.) fractionating the crosslinked hydrogel into two or more pieces to make hydrogel particles; and (vi.) combining the hydrogel particles to make a scaffold. In some embodiments, steps iii. and iv. occur simultaneously.

In some embodiments, fractionating comprises passing the crosslinked hydrogel through a sieve or mesh with an average pore size, which, in some embodiments, comprises between about 1 μm and 1000 μm, or between about 5 μm and 750 μm, or between about 10 μm and 500 μm, or between about 15 μm and 400 μm, or between about 20 μm and 300 μm, or between about 30 μm and 200 μm, or between about 40 μm and 150 μm, or between about 40 μm and 100 μm, or about 10 μm, or about 20 μm, or about 30 μm, or about 40 μm, or about 50 μm, or about 60 μm, or about 70 μm, or about 85 μm, or about 100 μm, as well as other suitable pore sizes. In some embodiments, the sieve or mesh comprises a cell strainer.

In some embodiments, scaffold comprises one or more particles that is devoid of nucleic acids, nucleic acid complexing agents and/or polyplexes, with the proviso that not all particles are devoid of nucleic acid, nucleic acid complexing agent and/or polyplexes. As in some other embodiments, for particles that originate from a bulk hydrogel and for particles that are discretely polymerized, some particles may comprise empty particles. Such particles are contemplated and useful for use along with loaded particles. In some embodiments of this aspect of the disclosure, empty and loaded particles can be organized, layered, placed and otherwise arranged in 2D and 3D space to accomplish different goals as described elsewhere herein. Thus, in some embodiments, the scaffold comprises particles of two or more types. One or more same or different nucleic acids can be delivered to or placed in contact with one or more cells and/or tissues to affect one or more biological targets.

In some embodiments, the method further comprises combining one or more hydrogel particles devoid of nucleic acid, nucleic acid complexing agent, and/or polyplexes with the hydrogel particles of step vi. to make a scaffold. In some embodiments, the method further comprises combining one or more hydrogel particles of a different type from those prepared according to this aspect of the disclosure with the hydrogel particles of step vi. to make a scaffold. In some embodiments, the different type comprises discretely polymerized particles. In some embodiments, the method further comprises combining a first batch of one or more hydrogel particles prepared according to this aspect of the disclosure with a second batch of one or more hydrogel particles also prepared according to this aspect of the disclosure, with the proviso that at least one of nucleic acid, nucleic acid complexing agent, coating layer agents, or hydrogel, is different between batch one and batch two.

In some embodiments, polyplexes are substantially evenly distributed throughout particles that originate from a bulk hydrogel, and in some embodiments, at least one particle comprises an irregular shape. In some embodiments, particles comprise regular and irregular shapes.

In some embodiments, the scaffold comprises one or more particles that comprise an irregular shape, which irregularly shaped particles comprise an average surface area that can range from between about 100 $\mu m^2$ and 1000000 $\mu m^2$, or between about 500 $\mu m^2$ and 500000 $\mu m^2$, or between about 1000 $\mu m^2$ and 250000 $\mu m^2$, or between about 2500 $\mu m^2$ and 100000 $\mu m2$, or between about 5000 $\mu m^2$ and 50000 $\mu m^2$, or between about 7500 $\mu m^2$ and 40000 $\mu m^2$, or between about 10000 $\mu m^2$ and 25000 $\mu m^2$.

In some embodiments, the irregularly shaped particles comprise shred particles. In some embodiments, two or more particles of any type of the disclosure are annealed together, wherein annealed together comprises covalent, electrostatic, hydrophobic and mechanical annealing. In some embodiments, non-annealed scaffolds of two or more particles are contemplated and useful for aspects and embodiments of the disclosure.

In some embodiments, nucleic acids comprise DNA and RNA. DNA comprises all forms of natural, synthetic, purified, isolated, recombinant, or combinations thereof, of deoxyribonucleic acid, e.g., plasmid DNA, ssDNA, dsDNA, cDNA and minicircle DNA. RNA comprises all forms of natural, synthetic, purified, isolated, recombinant, or combinations thereof, of ribonucleic acid, e.g., mRNA, pre-mRNA, siRNA, shRNA, ssRNA, antisense RNA oligonucleotide, antisense miRNA, trans-splicing RNA, guide RNA, single-guide RNA, crRNA, tracrRNA and trans-splicing RNA.

Naked nucleic acid can be used in aspects and embodiments of the disclosure, directly packaged into a hydrogel particle. In some embodiments, nucleic acid is combined with one or more nucleic acid complexing agents. In some embodiments, the one or more nucleic acid complexing agents comprises a cationic polymer, cationic peptide, cationic lipid, a functional equivalent of any of the preceding, or mixtures thereof.

In some embodiments, the cationic polymer comprises linear and branched poly(ethyleneimine) (PEI), poly(beta-amino esters), Poly(2-(dimethylamino)ethyl methacrylate) (pDMEAMA); poly(amido amine) (PAMAM), chitosan, imine-containing polyamines, polyurethans, cyclodextrin, disulfide-containing poly(amido amine), a functional equivalent of any of the preceding, and mixtures thereof.

In some embodiments, the cationic peptide comprises one or more of KALA, GALA, MAP, LAH4, Melittin-derived peptide, p5RHH, poly(L-lysine) (PLL), poly(D-lysine) (PDL), poly(L-histidine), poly(D-histidine), protonatable amine-containing peptide, a functional equivalent of any of the preceding, and mixtures thereof.

In some embodiments, the cationic lipid comprises lipofectamine, DOSPA, DOPE, DSPE, DSTAP, DOTAP, DOTMA, DORIE, DMRIE, DOTIM, GAP-DLRIE, DDAB, DC-6-14, DODAP, DOTC, DOGS, a functional equivalent of any of the preceding, and mixtures thereof.

In some embodiments, the nucleic acid and the nucleic acid complexing agent are mixed at a N/P ratio, defined above. In some embodiments, the N/P ratio comprises between about 1 and 100, or between about 1 and 90, or between about 2 and 75, or between about 3 and 65, or between about 4 and 50. In some embodiments of the structure for localized and controlled release of nucleic acids, the nucleic acid is DNA and the complexing agent is PEI, the N/P ratio comprises between about 5 and 35, or between about 15 and 25, or about 20.

In some embodiments, the polyplexes further comprise a coating layer. In some embodiments, the coating layer can comprise one or more coating layer agents, which, in some embodiments, comprise one or more biocompatible polymers, one or more mineral salts, and mixtures thereof.

In some embodiments, the one or more biocompatible polymers comprise unmodified hyaluronic acid (HA), modified HA, alginate, PEGylated anionic peptides, poly (HEMA), poly(vinyl alcohol), poly sulfates, dextran, collagen, gelatin, chitosan, a functional equivalent of any of the preceding and mixtures thereof.

In some embodiments, the modified HA comprises HA-norbornene, HA-acrylamide, HA-tetrazine, HA-sulfate, HA-cyclodextrin, HA-adamantane, HA-vinyl sulfone, HA-acrylate, HA-allyl, HA-azide, HA-alkyne, HA-thiol, HA-PEG, a functional equivalent of any of the preceding and mixtures thereof.

In some embodiments, the one or more mineral salts comprise calcium carbonate, magnesium sulfate, calcium sulfate and mixtures thereof.

In some embodiments, the polymer is bound to one or more peptides comprising at least three consecutive amino acids from an extracellular matrix protein. In some embodiments, the peptide comprises an integrin binding peptide, and in some embodiments, comprises an RGD peptide. In some embodiments, the polymer is bound to peptides of two or more different sequences.

In some embodiments, the one or more nucleic acid complexing agents and one or more coating layer agents are mixed at a coating/complexing ratio. The coating/complexing ratio represents a weight/weight ratio. In some embodiments, the coating/complexing ratio comprises between about 0.1 and 100, or between about 0.5 and 75, or between about 0.5 and 50, or between about 1 and 40, or between about 1 and 30, or between about 1 and 25, or between about 1 and 20. In some embodiments, of the scaffold the nucleic acid comprises DNA, the nucleic acid complexing agent comprises PEI, the N/P ratio comprises between about 2 and 7, or between about 3 and 5, and the coating/complexing ratio comprises between about 1 and 8, or between about 2 and 6, or between about 2 and 5.

In some embodiments, the polyplexes comprise lyophilized polyplexes, and in some embodiments, further comprise a cryoprotectant. In some embodiments, the cryoprotectant comprises one or more of sucrose, trehalose, proline, lysine, lactose, lactosucrose, low melting point agarose, taurine, a functional equivalent of any of the preceding, and combinations thereof. In some embodiments, the cryoprotectant comprises sucrose, and in some embodiments the sucrose comprises between about 10 to 500 µg per µg of nucleic acid, or between about 20 to 400 µg per µg of nucleic acid, or between about 25 to 350 µg per µg of nucleic acid, or between about 30 to 300 µg per µg of nucleic acid, or between about 35 to 250 µg per µg of nucleic acid, or between about 40 to 200 µg per µg of nucleic acid.

In some embodiments, the nucleic acid comprises DNA, the nucleic acid complexing agent comprises PEI, the N/P ratio comprises between about 15 to 25, the cryoprotectant comprises sucrose at between about 60 to 110 µg per µg DNA.

In some embodiments, the concentration of the nucleic acid comprises between about 0.1 mg/ml nucleic acid and 20 mg/ml nucleic acid, or between about 0.2 mg/ml nucleic acid and 18 mg/ml nucleic acid, or between about 0.25 mg/ml nucleic acid and 16 mg/ml nucleic acid, or between about 0.3 mg/ml nucleic acid and 14 mg/ml nucleic acid, or between about 0.4 mg/ml nucleic acid and 12 mg/ml nucleic acid, or between about 0.5 mg/ml nucleic acid and 10 mg/ml nucleic acid, or between about 0.5 mg/ml nucleic acid and 8 mg/ml nucleic acid, or between about 0.5 mg/ml nucleic acid and 7 mg/ml nucleic acid, or between about 0.5 mg/ml nucleic acid and 6 mg/ml nucleic acid, or between about 0.5 mg/ml nucleic acid and 5 mg/ml nucleic acid, or between about 0.6 mg/ml nucleic acid and 6 mg/ml nucleic acid, or between about 0.7 mg/ml nucleic acid and 7 mg/ml nucleic acid, or between about 0.8 mg/ml nucleic acid and 8 mg/ml nucleic acid, or between about 0.9 mg/ml nucleic acid and 9 mg/ml nucleic acid, or between about 1 mg/ml nucleic acid and 10 mg/ml nucleic acid, or between about 1 mg/ml nucleic acid and 7.5 mg/ml nucleic acid, or between about 1 mg/ml nucleic acid and 5 mg/ml nucleic acid.

The compositions, systems, and methods provided herein will improve non-viral nucleic acid delivery to enhance transfection and tissue repair in vivo.

The following Examples are provided by way of illustration and not by way of limitation.

EXAMPLES

Figure 1:
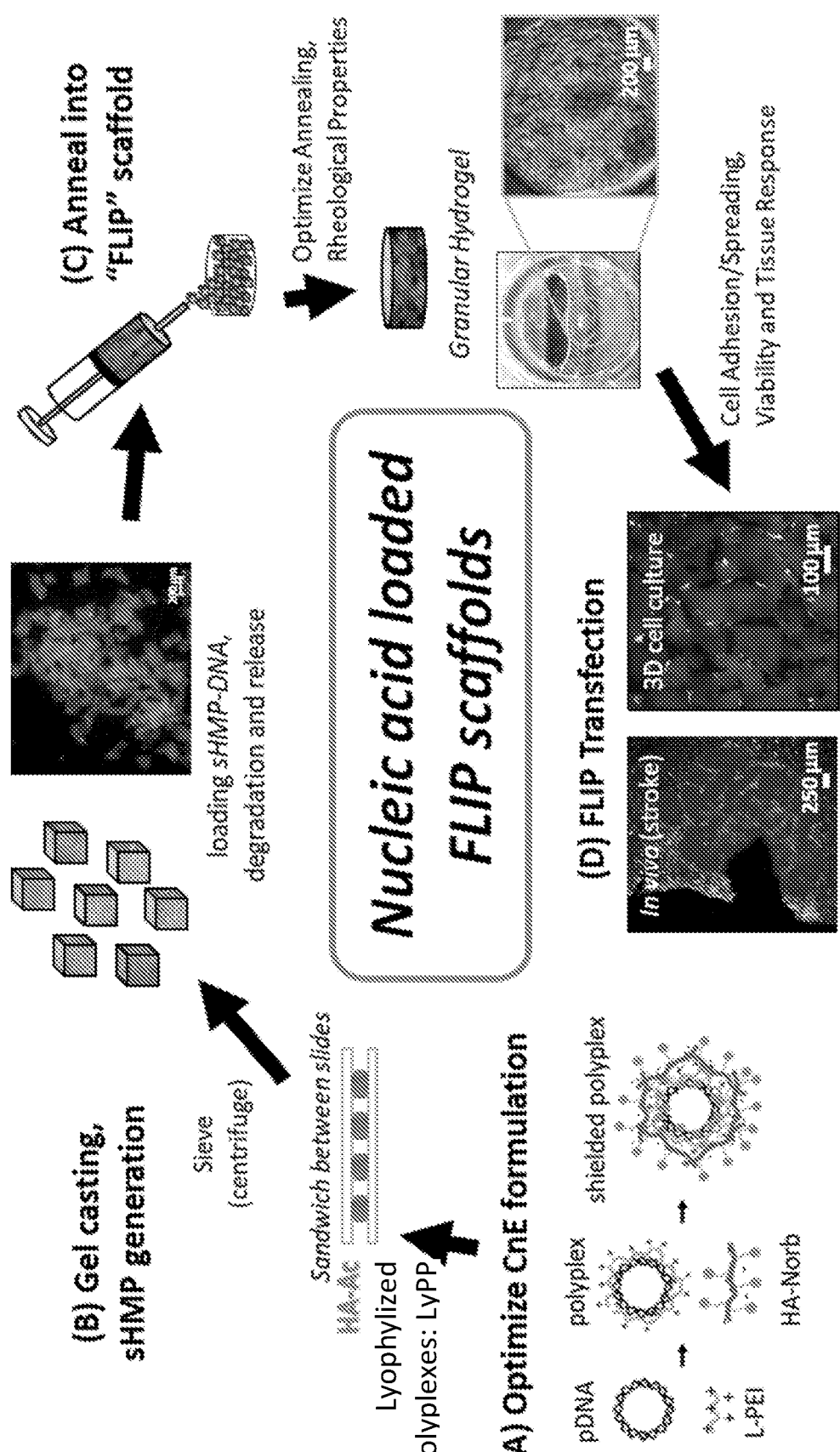
FIG. 1 shows a schematic showing Shred Hydrogel Microparticle (sHMP-DNA) technology for gene delivery in accordance with one embodiment of the disclosure.
Figure 2A:
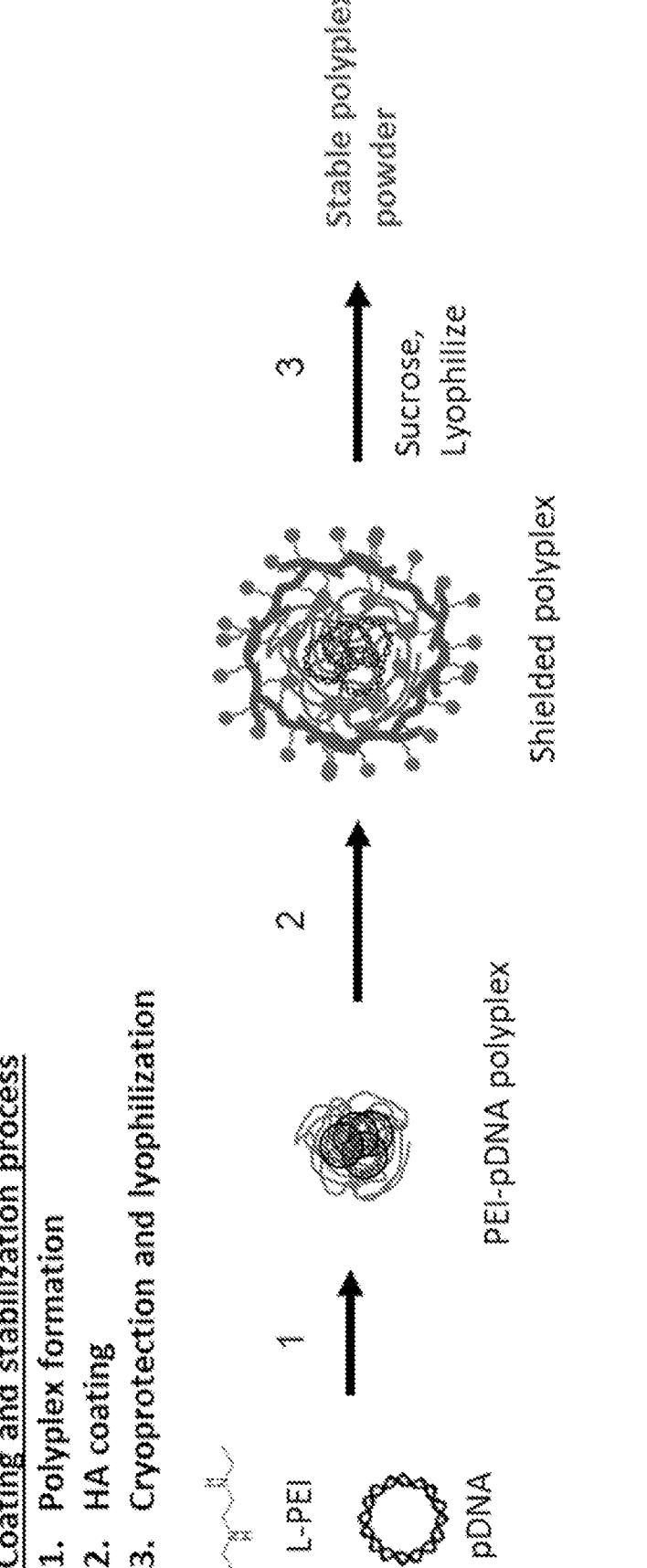
(FIG. 2A) Polyplexes are formed through mixing DNA/PEI and subsequently coated, as non-limiting examples, with unmodified or modified HA (FIG. 2B).
Figure 2B:
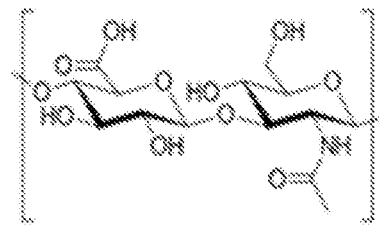
FIG. 2 is a coating strategy overview.
Figure 2B:
Figure 2B:
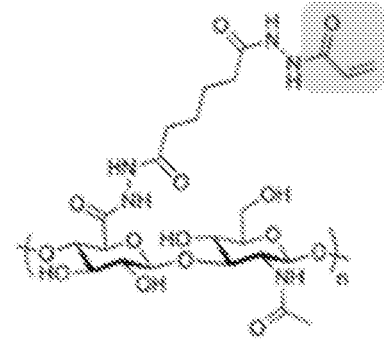
Figure 2B:
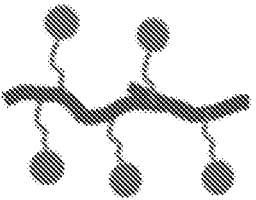
Figure 2B:
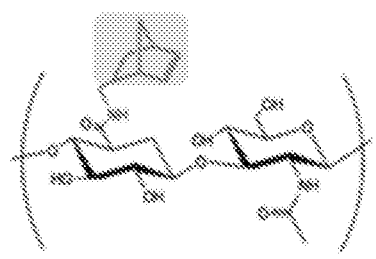
Figure 2B:

One aspect of the therapeutic polymer gel for example for use in a surgical or wound site includes a collection of irregularly shaped microgel particles that are loaded with nucleic acid nanoparticles (polyplexes), which are then used to locally deliver nucleic acids. The nucleic acids are meant to either increase the expression of a desired gene or suppress the expression of a desired gene. Thus, the nucleic acid can comprise any nucleic acid, including plasmid DNA, minicircle DNA, mRNA, siRNA, miRNA, CRISPR-Cas9. Schematic, FIG. 1.

Incorporation of nucleic acids into hydrogel scaffolds can be done through introducing the naked component (without the addition of additional additives) or in the form of nanosized particles/aggregates. The use of nucleic acid nanosized particles/aggregates is beneficial as it can increase the stability of the nucleic acid, increasing its half-life, the efficiency of nucleic acid delivery into cells, achieving higher biological effect, and control the location and release rate of the nanosized particles/aggregates. The formation of nanosized particles/aggregates involves the complexation of the nucleic acid with a positively charged polymer. These nanosized particles/aggregates, also referred to as "poly-plexes", are unstable at high concentration due to their charge resulting in aggregation and inactivation. When attempting to incorporate these polyplexes into hydrogel scaffolds aggregation occurs readily. To prevent aggregation, the present disclosure provides for the coating of polyplexes with polymers to shield the charge of the polyplex [FIG. 2]. The coating here is done with hyaluronic acid (HA), which can be chemically modified (for example to contain acrylate or norbornene groups), and other coatings are suitable as described herein. The presence of HA coating prevents aggregation in solution and increases stability of high concentration DNA solutions.

Coating, Stability, and Transfection Prior to Hydrogel Insertion

Figures 3A, 3B, 3C, 3D:
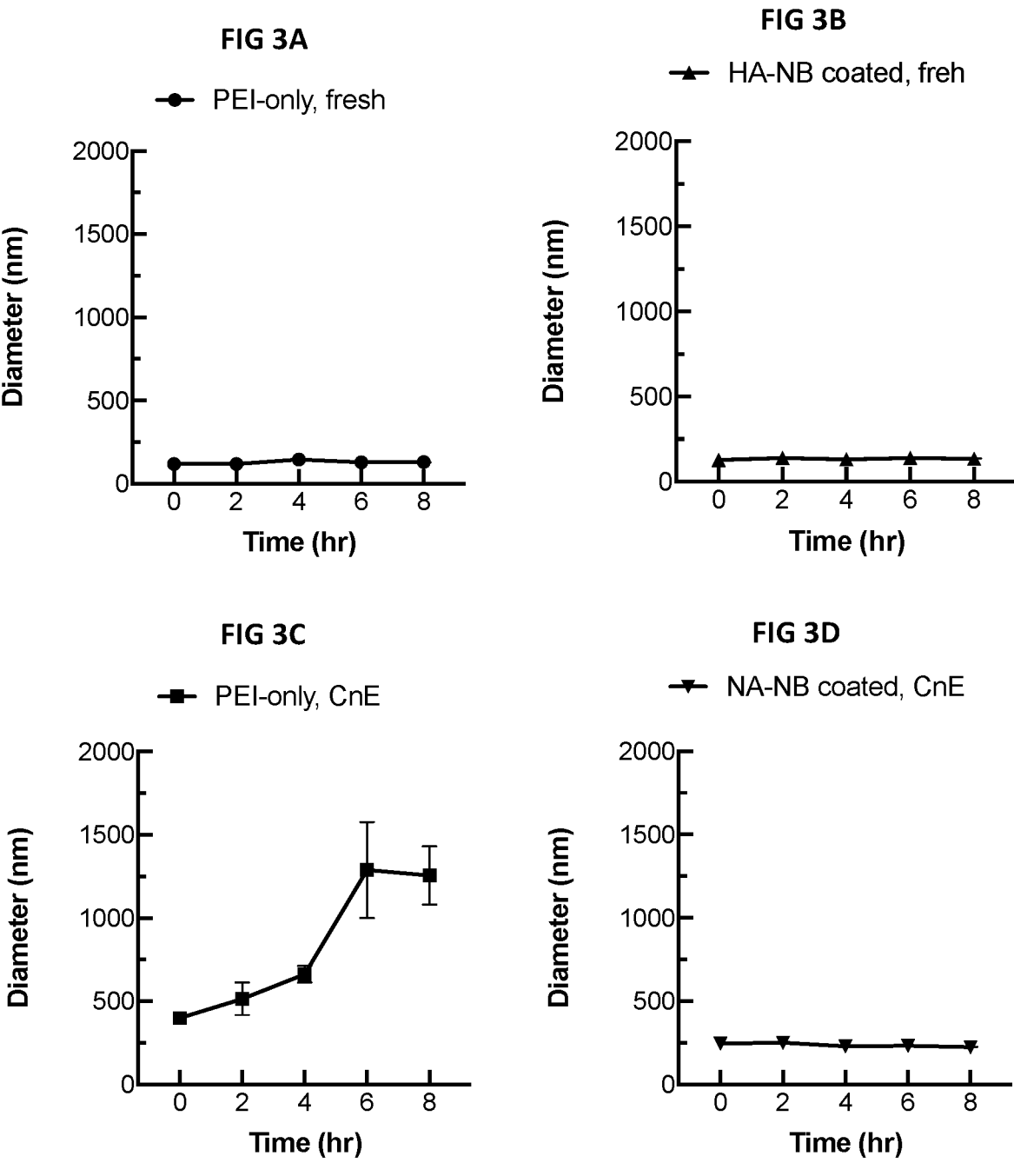
FIG. 3 shows aggregation stability of DNA/PEI polyplexes (N/P of 20, 1 μg/100 μL). Prior to lyophilization DNA/PEI polyplexes are stable in a 150 mM NaCl solution for up to 8 hours (FIG. 3A). Coating with HA-NB does not affect stability (FIG. 3B). Lyophilization of DNA/PEI with the cryoprotectant sucrose does not generate stable particles after resuspension in 150 mM NaCl (FIG. 3C). In contrast, lyophilization of coated DNA/PEI polyplexes with the cryoprotectant sucrose results in stable particles with no aggregation for 8 hours (FIG. 3D).
Figure 4A:
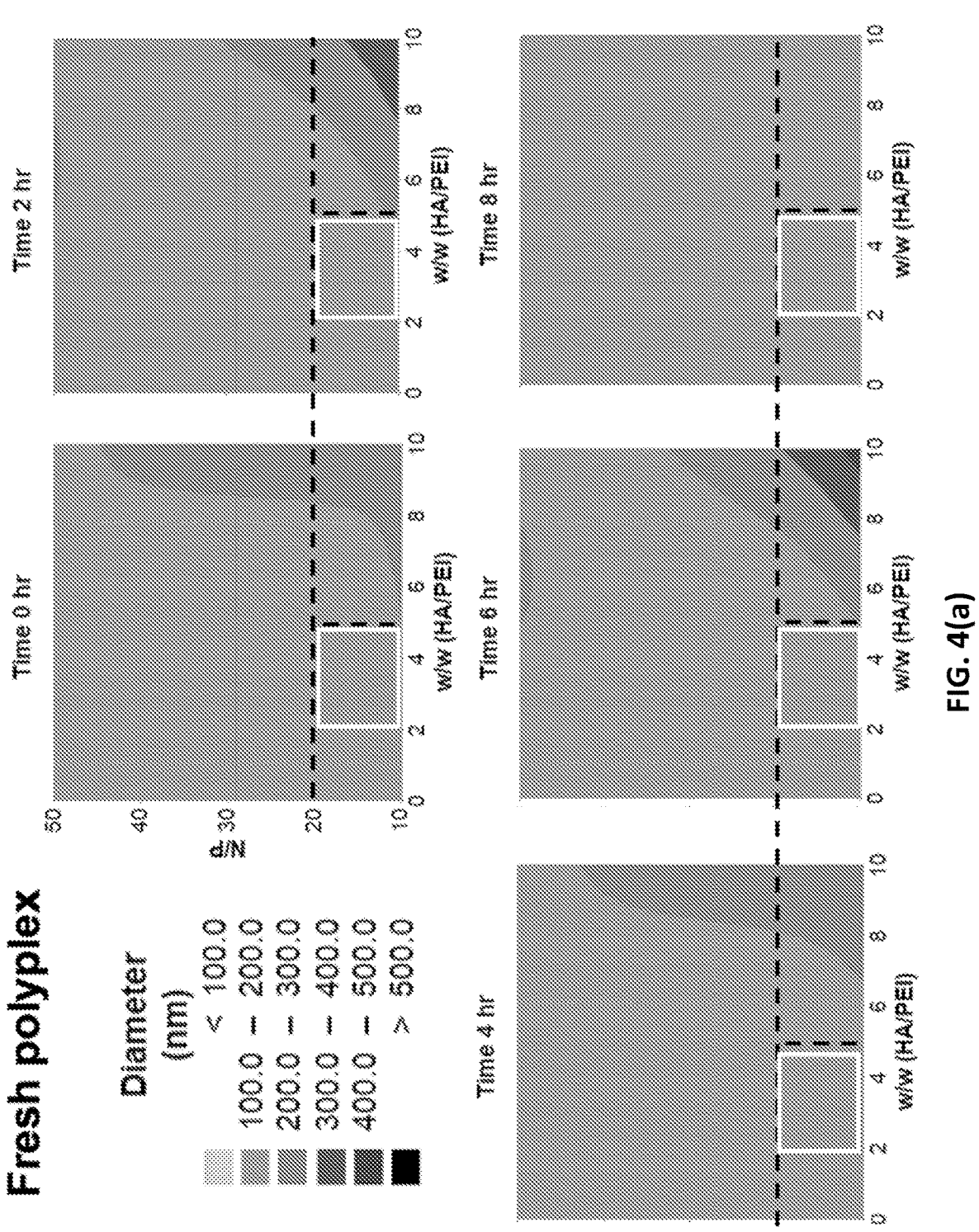
FIG. 4A represents fresh polyplexes.
Figure 4B:
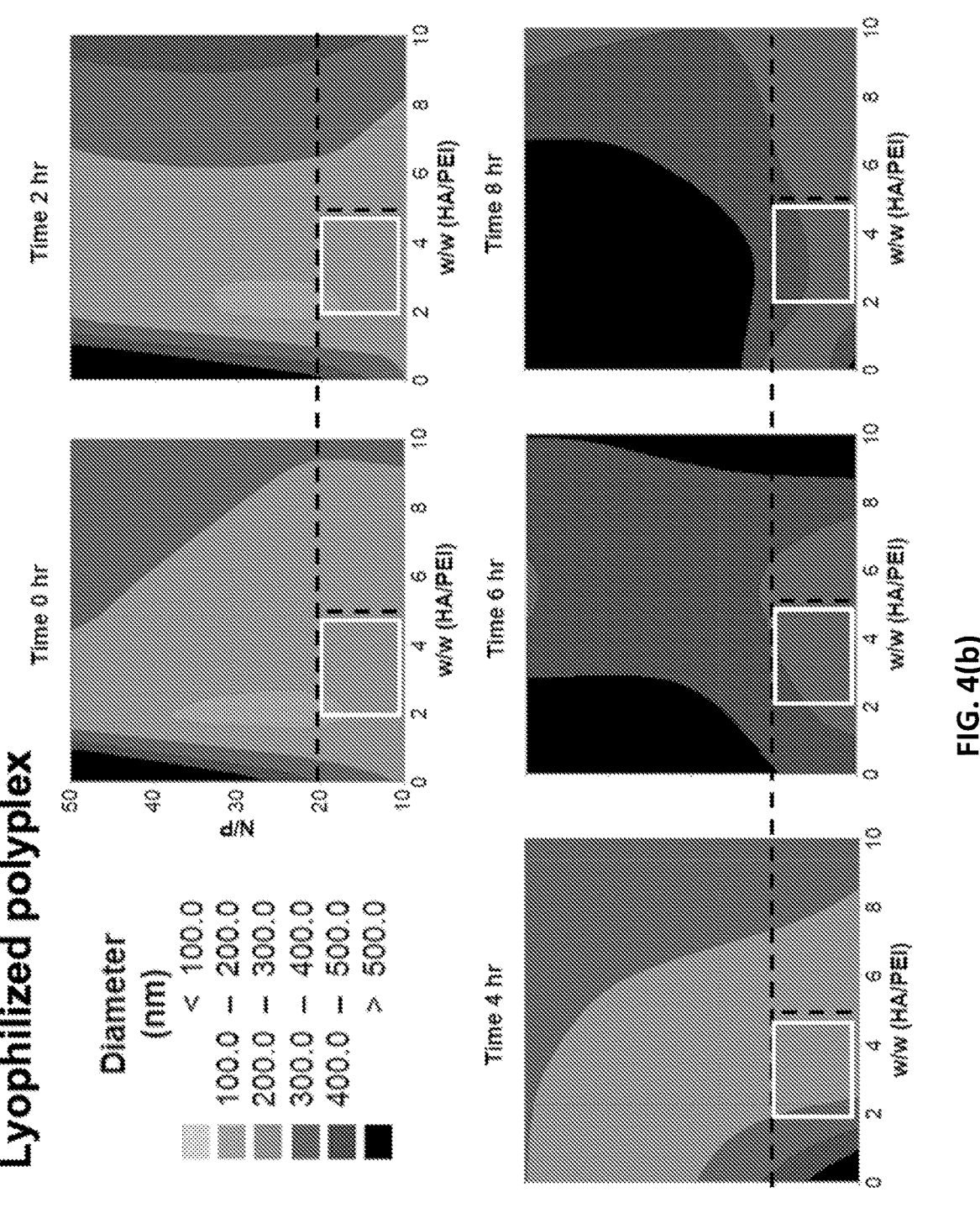
FIG. 4B represents lyophilized polyplexes ("LyPP").

For in vivo transfection, doses of DNA are generally in the 0.1-1.0 mg/kg for IV administration, depending on the complexing agent used (such as linear polyethylenimine) and toxicity, and 0.5-5.0 mg/kg for local delivery, such as intramuscular injection. Thus, concentrations above 0.5 mg/mL within hydrogels are desirable. However, past developments in hydrogel-mediated gene transfer have been limited to 0.02-0.1 mg/mL due to the aggregation of nanoparticles within the material. To achieve this concentration, either polyplexes must be generated at the desired high concentration or first formed a low concentration and subsequently concentrated. Lyophilization, a method to sublime a solution directly from a solution into a powder of solids, can be used to generate a solid that contains the nucleic acid material that can be re-dissolved in a reduced volume to achieve the desired higher concentration. However, direct lyophilization of polyplexes again results in aggregation. But we discovered lyophilization of polyplexes that have been coated with HA, in the presence of sucrose as a cryoprotectant, effectively prevents polyplex aggregation (via dynamic light scattering (DLS) and electrophoretic light scattering (ELS)) and retains polyplex activity (i.e., the ability to transfect cells) after lyophilization. While sucrose alone can cryoprotect polyplexes, it cannot successfully maintain polyplex stability long term (as aggregation occurs in solution). Only polyplexes that have been coated with hyaluronic acid and lyophilized in the presence of sucrose are stable in solution (no aggregation by DLS). See FIGS. 3 and 4, for example. The cationic polymer (for example, polyethylenimine) to DNA ratio (N/P) is a parameter that can be varied between 5-50, in order to balance transfection efficiency with cytotoxicity. For polyplex stabilization, the stabilizing HA polymer to complexing agent (w/w ratio) can also be optimized for nanoparticle stability, size, and charge. Lastly, the stabilizing HA can be chemically modified, for example with acrylates (Ac) or norbornenes (NB), or used unmodified. However, the ratio of stabilizing HA to complexing agent depends on the size and degree of modification of the stabilizing HA, in addition to the complexing agent used. For linear polyethylenimine (25 kDa), an N/P range of 10-50 and HA/PEI ratios of 0-10 for the previously mentioned modifications (or lack of) were explored for nanoparticle properties.

Figure 5:
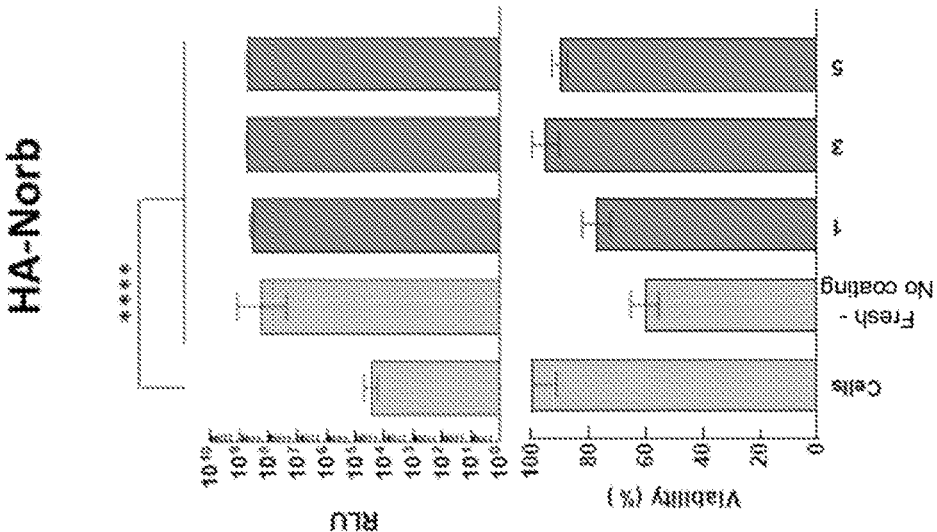
FIG. 5 shows lyophilized coated polyplexes transfect mouse mesenchymal stem cells similarly to freshly made DNA/PEI polyplexes (PEI-only). Cells represents background. w/w HA/PEI represents different coating ratios by weight and are all samples that have been lyophilized and resuspended in 150 mM NaCl. n=3, with one-way ANOVA and Tukey's HSD (p<0.01). Unmodified HA and HA modified with norbornene groups (HA-Norb) achieved similar levels of transfection for all coating ratios, but HA-NB gave better viability outcomes at the best performing ratios. However, HA-acrylate (HA-Ac) required higher weight ratios to achieve efficient transfection, despite being largely non-toxic. Even at the best ratio for HA-Ac, it was significantly worse than the fresh PEI polyplex control.
Figure 5:
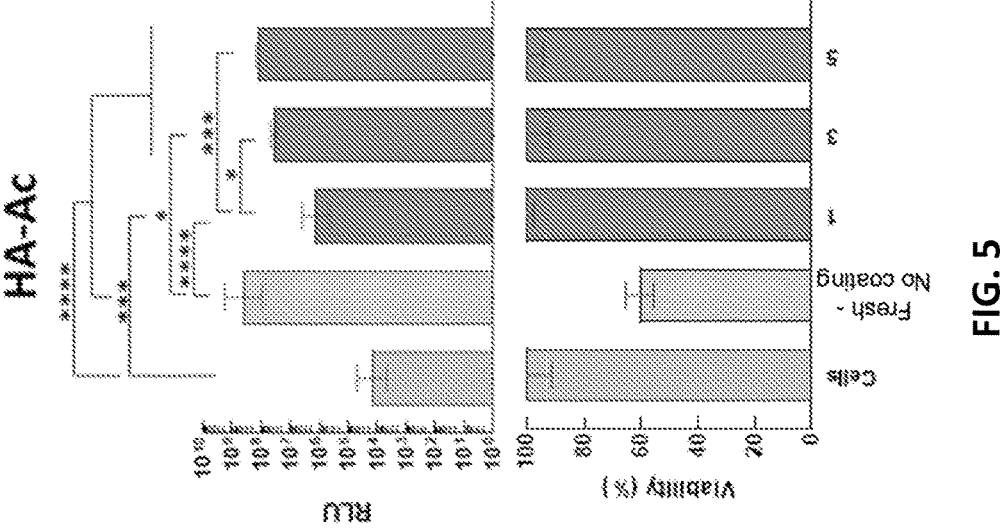
Figure 5:
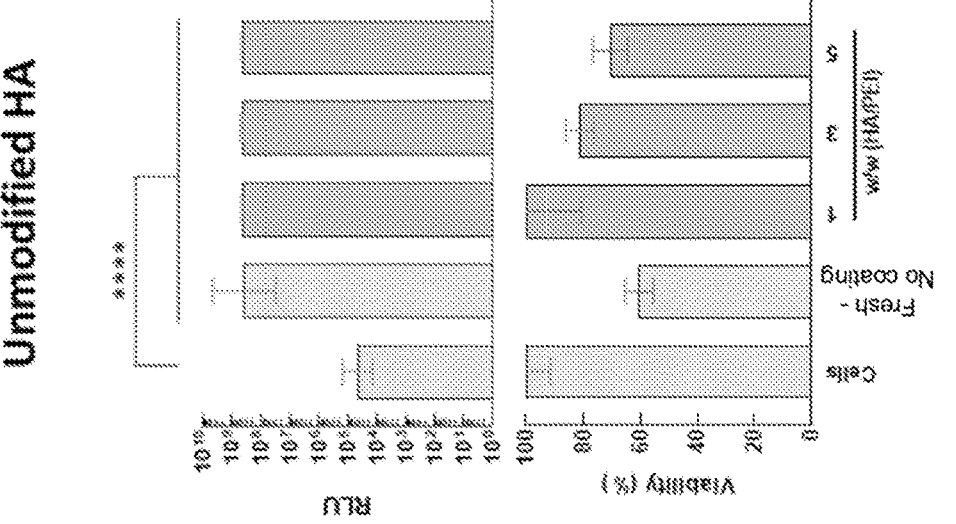

At a N/P of 20, HA/PEI ratios of 2-5 proved acceptable for stable, small (<300 nm) particles that had a slightly cation charge suitable for transfection. Lyophilized polyplexes are able to transfect cells (primary and cell lines) with similar efficiencies as freshly produced polyplexes that were not lyophilized. Polyplexes that were not coated prior to lyophilization resulted in poor or no transfection. In addition, coating and lyophilization results in significantly lower toxicity compared to freshly made uncoated polyplexes, allowing for higher amounts of nucleic acid to be delivered into cells without adverse effects. See data in FIG. 5 for example. Balancing transfection efficiency with viability, HA-NB at an HA/PEI ratio of 3-5 gave the best result in mouse mesenchymal stem cells, and consistent across other cell lines when testing the particular coating. This can also be extended to many different therapeutic vectors, from plasmid DNA, minicircles, and mRNA, although each requires separate optimization of the N/P ratio, based on the vector size and properties.

Flowable Linked Irregular Particle (FLIP) Scaffolds

Figure 6A:
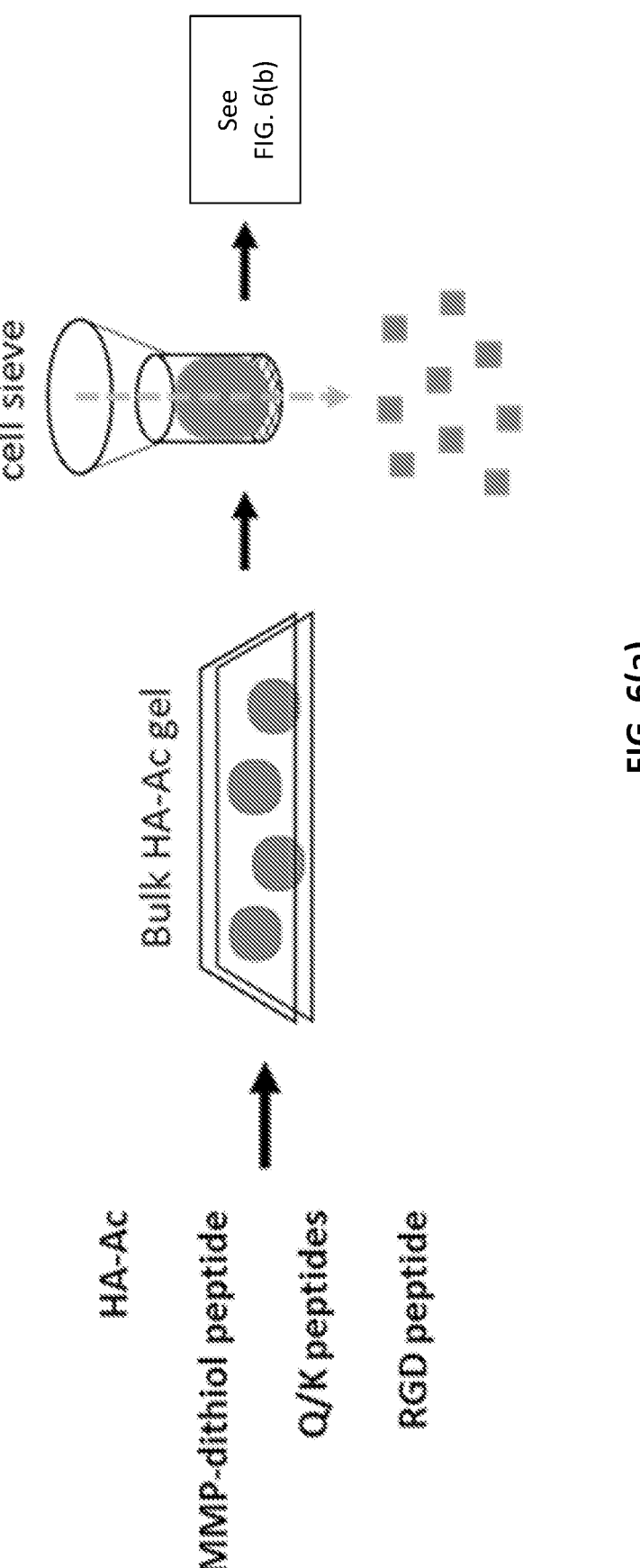
FIG. 6 shows FLIP (Flowable Linked Irregular Particle) scaffold formation. Formation of sHMP (shred hydrogel microparticles) by centrifuging bulk gel disks on a cell sieve mesh at various mesh size (40 μm, 70 μm, and 100 μm pore size). The resulting irregular sHMP distribution was quantified based on surface area from confocal microscopy to generate distributions. 70 μm sieve was selected as the standard due to similar surface area with past spherical MAP microgels.
Figure 6B:
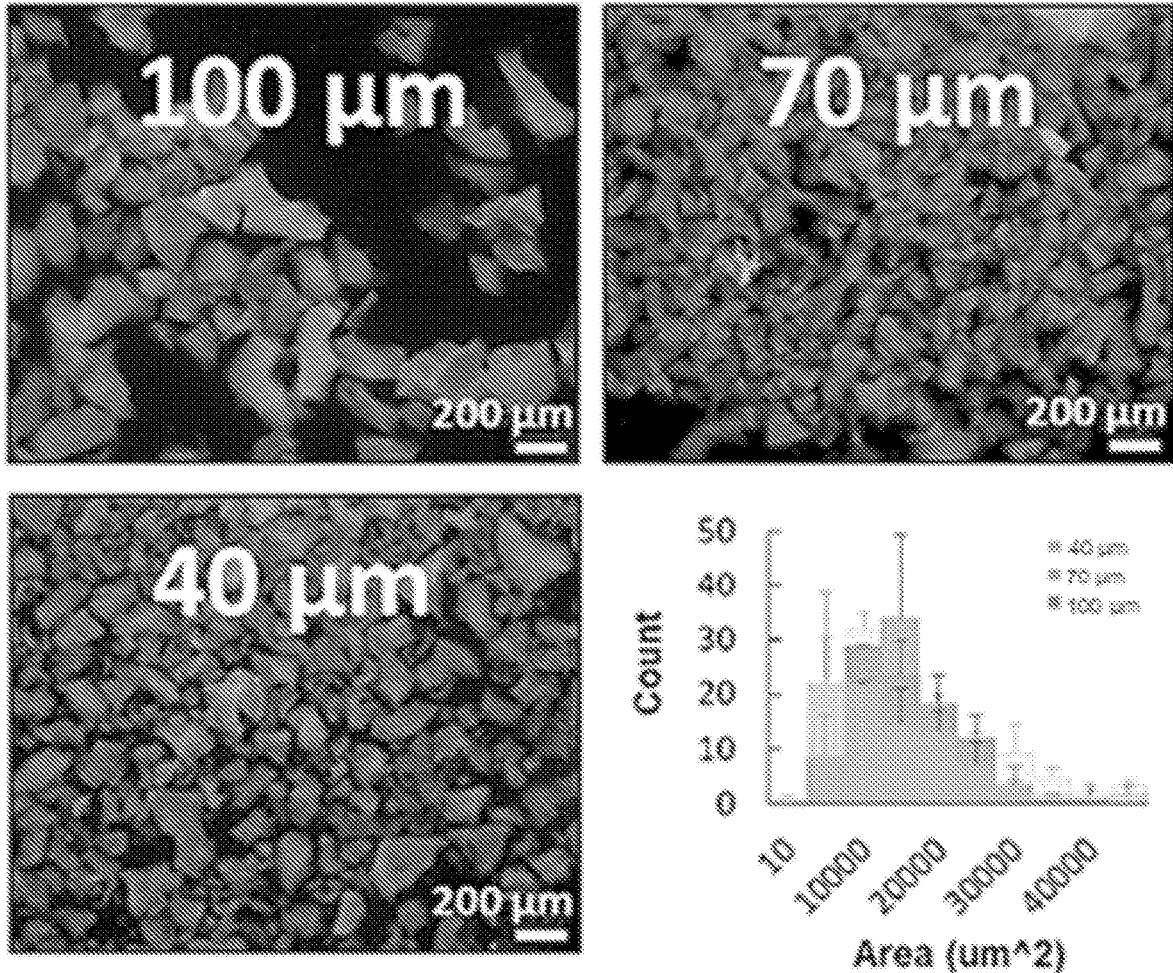

The therapeutic polymer gel system includes a collection of substantially irregularly shaped microgels having, in some embodiments, a long dimension about 10 μm to 1,000 μm and including a synthetic polymer backbone and annealing components. The irregularly shaped particles are generated by first forming a bulk hydrogel then passing this hydrogel through a sieving filter with mean pore size of 40 to 70 μm which yield irregular microgels between 10,000 to 25,000 μm² surface area [see FIG. 6]. These irregular particles can be annealed together to generate a stable porous hydrogel scaffold. The annealing component can be, e.g., enzymatic or chemical and result in covalent or non-covalent bonds that link the irregularly shaped microgels together. The resulting hydrogel scaffolds exhibit a stiffness between 10 to 10,000 pascals (Pa). The porosity of the resulting hydrogel material changes with the size of the building blocks from 0.136±0.73 void fraction when determined with a labeled dextran solution and confocal imaging. Although the material is porous, the pores are not completely interconnected nor are predetermined from the geometry of the particles. Because the particles are irregularly shaped and are soft, the particles can pack in a way that may not form a pore. However, porosity can be tuned by mixing different ratios of microgels at different sizes and stiffness. [see data in FIG. 7 for example].

The therapeutic polymer system comprising irregularly shaped microgel particles is a flowable system meaning it is injectable by means of a syringe, pipette, spreader, etc. The system remains a liquid until crosslinking with an annealing agent. Thus, this hydrogel is a flowable linked, irregular particle scaffold or FLIP scaffold for short. While the system is in the flowable state, cells can be mixed within the system without loss of viability. Upon addition of the annealing agent, the cells are entrapped within the porous gel structure. Both entrapped and topical seeded cells are able to infiltrate the scaffold, spread, proliferate and remain viable, consistent with the notion that the material is non-toxic. See FIG. 8.

Nucleic Acid Loading

Figure 9A:
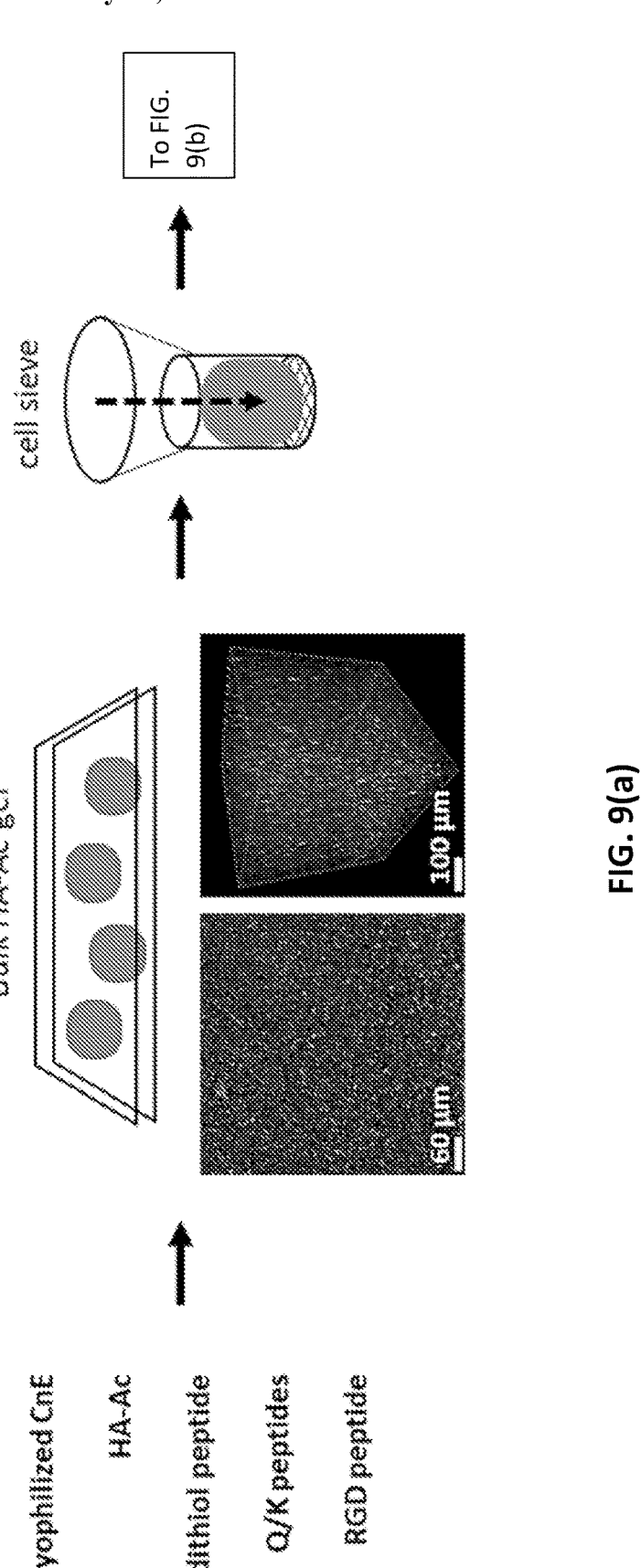
FIG. 9 shows nucleic acid incorporation into FLIP scaffolds. FLIP=flowable linked irregular particles, sHMP=shredded hydrogel microparticles
Figure 9B:
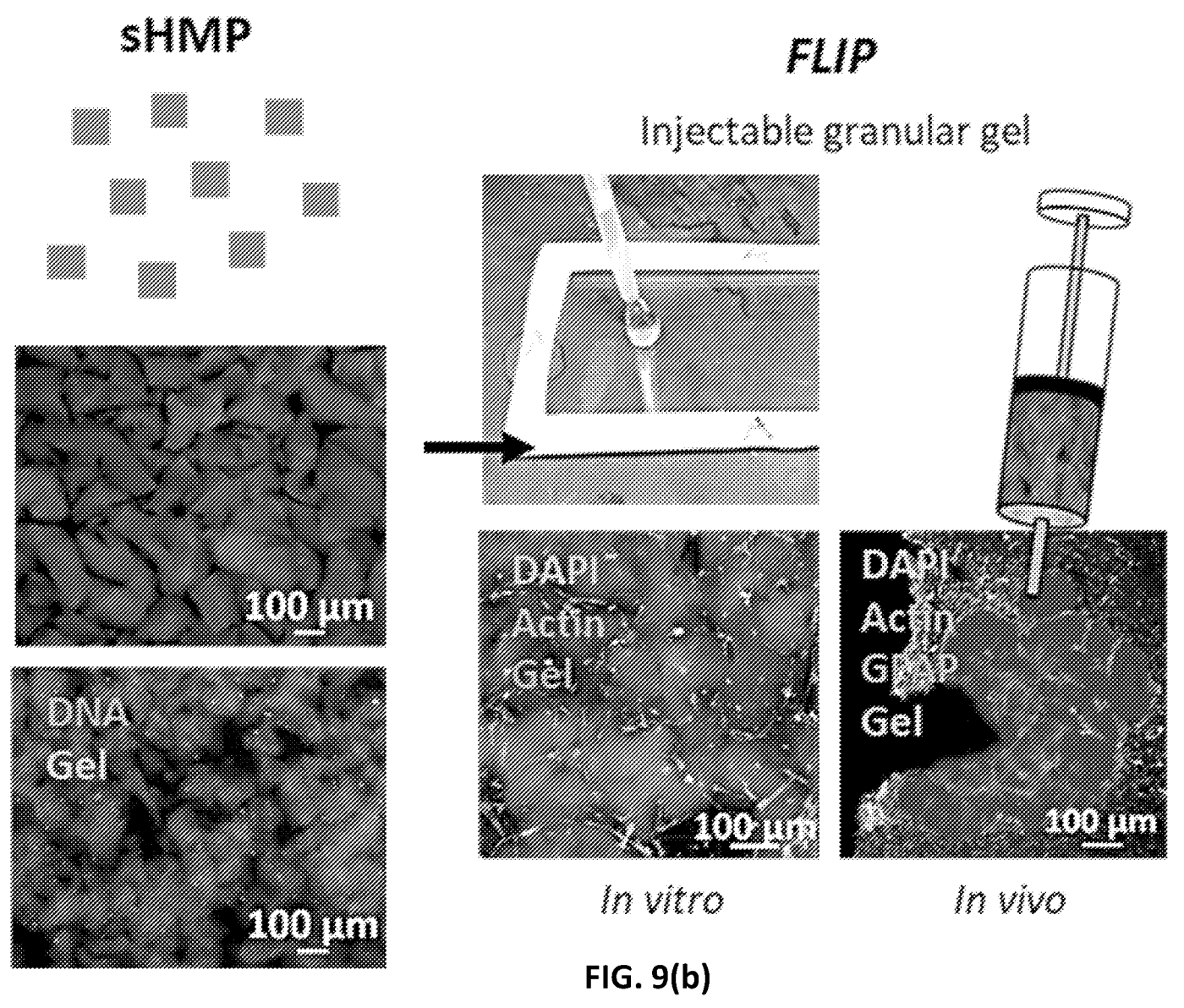
Figures 10A, 10B, 10C:
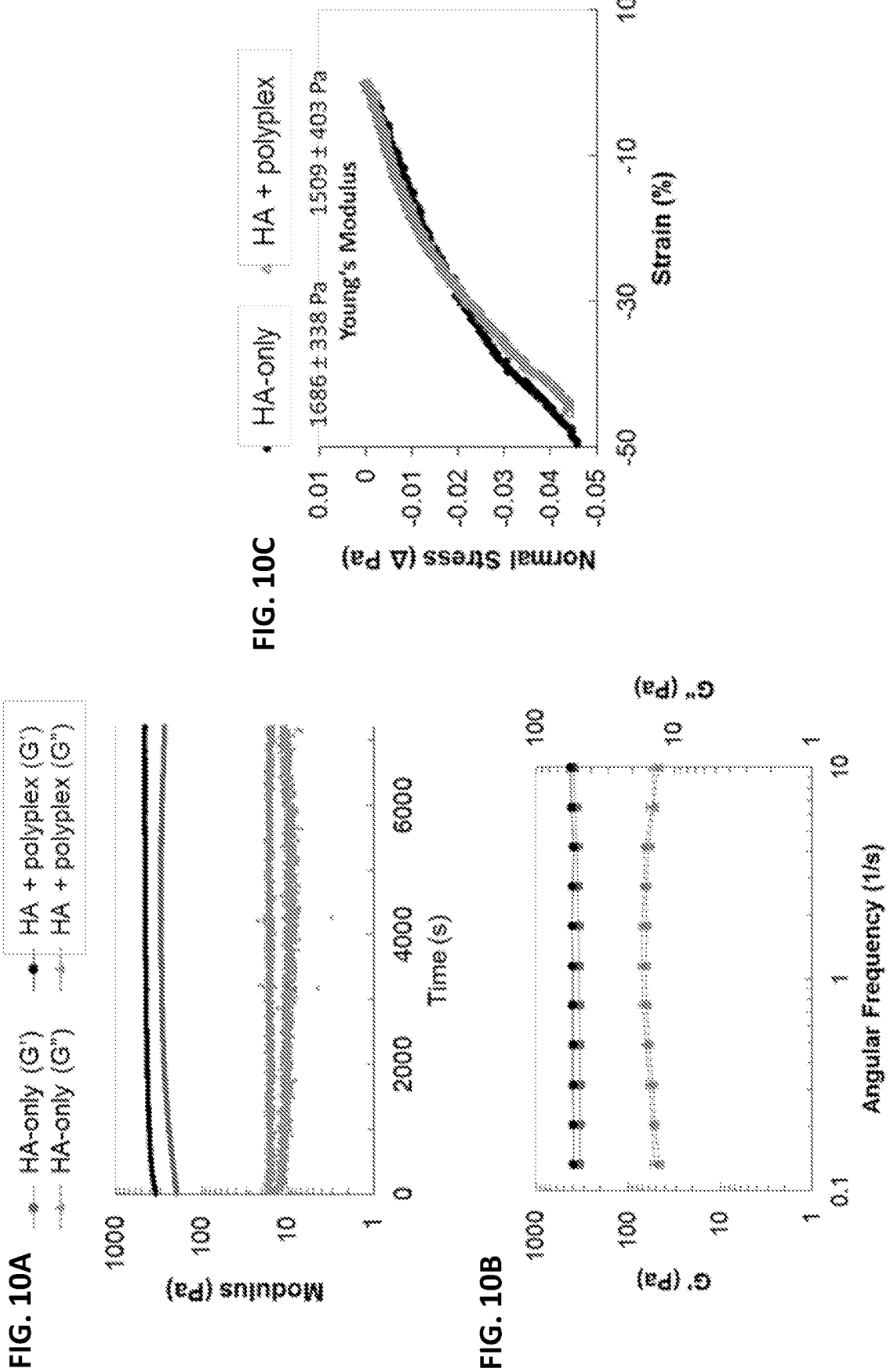
(FIG. 10A) Jamming study to obverse annealing time from Q/K peptides.
(FIG. 10B) Shear rheology on annealed gels following 1 hour incubation at 37° C. to derive the storage (G') and loss (G") moduli.
(FIG. 10C) Comparison of loaded and non-loaded annealed gels for Young's modulus from microstrain testing.
Figure 11A:
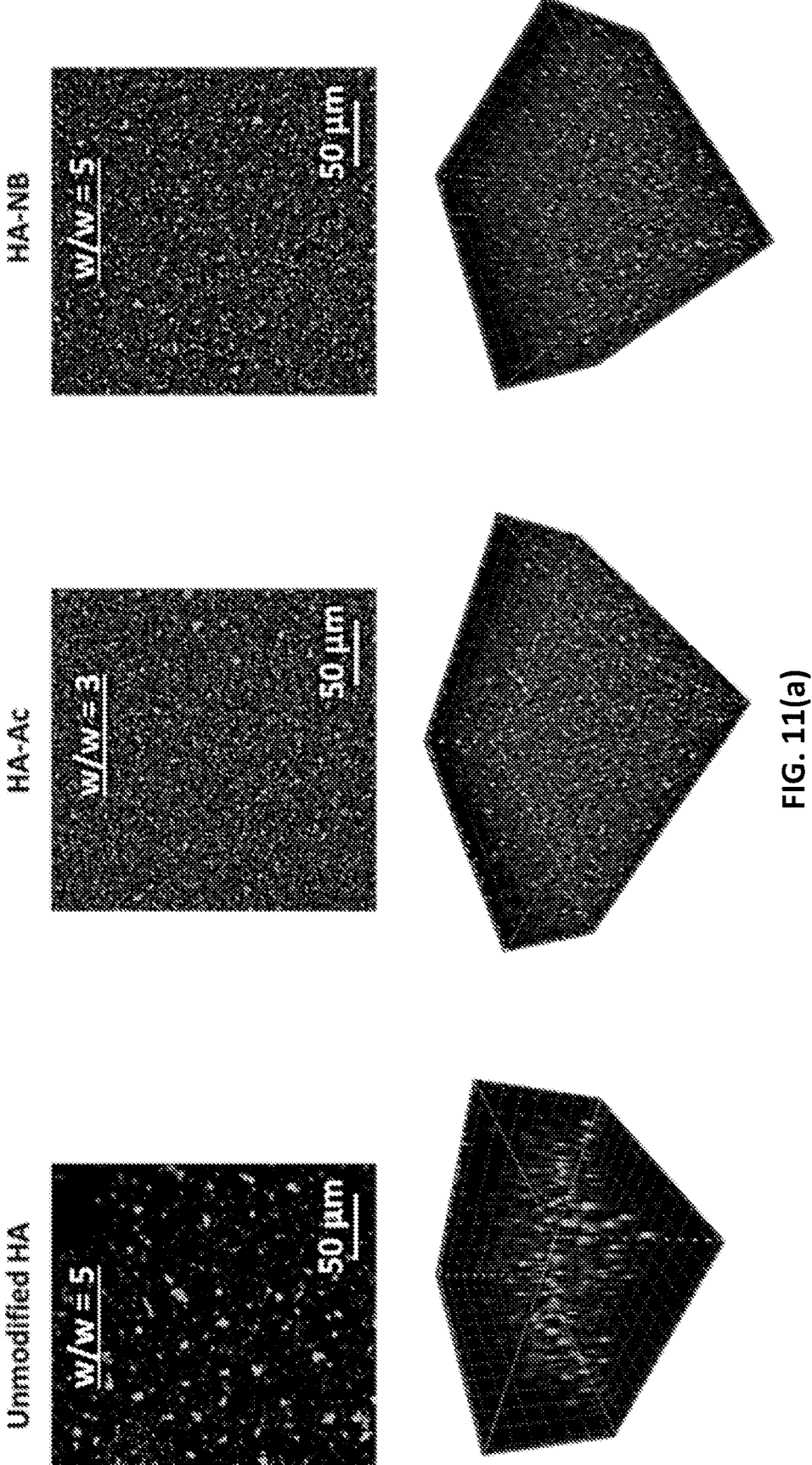
(FIG. 11A) Comparison of HA coatings, with unmodified HA, HA-Ac, and HA-NB for their top performing condition from 2D transfection studies.
Figure 11B:
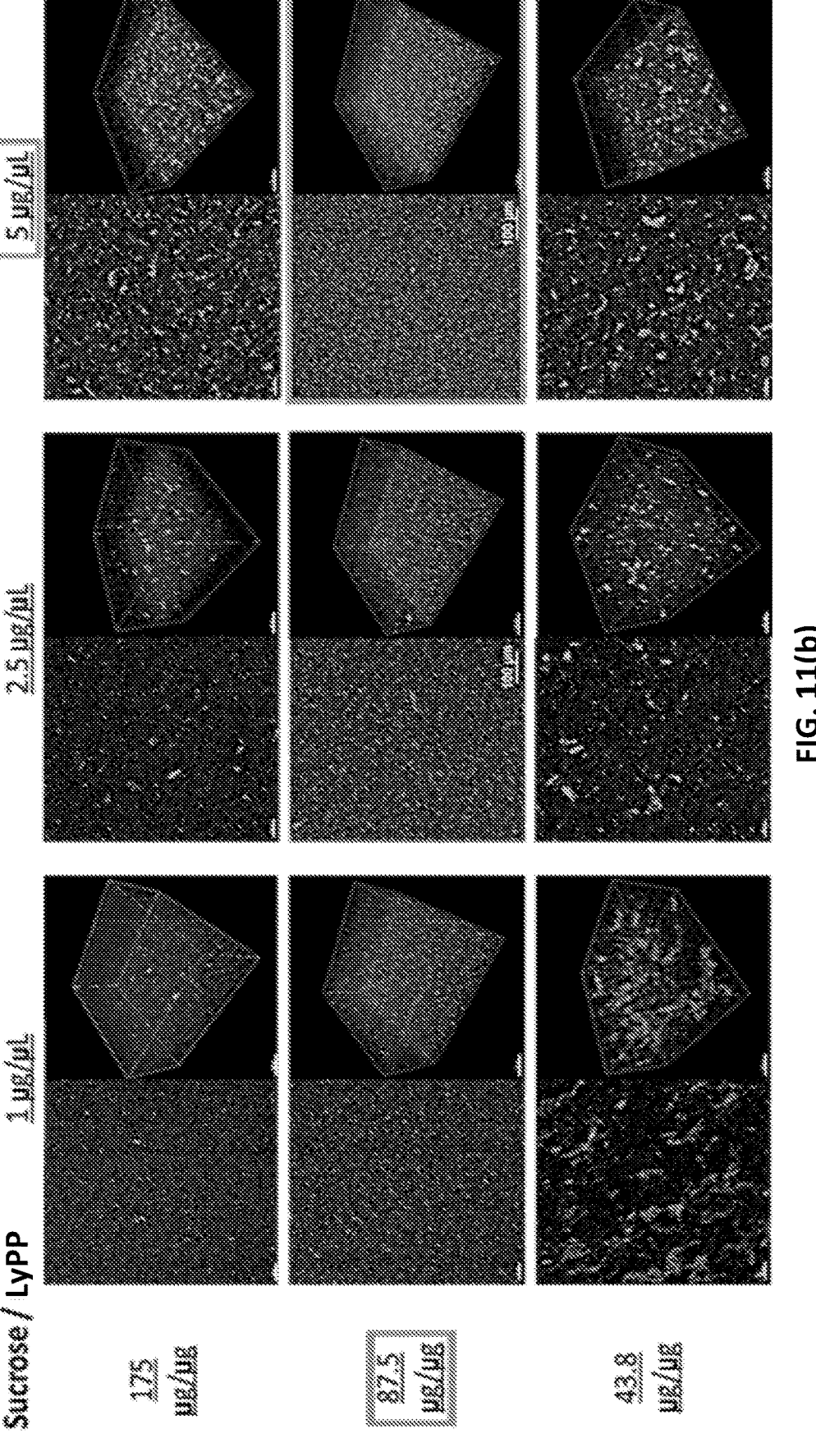
(FIG. 11B) Further optimization of HA-NB coated polyplexes by altering the sucrose concentration to balance precursor solution viscosity and aggregation within the HA-Ac material with increased polyplex loading. 5 μg lyophilized polyplex per μL of hydrogel, and 87.5 μg sucrose per μg DNA produced favorable conditions with minimal aggregates.
Figure 12:
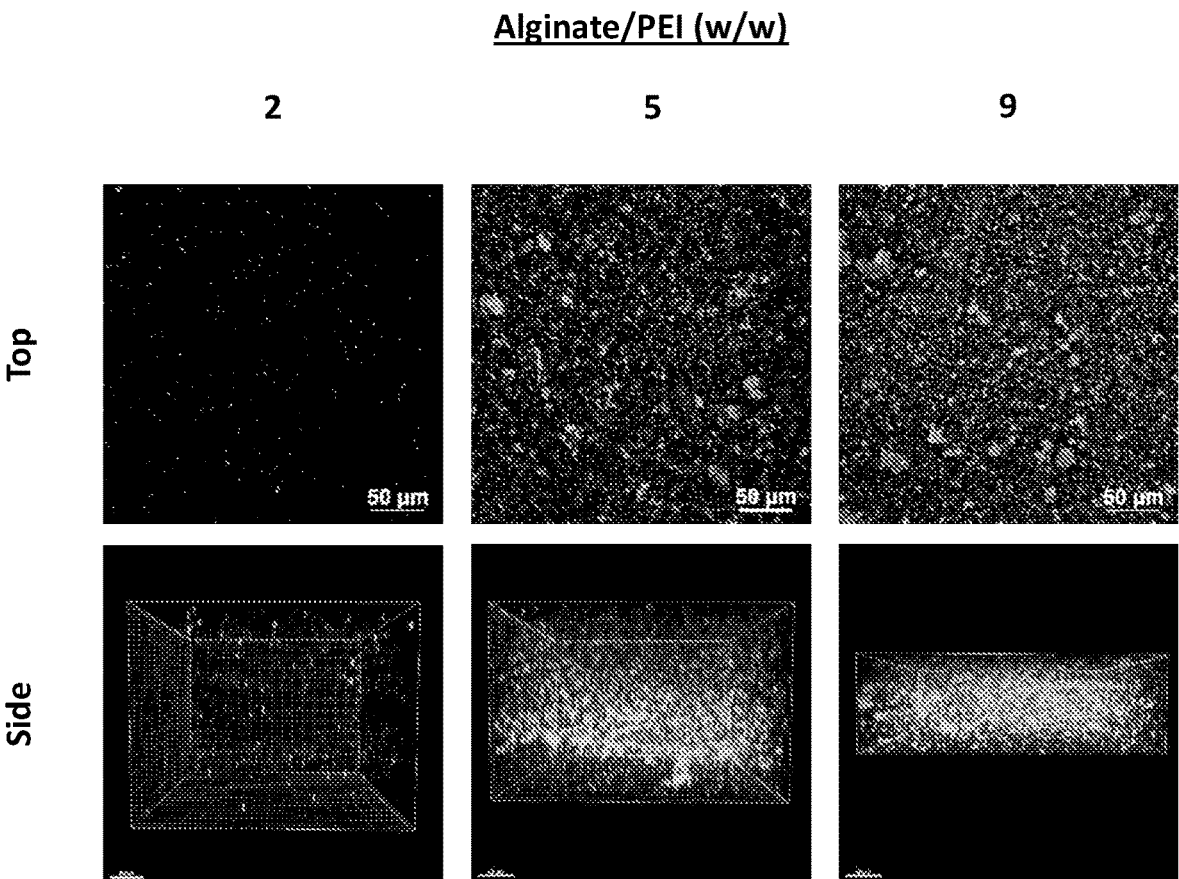
FIG. 12 shows alginate coating of lyophilized polyplexes with sucrose cryoprotection. Lyophilized polyplexes were loaded at 1 μg/μL gel. W/w ratios above 5 were able to give distributions similar to those from HA coating.

Lyophilized polyplexes coated with HA and cryoprotected with sucrose results in a lyophilized polyplex powder that can be incorporated inside hydrogels with no aggregation and retaining activity [FIG. 9]. For example, when hyaluronic acid-acrylamide backbone is mixed with the stabilized lyophilized polyplex powder and crosslinked with a dithiol containing peptide, the resulting gel contains polyplexes within its structure. The incorporation of lyophilized polyplexes does not interfere with the original scaffold properties, as confirmed by annealing the FLIP scaffold and performing rheology [FIG. 10]. The encapsulated polyplexes, by visual inspection using confocal microscopy, are non-aggregated and instead are uniformly dispersed within the bulk of the hydrogel [FIG. 11]. The formulation and coating process can be tailored to improve polyplex concentration within hydrogel precursor solution by balancing the sucrose cryoprotectant concentration. With a HA-NB coating at an N/P of 20 and HA/PEI ratio of 5, up to 5 μg polyplex per μL gel can be obtained by using 87.5 μg sucrose per μg polyplex. However, other natural polymers such as alginate can be used to coat lyophilized polyplexes and provide distributed nanoparticles within the hydrogel precursor solution [FIG. 12]

Figures 13A, 13B:
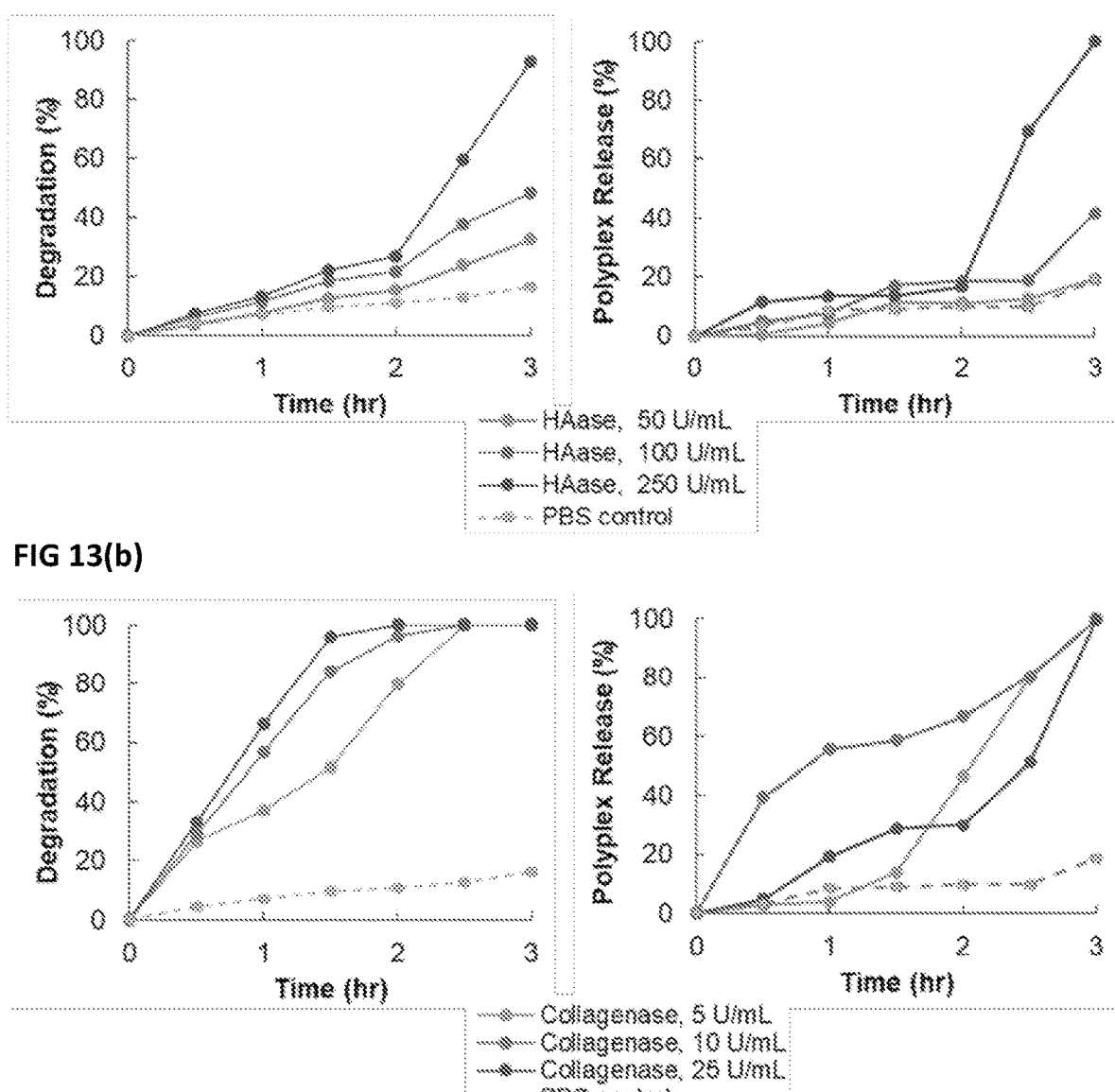
FIG. 13 shows polyplex retention and release by HA-Ac bulk hydrogels. P32-labeled DNA was used for lyophilized polyplex formation and loading into the hydrogel precursor, with scintillation to quantify the amount of DNA in buffer solution. Stained HA material was used to track the degradation of the gels under (FIG. 13A) hyaluronidase (HAase) and (FIG. 13B) Type IV collagenase (cleave the MMP crosslinker) at various concentrations to simulate degradative conditions when in cell culture. Relative to PBS, only degradative conditions resulted in the release of polyplexes into solution.
Figure 14A:
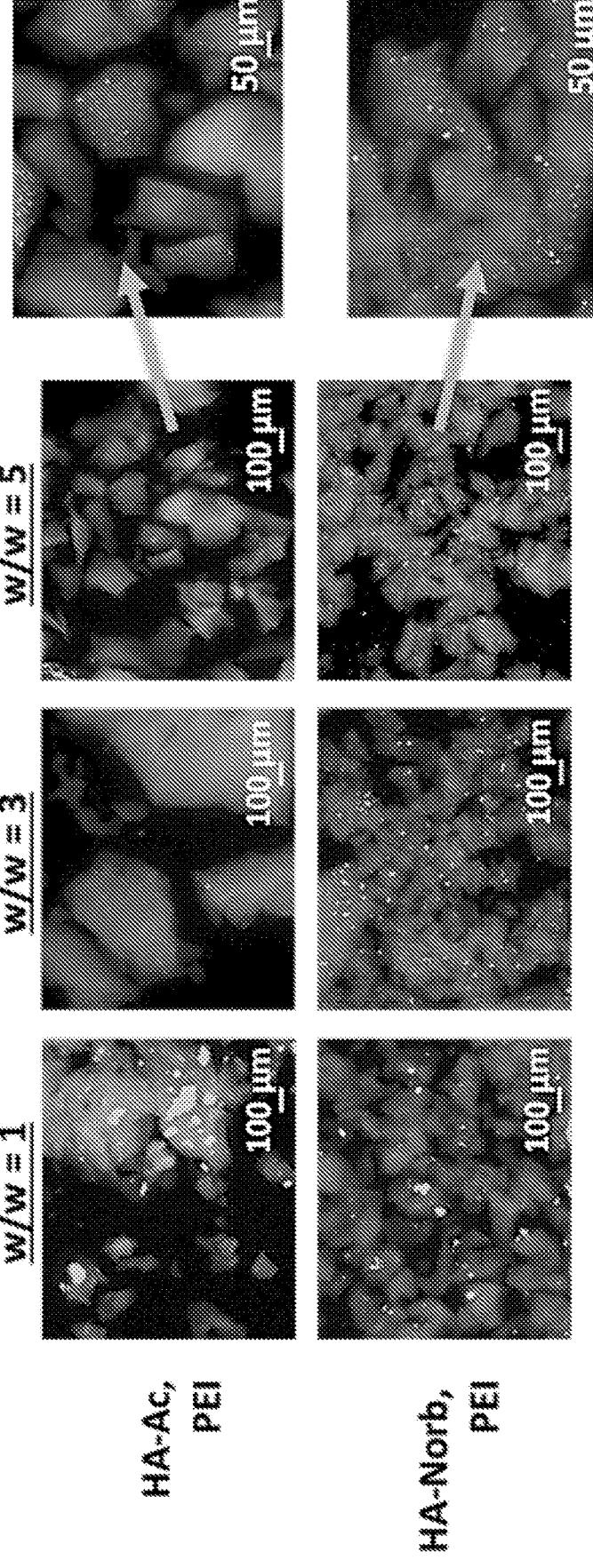
(FIG. 14A) Comparison of HA coating for HA-Ac and HA-NB and the HA/PEI coating ratio.
Figure 14B:
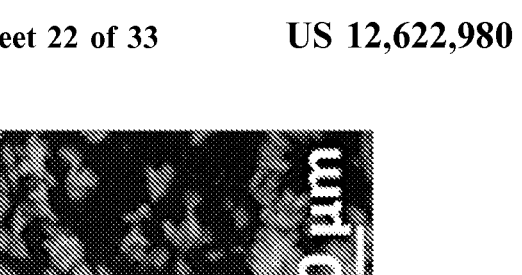
(FIG. 14B) Comparison of sieve size for producing microgels containing HA-NB coated polyplexes.
Figure 15A:
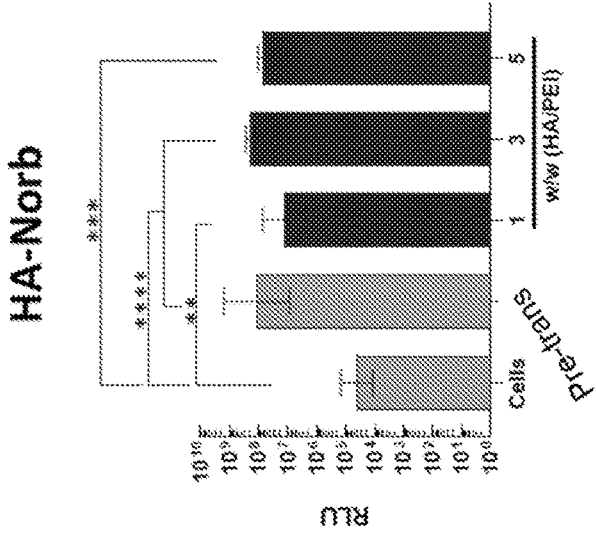
FIG. 15 shows Lyophilized coated polyplexes and FLIP transfection in mouse mesenchymal stem cells. "Cells" represents negative control background, while "pre-trans" (pre-transfected) are positive control, bolus transfected cells from fresh L-PEI polyplex that are seeded into the gels (the equivalent of cells being exposed to all of the polyplexes at once). The w/w HA/PEI represents different coating ratios by weight and are all samples that have been lyophilized and resuspended in the hydrogel HA-Ac precursor solution. n=3, with one-way ANOVA and Tukey's HSD (p<0.01). Unmodified HA and HA modified with norbornene groups (HA-Norb) achieved similar levels of transfection for all coating ratios, but HA-NB overall performed best. Unlike in 2D culture, HA-acrylate (HA-Ac) gave significantly worse transfection, in part due to the results from polyplex distribution within the gels and still some aggregation present across its conditions. Viability is also improved by the HA-NB coating, when compared to L-PEI pre-transfection from fresh polyplexes as a control.
Figure 15A:
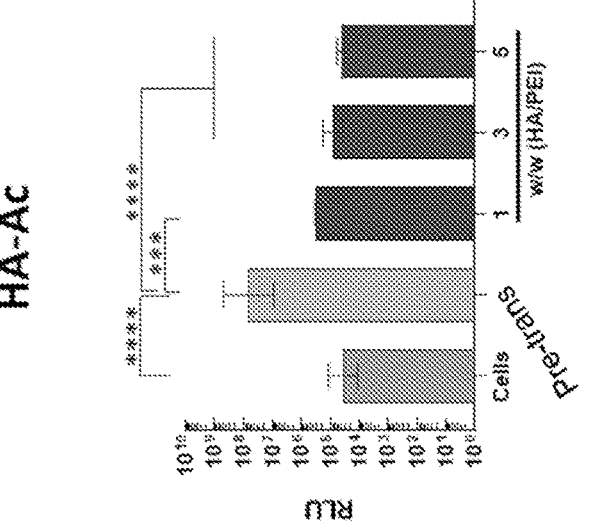
Figure 15A:
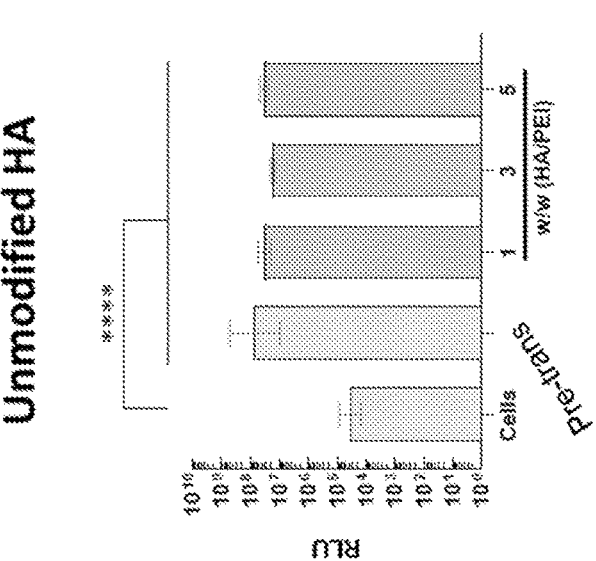
Figure 15B:
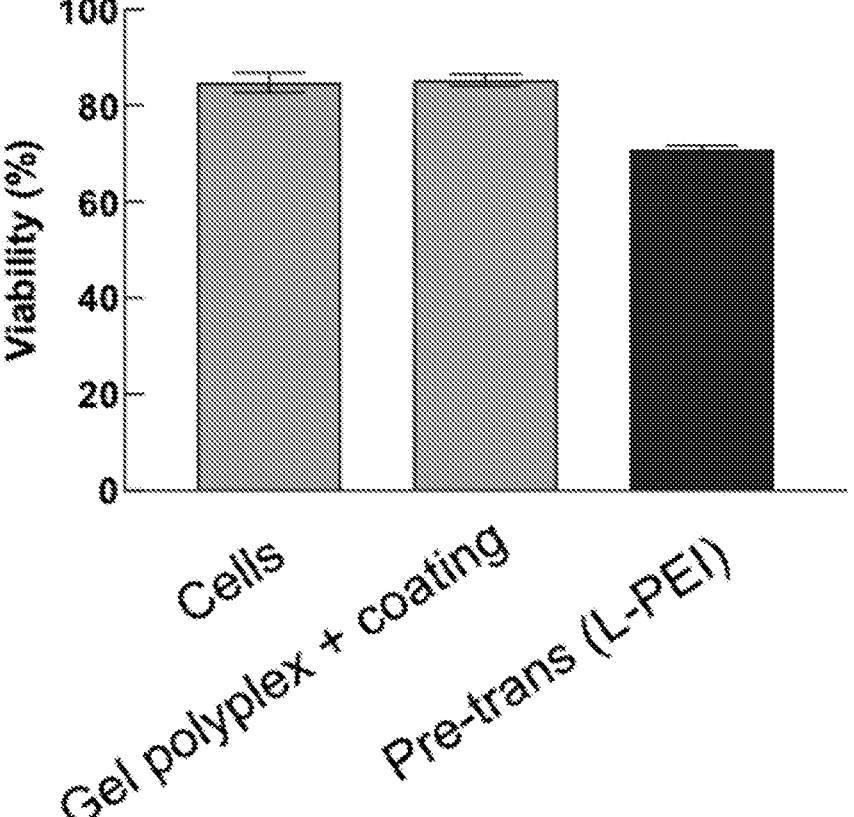

Because the mesh size of these hydrogels (1-100 nm) is smaller than the size of the polyplexes (100-400 nm), release of these polyplexes requires gel degradation to increase the mesh size [FIG. 13]. However, this also ensures that polyplexes are retained by the scaffold when sieve-converted from bulk hydrogel to shred hydrogel microparticles. Released polyplexes are able to effectively transfect cells with similar efficiency as fresh and lyophilized coated polyplexes. The nucleic acid loaded gel is stable for long term storage without loss of activity. The nucleic acid loaded gel can be further processed to generate irregularly shaped microgel particles, which can then be further processed to form a porous bulk hydrogel through annealing of the microgel particles, using the same method as for non-polyplex containing HA precursor solution. The resulting microgels contain polyplexes which are not altered by the microgel formation process [FIG. 14]. The mechanical properties and microstructure of nucleic acid loaded gels is similar to that of non-loaded gels. See FIG. 7.

Transfection of Nucleic Acid Loaded FLIPs

Figure 16A:
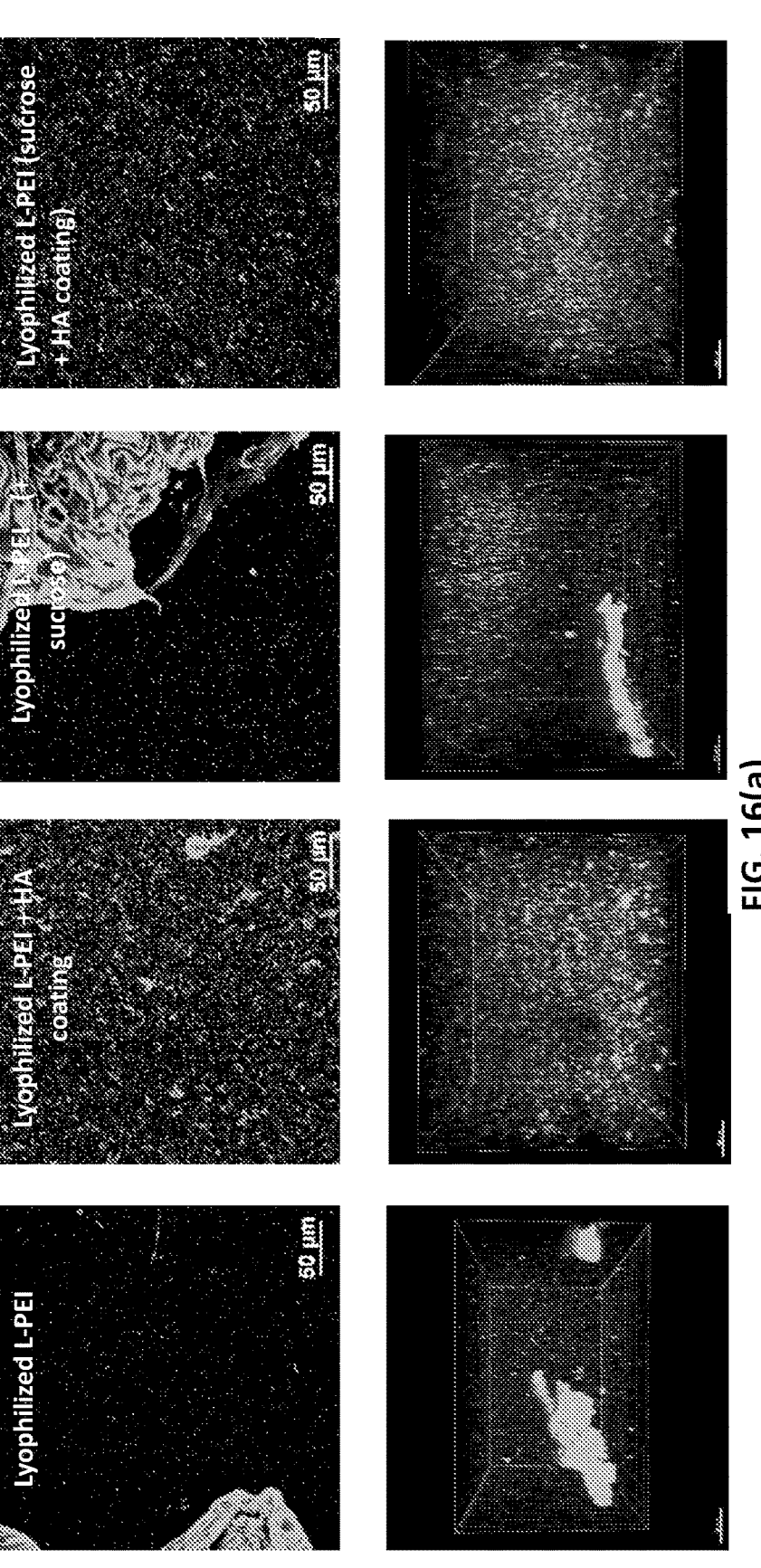
FIG. 16(A) Distribution of bulk HA-Ac hydrogels containing lyophilized polyplexes, with and without sucrose and HA coating.
Figure 16B:
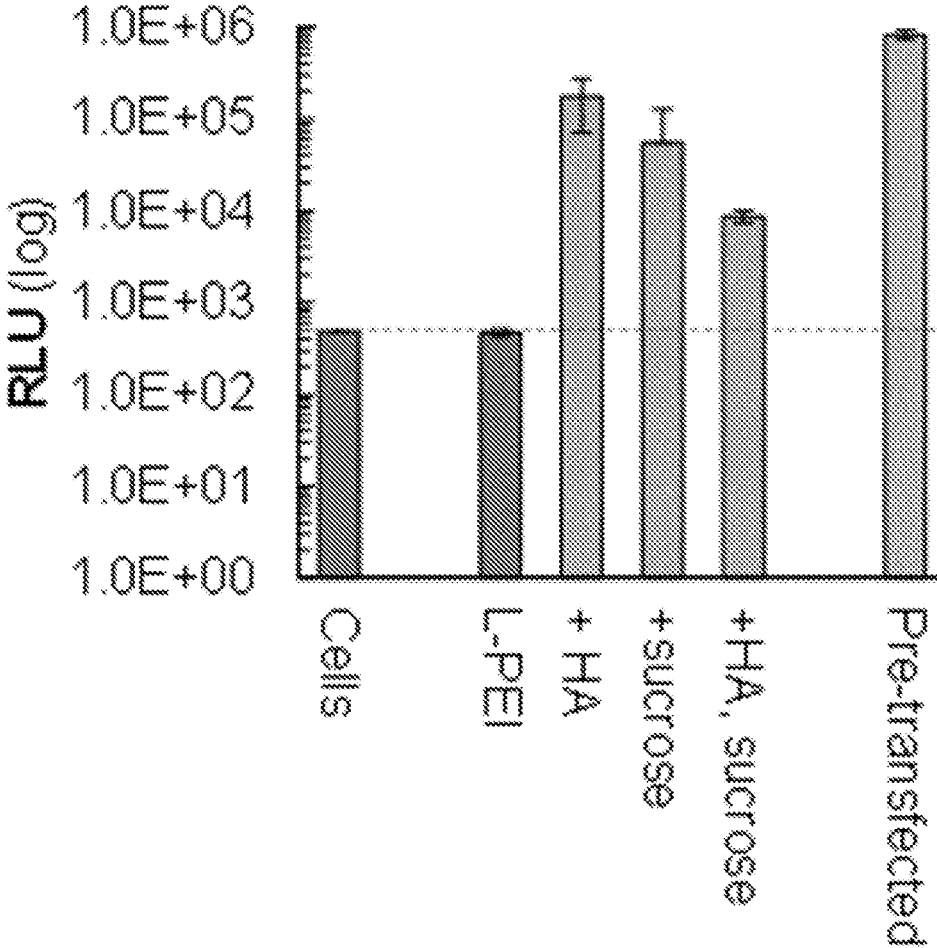
FIG. 16(B) Cells were seeded into scaffolds comprised of FLIP from the bulk gels. A bolus transfection control was seeded into a non-DNA containing FLIP scaffold, as for the cell control. L-PEI on its own was unable to transfect cells, with Gaussia luciferase expression not different from background. HA coating and sucrose cryoprotection was needed for adequate transfection relative to the control.

Cells seeded into nucleic acid loaded FLIP scaffolds become transfected with high viability demonstrating that entrapped nucleic acid material is non-toxic. The coating formulation for nucleic acids was optimized similarly as in 2D cell culture, balancing the N/P ratio of nucleic acid to complexing agent, and the weight ratio of complexing agent to HA coating [FIG. 15]. Of the coatings tested, HA-Ac, HA-Norb, and unmodified HA, the HA-Norb again gave the best improvement in transfection and viability in 3D culture, specifically at an HA/PEI ratio of 3-5 w/w. A final optimized formulation contains 87.5 μg sucrose per μg DNA, 5 w/w HA/PEI, and N/P of 20 with DNA loaded up to 5 μg DNA/μl of gel. It is possible to achieve significant transfection levels with the HA coating alone, compared to no transfection without either HA or sucrose, and little transfection observed with just sucrose as a cryoprotectants [FIG. 16].

The optimized coating formulation for lyophilized polyplexes is compatible with many nucleic acid vectors, including plasmid DNA and minicircle DNA [FIG. 20], which is preferred for its low immunogenicity and higher transfection ability in vitro and in vivo. In 2D cell culture, it is seen that the HA coating process is needed for improved lyophilized polyplex transfection and is helped by sucrose cryoprotection. For 3D culture, it is seen that FLIP scaffolds loaded with coated minicircle polyplexes are as good as bolus pre-transfected polyplexes, consistent with results for plasmid DNA but significantly higher in magnitude for transgene expression.

Figure 17:
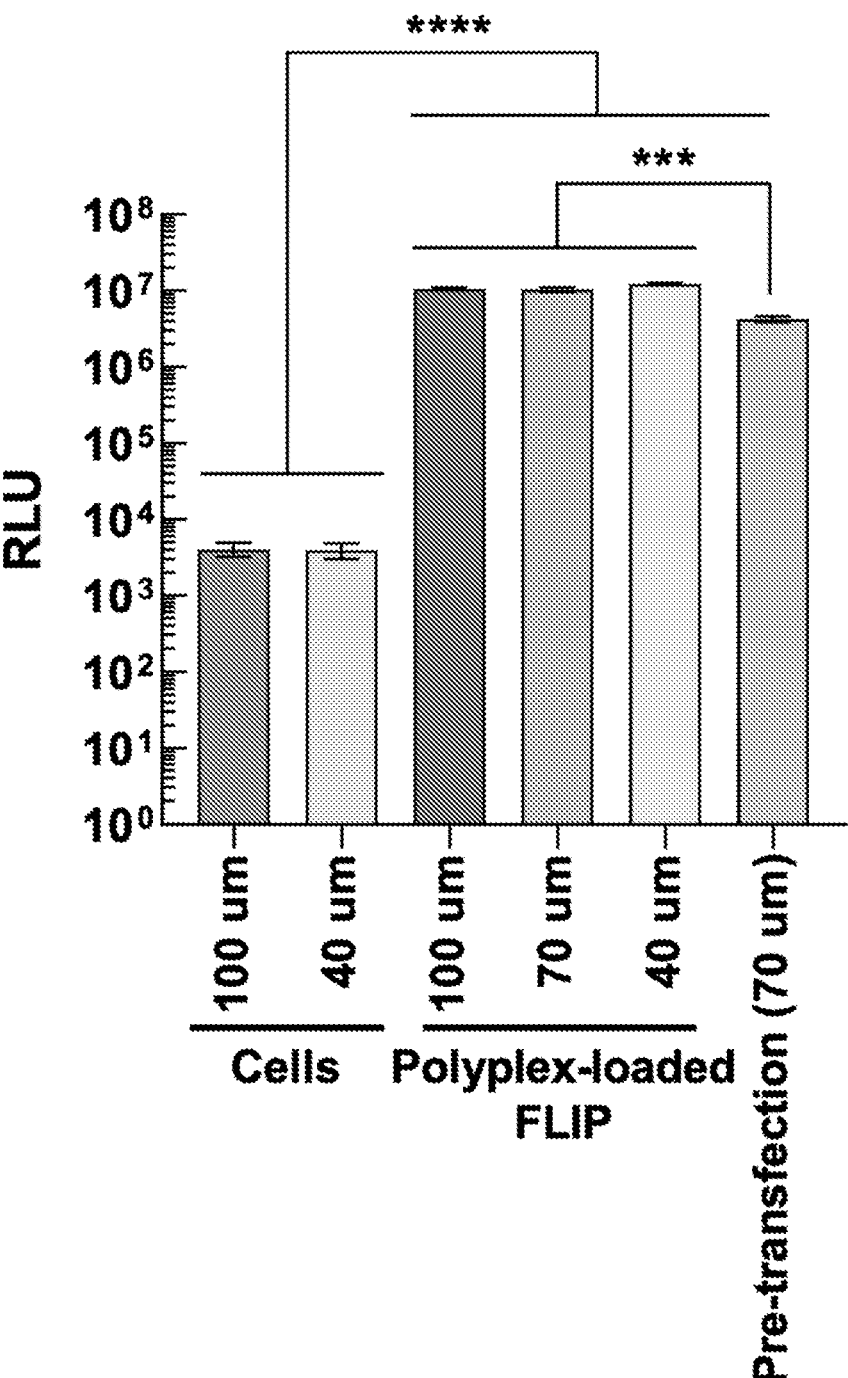
FIG. 17 shows Lyophilized coated polyplexes and FLIP transfection across different sieve sizes for generating microgels. Samples compared for n=3, with one-way ANOVA and Tukey's HSD (p<0.01).
Figure 18A:
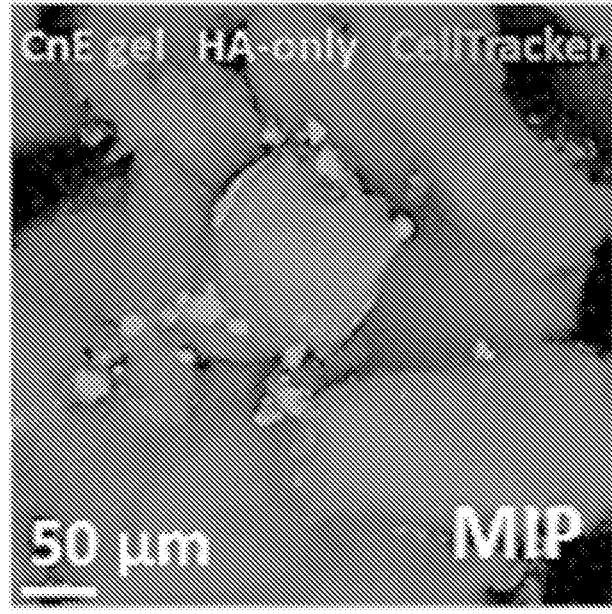
(FIG. 18A) Cell spreading within FLIP scaffolds comprised of two different precursor solutions, stained for 488 and 647, with cell membrane staining of live cells.
Figure 18A:
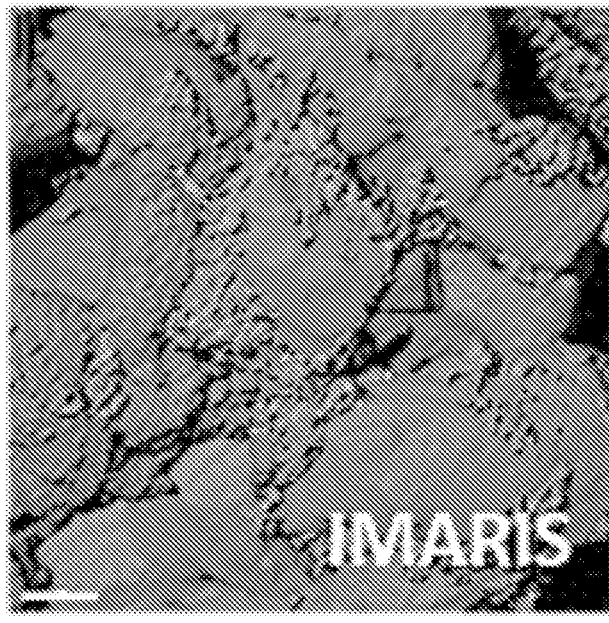
Figure 18B:
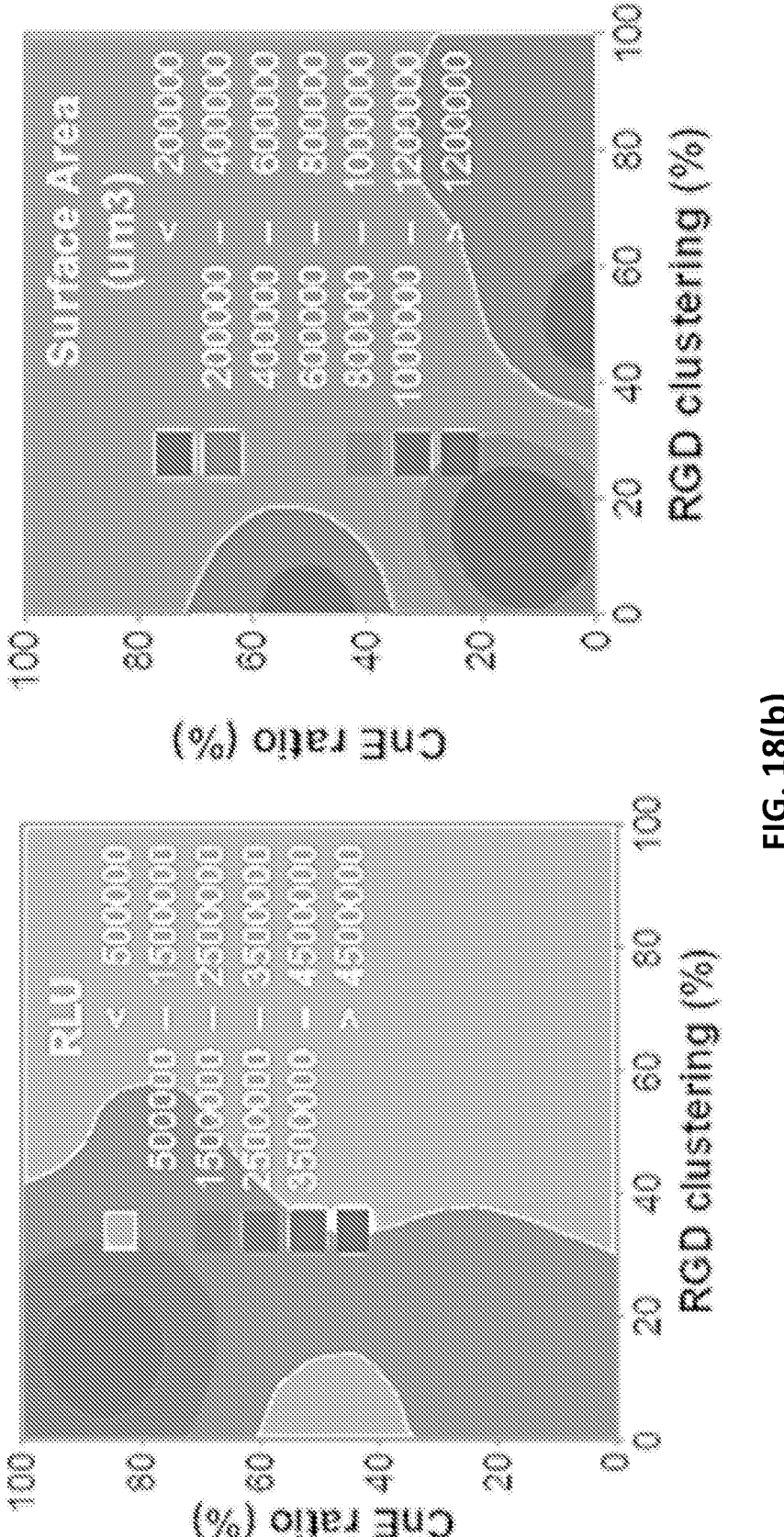
(FIG. 18B) DOE optimization of cell transfection and spreading (surface area) based on RGD peptide clustering on sHMP and ratio of lyophilized polyplexes-loaded to non-loaded sHMP within FLIP scaffolds. Transfection was assessed with Gaussia luciferase. An example of the transgene output is shown in (FIG. 18C) for a fixed 20% RGD clustering and was determined that 60-80% lyophilized polyplex content and 20% RGD clustering was the optimal balance between transfection and spreading/viability of cells.
Figure 18C:
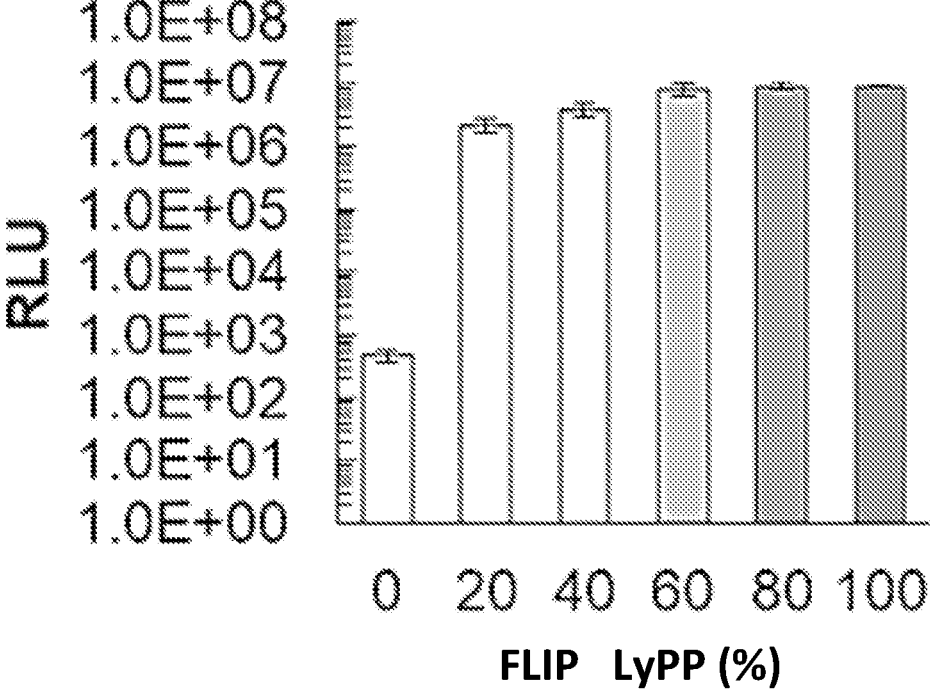
FIG. 18 shows Altering FLIP properties from sHMP modification for transfection and cell spreading.

FLIP scaffolds can be produced with different size particles (produced for example using sieves 40-100 μm). We have found that the size of the particle does not significantly impact the transfection efficiency achieved [FIG. 17].

The therapeutic polymer gel system can be further modified to modulate cellular behavior similar to other scaffolds for tissue engineering. The cell-material interaction is modulated by integrin binding. Peptides derived from extracellular matrix proteins or from peptide libraries have been identified and can mediate binding. FLIP material can be modified with peptides to modulate interactions with, e.g., integrins. For example, the peptide RGD. The amount and presentation of RGD peptide can be optimized to improve transfection, while maintaining cell viability. For example, keeping the concentration of RGD peptide at 1 mM but changing its distribution from homogenously distributed to clustered can affect both viability and gene transfer. Clustering was achieved by mixing RGD modified HA with unmodified HA. 100% modified RGD modified HA means homogenous, while 10% modified and 90% unmodified means 10% clustering. 0% refers to a gel without RGD. [FIG. 18].

In addition to physical parameters, FLIP also allows for the modulation of polyplex presentation. For example, mixing of nucleic acid loaded FLIP with unloaded FLIP results in a scaffold that has some particles loaded with nucleic acids, while some particles are not. This type of arrangement can result in enhanced viability while maintaining high transgene expression. [FIG. 18]

Figure 19A:
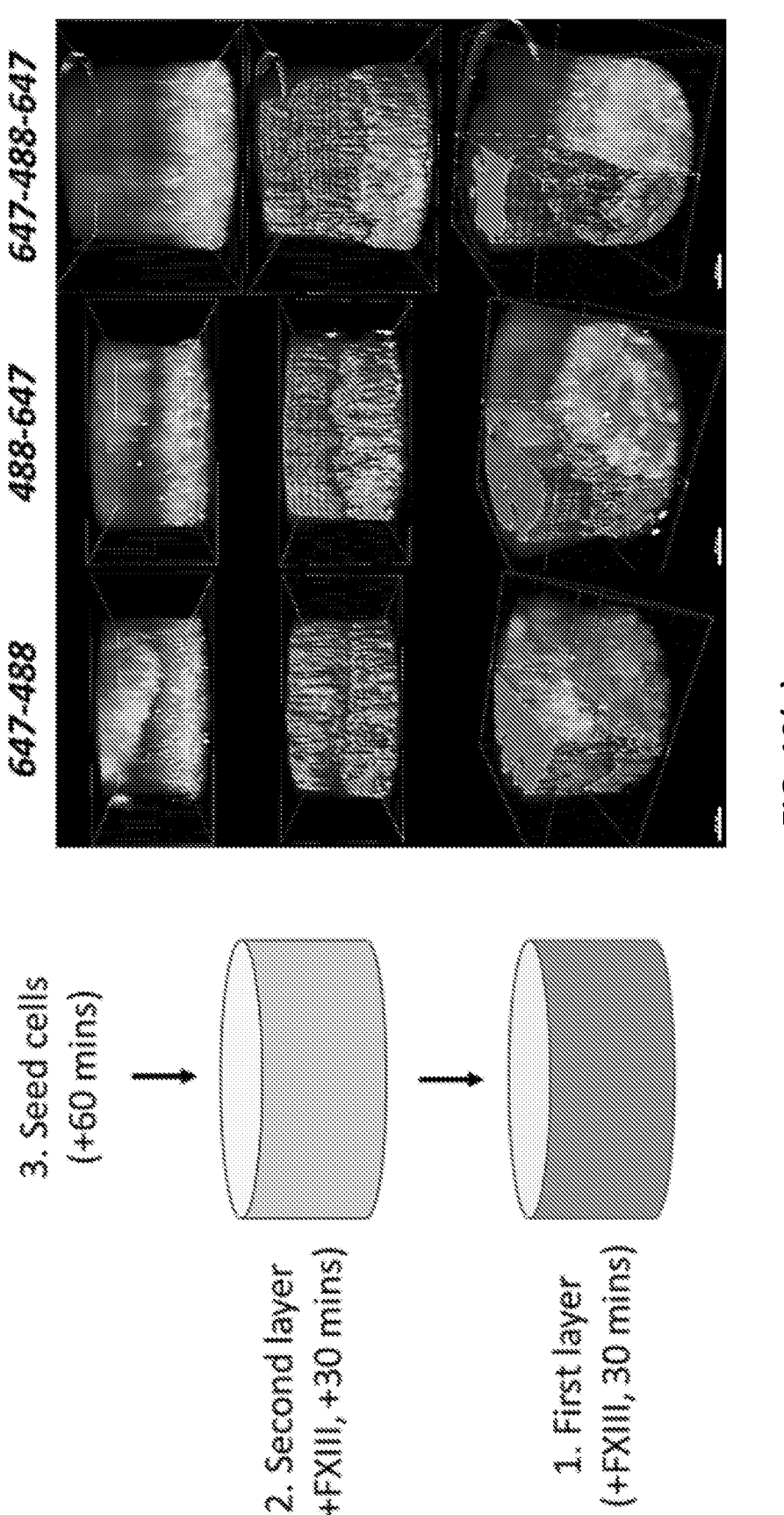
FIG. 19(A) shows FLIP gel layering based on sequencing syringe loading and injection into the 3D culture mold. Able to alternate layer of 488 or 647 stained gels without merging or loss of gels due to the annealing chemistry.
Figure 19B:
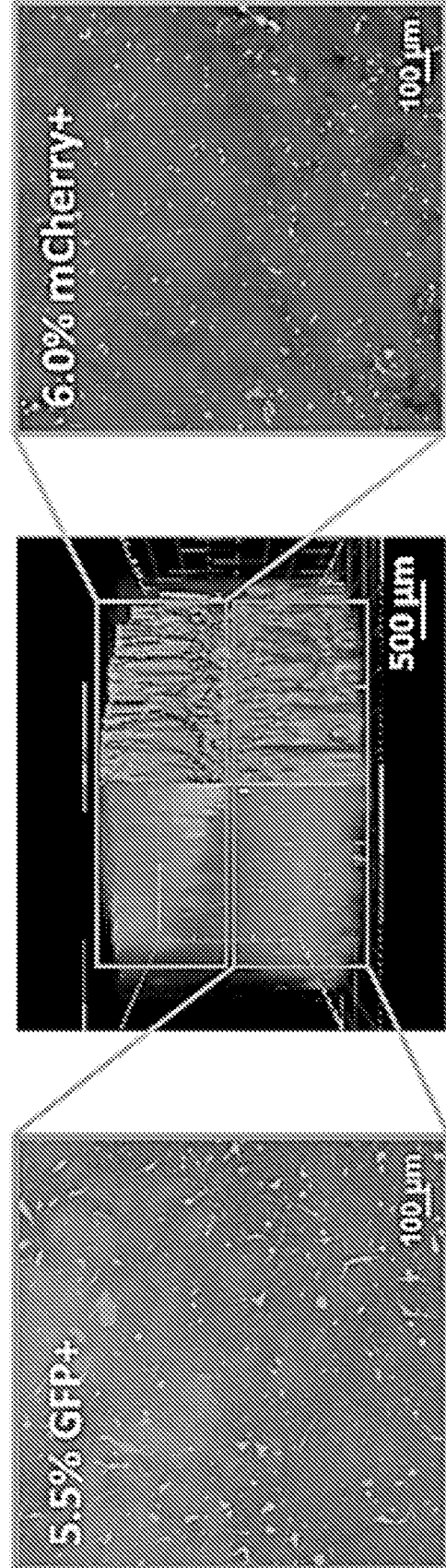
FIG. 19(B) Application of FLIP modification for "domain transfection,"

Alternatively, rather than mix a ratio of gels throughout the entire FLIP scaffold, fixed gel layers can be made to spatially order cell culture and direct function. Because of the granular nature of FLIP and the annealing chemistry, individual sHMP solutions can be loaded into a syringe and injected in order to create a layered 3D culture environment. This can also be accomplished by sequential addition of layers in a 3D culture device, which allows for very defined layers [FIG. 19]. Applying this to transfection, each gel layer can contain a specific transgene, such as two different reporter genes (GFP, mCherry), and allow for specific transfection of cells only within the layer, as supported from flow cytometry data. This is due to the local release of polyplexes as cells remodel the scaffold, which can be beneficial for spatially regulating gene expression in cell culture and in vivo.

Methods

MAP Hydrogels and Methods of Making

Preparation of Hyaluronic Acid-Acrylamide (HA-Ac)

To modify hyaluronic acid (HA) to contain acrylamide functional groups, 1 g of 70 kDa sodium hyaluronan (Contipro, 50-90 kDa) was dissolved in 200 mL DI water (1 g/200 mL). Adipic dihydrazide (ADH, Fisher Scientific) was added for a 1:40 molar ratio with HA, at 18.35 g, to add amines to the carboxylic acid side chains, and pH adjusted with 1 M HCl to 4.75 while stirring to dissolve. 2.02 g N-(3-Dimethylaminopropyl)-N'-ethylcarbodiimide hydrochloride (EDAC HCl, VWR) was added for a molar ratio of 1:4 for HA to EDC to activate the carboxylic acids. pH was maintained for 4 hours before allowing the reaction to proceed overnight at 25° C. with constant stirring. The reaction solution was then transferred to dialysis tubing (Fisherbrand, 6000-8000 Da), and dialyzed over 3 days in NaCl solutions of decreasing concentration, starting at 100 mM NaCl and ending with 24 hours of DI water. The final product was then filtered, flash-frozen, and lyophilized. The extent of ADH modification was confirmed via $^1$H-NMR spectrometry. The integrations of the peaks were normalized to the peak corresponding to the methyl group on the HA monomer at $\delta$=2.0 ppm to determine percent of HA monomers modified to contain ADH groups. After this, the HA-ADH was modified with 2.23 g N-Succinimidyl Acrylate (NHS-Ac, TCI Chemicals) for a molar ratio of 1:5 for HA to NHS-Ac. The HA-ADH was resuspended in 200 mL 10 mM HEPES (1 g/200 mL) with 150 mM NaCl, 10 mM EDTA, at pH 7.4. NHS-Ac was dissolved in DMSO (100 mg/mL) and added to the HA solution, lowering the pH to 6.0 and maintain for 4 hours while stirring before reacting overnight at 25° C. As before, the reaction solution was transferred to dialysis tubing and dialyzed over 3 days before the product was filtered, flash-frozen, and lyophilized. The extent of Ac modification was also confirmed via $^1$H-NMR spectrometry, normalizing to the HA peak.

Preparation of Hyaluronic Acid-Norbornene (HA-Norb)

To modify hyaluronic acid (HA) to contain norbornene functional groups, 1 g of 70 kDa sodium hyaluronan (Contipro, 50-90 kDa) and 3.111 g 4-(4,6-dimethoxy-1,3,5-triazin-2-yl)-4-methyl-morpholinium chloride (DMTMM) (Thermo Fisher Scientific, Waltham, MA) were each dissolved in 40 mL 200 mM MES buffer pH 5.5 (molar ratio of ~1:633 for HA to DMTMM). The two solutions were combined and stirred for 10 minutes to allow for activation of the carboxylic acid. 0.677 mL 5-norbornene-2-methylamine (TCI America, Portland, OR) was added dropwise to the reaction mixture (molar ratio of ~1:343 for activated HA to NMA), which was then allowed to react overnight at 25° C. with constant stirring. The reaction product was then precipitated in ethanol, filtered to collect the solid, dissolved in 2 M NaCl in water, and dialyzed under running deionized water for 24 hours. The final product was then filtered, flash-frozen, and lyophilized. The extent of modification was confirmed via $^1$H-NMR spectrometry. $^1$H-NMR shifts of attached norbornene groups in the product in $D_2O$ are $\delta$=6.33 and 6.02 (vinyl protons, endo), and 6.26 and 6.23 ppm (vinyl protons, exo). The integrations of these peaks were normalized to the peak corresponding to the methyl group on the HA monomer at $\delta$=2.0 ppm to determine percent of HA monomers modified to contain norbornene groups.

Vector Design and Generation (CRISPRa, Minicircle)

All plasmid vectors were based on the CMV promoter with polycistronic GFP-P2A-GLuc for GFP and Gaussia luciferase expression for in vitro studies. SV40 poly(A) tail and the Woodchuck Hepatitis Virus (WHP) Posttranscriptional Regulatory Element (WPRE) were used downstream the gene to enhance expression. Plasmids used for in vivo used Firefly luciferase (FLuc) in place of GLuc. In addition, pcDNA3.1(+)/Luc2=tdT was a gift from Christopher Contag (Addgene plasmid #32904), encoding for enhanced luciferase (Luc2) with a C-terminal fusion of tdTomato under the CMV promoter. For therapeutic gene vectors, either GLuc or GFP genes were replaced. Human VEGFa fragments VEGF165 (AF486837.1) or human IL-4 isoform 2 (NM 172348.3, GenScript) were inserted.

For studies with minicircles (MC), the CMV vectors with GLuc or FLuc were used, with the promoter and genes flanked by attP/attB recombinase sites for excising the bacterial elements via ZYCY10P3S2T E. coli (System Biosciences). MC production was induced with arabinose and cultured for 3 hours prior to plasmid prep. Purity was determined with agarose gel electrophoresis and AFM.

Polyplex Formation and HA Coating Assessment

DNA polyplexes were prepared by complexing plasmid DNA encoding for Gaussia luciferase (GLuc) and enhanced green fluorescent protein (eGFP) with linear polyethylen-imine (L-PEI, 25 kDa, Polyscience) at N/P ratios of 5, 7, 10, and 20. Briefly, 1 µg DNA was diluted in 10 µL of 150 mM NaCl and the corresponding amount of L-PEI was diluted in a separate tube in 10 µL of 150 mM NaCl. The L-PEI solution was then added to the DNA solution, immediately vortexed, and allowed to incubate for 15 min at 25° C. to allow for complexation. In the case of HA-coating, unmodi-fied HA (70 kDa), HA-Ac, or HA-Norb were added to the polyplex solution following incubation at w/w ratios (HA to PEI) of 2, 5, or 10, and then incubated another 15 min. Size and charge of the particles was assessed with dynamic light scattering (DLS) and electrophoretic light scattering (ELS) on a Malvern ZetaSizer ZS instrument, to determine if the polyplexes are prone to aggregation. Measurements were assessed in triplicate using the default run parameters, at up to 150 scans for ELS and 20 for DLS, for stabilized measurements to derive the zeta potential, hydrodynamic diameter, and polydispersity index (PDI). Trends were com-pared across all N/P and w/w ratios for each HA coating condition using contour modelling in Minitab

Lyophilized Polyplex Formulation and Bulk HA Gel Distribution

To load polyplexes into HA scaffolds, a method for polyplex lyophilization was developed. Instead of a low-melting point agarose and sucrose solution, only sucrose was used at concentrations from 45 to 350 µg sucrose/µg DNA. Polyplexes were prepared similar to before for up to 250 µg DNA, pre-mixed with sucrose and diluted 1:40 in nuclease-free water. No salt solution was used. Following L-PEI complexing and HA coating, polyplex solutions were flash-frozen and lyophilized.

To prepare bulk gels with and without lyophilized poly-plexes, 3.5 wt % HA-Ac gels were made with a matrix-metalloproteinase (MMP) dithiol crosslinker (Ac-GCRDGPQGIWGQDRCG-NH2, Genscript) (SEQ ID NO:01). HA-Ac was dissolved in 0.3 M triethanolamine (TeOA), pH 8.8. Crosslinker was prepared for a SH/HA monomer ratio of 19.00, dissolving in DI water. In the case of bulk gels containing lyophilized polyplexes, lyophilized polyplexes were resuspended in the volume of nuclease-free water for the crosslinker solution and used directly to resuspend the crosslinker. Both solutions were then com-bined and used to make 35 uL bulk gels by sandwiching with Sigmacoted glass slides using a 1 mm Teflon spacer, and then incubating at 37° C. for 60 mins. Following incubation, gels were transferred to 1×PBS solution containing Alexa-Flour 647-NHS (Thermo Fisher Scientific, 1:1000 dilution) to stain the HA using the residual ADH groups and YOYO-1 (Thermo Fisher Scientific, 1:10,000 dilution) to stain the polyplexes, swelling at 4° C. overnight.

Following swelling, gels were imaged using a confocal microscope (Nikon C2 scanning confocal) at 20× and 40× magnification across z-stacks (300-500 µm, at 25-50 slices) to visualize the polyplex distribution. Z-stacks were then assessed in IMARIS (Bitplane) to generate 3D renders of the distribution and assess aggregation.

sHMP-DNA Generation

From the bulk gels prepared with and without lyophilized polyplexes, shredded hydrogel microparticles (sHMP) with prepared by sieving the swelled gels stacked on a 70 µm cell sieve and washing with 1×PBS. The resulting flow-through was centrifuged at max speed to collect the particles and imaged on a fluorescent microscope (Zeiss Observer Z1) to determine if the lyophilized polyplex distribution was pre-served. Gel size distributions were quantified using binary converted images and area measurements in ImageJ.

For gels to be used in vitro with 3D culture, HA-Ac bulk gels were prepared similar to before, but the HA solution was modified with an RGD ligand (RGDSP, 1 mM) to improve cell adhesion and Q-peptide (Ac-NQEQVSPLG-GERCG-NH2, 0.75 mM) (SEQ ID NO:02) and K-peptide (Ac-FKGGERCG-NH2, 0.75 mM) (SEQ ID NO:03) for Factor XIII (FXIII)/Thrombin transamination annealing of the microparticles into FLIP scaffolds. Peptide modification was clustered by only reacting with 20% of the HA precursor for 15 mins at 25° C. before pooling back with the original solution.

Preparation of Cell Culturing Devices

A custom negative mold was printed using a 3D, Form 2 stereolithography printer (Formlabs, Inc.). Cell culture devices were cast using soft lithography to produce a PDMS reservoir for cell culture. The culture wells were composed of a cylindrical culture section (3 mm in diameter and 5 mm tall), enabling a maximum of 35 µL of volume. Additionally, a conical media reservoir above the cylindrical culturing section was able to contain up to 150 µL of media. Specific dimensions of the mold, and subsequently the PDMS wells. To fabricate PDMS culturing devices, 70 g of Sylgard 184 PDMS (Dow Corning) was preparing according to the manufacturer's instructions and poured into a 10 cm×10 cm square dish. The mold was placed in the PDMS, and the PDMS was degassed by applying a vacuum for 1 hour. Subsequently, the PDMS was allowed to cure at 60° C. for 4 hours in a convection oven. The PDMS slab was then cut into three-well pieces and plasma-bonded to cover glass slides using a corona plasma gun. PDMS triplicate well-slides were then autoclaved prior to use for cell culture and experimental evaluation.

Cell Culture and Seeding in FLIP Scaffolds

Human dermal fibroblasts (HDF) or D1 mouse mesen-chymal stem cells (Cell Applications, Inc., San Diego, CA) were maintained in culture in Dulbecco's modified Eagle's medium (Thermo Fisher Scientific) containing 10% fetal bovine serum (Thermo Fisher Scientific) at 37° C. and 5% $CO_2$. Human astrocytes were cultured using astrocyte growth media (Lonza), with all provided bullet kit supple-ments. Primary mouse neural precursor cells (NPCs) were cultured in DMEM containing 5% FBS (Hyclone), pituitary extract (13.6 µg/µL), EGF (0.1 µg/µL), bFGF (0.1 µg/µL) and N-2 formulation (100×, Gibco). Human umbilical vein cells (HUVECs) were cultured in endothelial cell media (Lonza) with bullet kit supplements except for VEGF. All media for cells contained 1% Penn/Step. Media was changed every 2-3 days. To seed cells in MAP scaffolds, 20 µL microgels were first equilibrated in supplemented media for 30 minutes before pelleting and removing supernatant. Cells were pre-stained with CellTracker Orange (Thermo Fisher Scientific), according to the manufacturer protocol, to allow for live monitoring of the cells as they spread in the annealed gels. Briefly, cells were stained with CellTracker at 10 µM and incubated 37° C. for 30 mins before replacing the media. Cells were trypsinized and $1.0×10^5$ cells/10 µL gel were pelleted by centrifugation at 250×g for 5 minutes. Media supernatant was aspirated and equilibrated microgels in FXIII and Thrombin (at 0.01 U/µL gel and 0.002 U/µL gel respectively) were then added to the cell pellet and mixed thoroughly by pipetting. Importantly, prior to gel/cell seeding, 6 μL of sterile 1% agarose in PBS was added to the wells to coat the glass surface and allowed to cool to 25° C. to prevent cell attachment to glass. 10 μL of gel plus cells was then pipetted into each well in the PDMS culturing device. The sHMP gel was allowed to anneal for 1 hour at 37° C. After annealing, the wells were filled with 150 μL supplemented media and incubated for 48 hours.

Void Space Analysis

Annealed sHMP scaffolds sizes were incubated with PBS containing 1 μg/mL 500 kDa tetramethylrhodamine isothiocyanate-dextran (TRITC-dextran) (Sigma-Aldrich, St. Louis, MO) to fill the void space in between microgels, as it is too large to penetrate the microgel polymer network. The labelled void space was imaged using Nikon Ti Eclipse equipped with C2 laser LED excitation to obtain 200-μm z-stacks. The z-stacks were imported into IMARIS to generate surface renders, and void space volumes were quantified as a fraction of the total volume represented by the z-stack. A minimum of 4 measurements were made for each MAP scaffold.

Oscillation Rheometry

Stiffness of both nonporous HA-Ac hydrogels and annealed FLIP scaffolds was measured as the storage modulus (G') using a plate-to-plate rheometer (Physica MCR, Anton Paar, Ashland, VA). A frequency sweep was performed on the hydrogels using a strain of 0.2% with an angular frequency range of 0.1 to 10 rad/s. To measure the storage modulus of an annealed MAP gel, 50 μL microgels with FXIII/Thrombin were pipetted directly onto the rheometer stage. The measuring position was set to 1 mm and the gel was allowed to incubate with humidity at 37° C. for 1 hour to allow for annealing. Once the gel was annealed, a frequency sweep was performed on the hydrogels using a strain of 1% with an angular frequency range of 0.1 to 10 rad/s.

3D Culture Imaging and Spreading Assessment

For improved imaging resolution and visualizing cell spreading, annealed gels with cells cultured for 2 days were fixed in 1% paraformaldehyde for 15 minutes at 25° C. The cultures were permeabilized in 0.1% Triton X-100 in PBS and stained using DAPI (Sigma-Aldrich) for cell nuclei and rhodamine phalloidin (Thermo Fisher) for cell actin per manufacturer's guidelines for 1 hour. Gels were washed with PBS before z-stack imaging with a Nikon confocal. To quantify cell spreading, the z-stacks were imported into IMARIS to generate surface renders of cell actin for surface area quantification and to count nuclei.

Transfection of MAP Gel Culture and Assay for Transgene Expression

Transfection was performed two days after seeding cells in MAP gels to allow for adequate spreading. For pre-transfected controls, DNA polyplexes were prepared as previously described for L-PEI conditions with and without HA coating 24-hours prior to 3D culture preparation. Amounts were scaled up depending on DNA dose and number of wells, but the polyplex volume administered to each well remained constant (20 μL of polyplexes were added to each well as a bolus administration). After 4 hours of polyplex exposure, the polyplex-containing media was removed and replenished with fresh media.

Transfection was quantified by measuring expression of GLuc 48 hours after 3D culture seeding, using the FLASH Gaussia Luciferase assay kit (NanoLight) per manufacturer's protocol. Conditioned media was collected from each well at each time point. Briefly, 20 μL of each sample was mixed with 50 μL of diluted substrate solution, pipetted for 2 to 3 seconds to mix, and read for luminescence with a 5 second integration time using a Tecan Spark plate reader.

Cells were also processed for flow cytometry (BD Accuri™ C6 Plus) quantification of transgene expression (GFP). Briefly, cells were extracted from gels using a digestion protocol (200 U/mL Type IV Collagenase, Hyaluronidase, 125 U/mL DNase I) in RPMI media (no serum). Following 30 minutes incubation and wash steps, cells were fixed for flow. Gating was based on 2D controls from trypsinized samples for live/dead cells and GFP expressing cells, and then control gated against gels without any cells. Samples were run for 20,000 cells based on gating.

Cell Viability

Cell viability was quantified using the PrestoBlue assay (Thermo Fisher Scientific) per manufacturer's instructions. 2D culture in 48 and 24 well plates was assessed with a 1:5 dilution of PrestoBlue in serum-containing media, followed by 2 hours incubation at 37° C. For 3D culture, the media in each well was replaced with a solution of 10 μL of the PrestoBlue reagent mixed with 90 μL of media and incubated for 3 hours. For both models, 90 μL from each well was transferred into a 96-well plate and absorbance was read at 570 nm, normalized to 600 nm, using the Tecan Spark plate reader. Viability (metabolic activity) was calculated using a blank control and cell-only control, normalized across the remaining sample conditions.

For 3D culture, cell viability was also assessed using LIVE/DEAD Viability/Cytotoxicity Kit (Thermo). Briefly, cells were stained at 0.5 μM Calcein AM (Live stain, 488 nm) and 2 uM Ethidium homodimer-1 (Dead stain, 555 nm) in sterile 1×PBS for 30 minutes at room temperature. Cells were washed in 1×PBS prior to imaging on a Nikon Ti Eclipse equipped with C2 laser LED excitation. Z-stacks were performed within 60 minutes of staining to reduce cell death and sample bias. Live and dead channels were assessed with IMARIS for relative quantification of cell population based on volume-filling.

Cells were also processed for flow cytometry (BD Accuri™ C6 Plus) quantification of viability. Briefly, cells were extracted from gels using a digestion protocol (200 U/mL Type IV Collagenase, Hyaluronidase, 125 U/mL DNase I) in RPMI media (no serum). Following 30 minutes incubation and wash steps, cells were stained with Propidium Iodide (PI) at 3 μM and incubating at room temperature for 15 minutes. Gating was based on 2D controls from trypsinized samples for live/dead cells and GFP expressing cells, and then control gated against gels without any cells. Samples were run for 20,000 cells based on gating.

Materials

Non-limiting examples of the materials used in the examples herein comprise, e.g., 70 kDa sodium hyaluronan (Contipro, 50-90 kDa); adipic dihydrazide (ADH, Fisher Scientific); N-(3-Dimethylaminopropyl)-N'-ethylcarbodiimide hydrochloride (EDAC HCl, VWR); dialysis tubing (Fisherbrand, 6000-8000 Da); N-Succinimidyl Acrylate (NHS-Ac, TCI Chemicals); 4-(4,6-dimethoxy-1,3,5-triazin-2-yl)-4-methyl-morpholinium chloride (DMTMM, Thermo Fisher Scientific); 5-norbornene-2-methylamine (TCI America); Ethanol, 200 proof (VWR—Decon Labs); Sodium chloride (NaCl, VWR); EDTA disodium salt dihydrate (Santa Cruz Biotechnology); triethanolamine (TeOA, Thomas Scientific—Alfa Aesar); linear polyethylinemine (L-PEI, 25 kDa, Polyscience); AlexaFlour 647-NHS (Thermo Fisher Scientific); ATTO488-NHS ester (Sigma-Aldrich); YOYO-1 (Thermo Fisher Scientific); and 10-beta *E. coli* (NEB).

All plasmids (DNA) and peptides are designed in-house, with the peptides produced by GenScript One skilled in the art will readily appreciate that the present disclosure is well adapted to carry out the objects and obtain the ends and advantages mentioned, as well as those inherent therein. The present disclosure described herein are presently representative of preferred embodiments, are exemplary, and are not intended as limitations on the scope of the present disclosure. Changes therein and other uses will occur to those skilled in the art which are encompassed within the spirit of the present disclosure as defined by the scope of the claims. In addition, the section headings used herein are for organizational purposes only and are not to be construed as limiting the subject matter described.

No admission is made that any reference, including any non-patent or patent document cited in this specification, constitutes prior art. In particular, it will be understood that, unless otherwise stated, reference to any document herein does not constitute an admission that any of these documents form part of the common general knowledge in the art in the United States or in any other country. Any discussion of the references states what their authors assert, and the applicant reserves the right to challenge the accuracy and pertinence of any of the documents cited herein. All references cited herein are fully incorporated by reference, unless explicitly indicated otherwise.

The present disclosure shall control in the event there are any disparities between any definitions and/or description found in the cited references.

We claim:

1. A scaffold comprising hydrogel particles,
   wherein the hydrogel particles comprise an irregular shape and comprise one or more polyplexes, and
   wherein the polyplexes comprise one or more copies of one or more nucleic acids and one or more nucleic acid complexing agents.

2. The scaffold of claim 1, wherein one or more hydrogel particles originate from a bulk hydrogel and one or more particles are discretely polymerized.

3. The scaffold of claim 2, wherein the polyplexes are substantially evenly distributed throughout the hydrogel particles that originate from a bulk hydrogel.

4. The scaffold of claim 1, wherein the irregularly shaped hydrogel particles comprise shred particles.

5. The scaffold of claim 1, wherein one or more hydrogel particles are devoid of nucleic acid and nucleic acid complexing agent (polyplexes), with the proviso that not all hydrogel particles are devoid of nucleic acid and nucleic acid complexing agent.

6. The scaffold of claim 4, wherein the hydrogel particles comprising an irregular shape comprises an average surface area of between about 100 $\mu m^2$ and 1000000 $\mu m^2$, or between about 500 $\mu m^2$ and 500000 $\mu m^2$, or between about 1000 $\mu m^2$ and 250000 $\mu m^2$, or between about 2500 $\mu m^2$ and 100000 $\mu m^2$, or between about 5000 $\mu m^2$ and 50000 $\mu m^2$, or between about 7500 $\mu m^2$ and 40000 $\mu m^2$, or between about 10000 $\mu m^2$ and 25000 $\mu m^2$.

7. The scaffold of claim 6, wherein two or more hydrogel particles are annealed together, and wherein annealed together comprises covalent, electrostatic, hydrophobic, mechanical and transamination annealing.

8. The scaffold of claim 1, wherein the nucleic acid complexing agent comprises a cationic polymer, cationic peptide, cationic lipid, or mixture thereof.

9. The scaffold of claim 1, wherein the nucleic acid and the nucleic acid complexing agent are mixed at a N/P ratio, and wherein the N/P ratio comprises between about 1 and 100, or between about 1 and 90, or between about 2 and 75, or between about 3 and 65, or between about 4 and 50.

10. The scaffold of claim 9, wherein when the nucleic acid is DNA and the complexing agent is PEI, the N/P ratio comprises between about 5 and 35, or between about 15 and 25, or about 20.

11. The scaffold of claim 1, wherein the polyplexes further comprise a coating layer, wherein the coating layer comprises one or more coating layer agents, and wherein the coating layer agents comprise one or more biocompatible polymers, one or more mineral salts, and mixtures thereof.

12. The scaffold of claim 1, wherein the nucleic acid comprises between about 0.1 mg/ml nucleic acid and 20 mg/ml nucleic acid, or between about 0.2 mg/ml nucleic acid and 18 mg/ml nucleic acid, or between about 0.25 mg/ml nucleic acid and 16 mg/ml nucleic acid, or between about 0.3 mg/ml nucleic acid and 14 mg/ml nucleic acid, or between about 0.4 mg/ml nucleic acid and 12 mg/ml nucleic acid, or between about 0.5 mg/ml nucleic acid and 10 mg/ml nucleic acid, or between about 0.5 mg/ml nucleic acid and 8 mg/ml nucleic acid, or between about 0.5 mg/ml nucleic acid and 7 mg/ml nucleic acid, or between about 0.5 mg/ml nucleic acid and 6 mg/ml nucleic acid, or between about 0.5 mg/ml nucleic acid and 5 mg/ml nucleic acid, or between about 0.6 mg/ml nucleic acid and 6 mg/ml nucleic acid, or between about 0.7 mg/ml nucleic acid and 7 mg/ml nucleic acid, or between about 0.8 mg/ml nucleic acid and 8 mg/ml nucleic acid, or between about 0.9 mg/ml nucleic acid and 9 mg/ml nucleic acid, or between about 1 mg/ml nucleic acid and 10 mg/ml nucleic acid, or between about 1 mg/ml nucleic acid and 7.5 mg/ml nucleic acid, or between about 1 mg/ml nucleic acid and 5 mg/ml nucleic acid.

13. A structure for localized and controlled release of nucleic acids, comprising:
   a scaffold comprising hydrogel particles, wherein the hydrogel particles comprise an irregular shape and comprise one or more polyplexes, and
   wherein the one or more polyplexes comprise one or more copies of one or more nucleic acids and one or more nucleic acid complexing agents;
   wherein the one or more nucleic acids is present at a total concentration of at least about 0.1 mg/ml, and
   further wherein the scaffold is characterized in that, when the structure is placed in contact with one or more cells so that the scaffold contacts the cells, the nucleic acid is released with a profile characterized by one or more of:
   a) a burst-free release;
   b) a sustained release; and
   c) exhibiting in vitro and/or in vivo biological effectiveness.

14. The structure of claim 13, wherein one or more hydrogel particles are devoid of nucleic acids and nucleic acid complexing agents, with the proviso that not all hydrogel particles are devoid of nucleic acid and nucleic acid complexing agent.

15. The structure of claim 13, wherein the concentration of the nucleic acid is at least about 0.1 mg/ml, about 0.2 mg/ml, about 0.3 mg/ml, about 0.4 mg/ml, about 0.5 mg/ml, about 0.6 mg/ml, about 0.7 mg/ml, about 0.8 mg/ml, about 0.9 mg/ml, about 1 mg/ml, about 1.5 mg/ml, about 2 mg/ml, about 2.5 mg/ml, about 3 mg/ml, about 3.5 mg/ml, about 4 mg/ml, about 4.5 mg/ml, about 5 mg/ml, about 5.5 mg/ml, about 6 mg/ml, about 6.5 mg/ml, about 7 mg/ml, about 7.5 mg/ml, about 8 mg/ml, about 8.5 mg/ml, about 9 mg/ml, about 9.5 mg/ml, about 10 mg/ml, about 11 mg/ml, about 12 mg/ml, about 13 mg/ml, about 14 mg/ml, about 15 mg/ml, about 16 mg/ml, about 17 mg/ml, about 18 mg/ml, about 19 mg/ml, about 20 mg/ml.

16. The structure of claim 13, wherein the burst-free release is characterized by releasing less than about 1%, about 2%, about 3%, about 4%, about 5%, about 10%, about 15%, about 20%, about 25%, about 30%, about 35%, about 40%, about 45% or about 50% of the nucleic acid agent in the first 24 hours after placement on the subject.

17. The structure of claim 13, wherein the burst-free release is characterized by the release of nucleic acids originating from only those particles in contact with the one or more cells.

18. The structure of claim 13, wherein the sustained release is characterized by the nucleic acid being released from the scaffold over an extended period of time of at least about 3 days, about 5 days, about 7 days, about 10 days, about 15 days, about 30 days, about 1 month, about 2 months, about 3 months, about 6 months, or about 1 year.

19. The structure of claim 13, wherein two or more hydrogel particles are annealed together, and wherein annealed together comprises covalent, electrostatic, hydrophobic, mechanical and transamination annealing.

20. The structure of claim 13, wherein the irregularly shaped hydrogel particles comprise shred particles.

* * * * *

SEQUENCE LISTING

```
<160> NUMBER OF SEQ ID NOS: 3

<210> SEQ ID NO 1
<211> LENGTH: 16
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: cross-linkable acrylamide group
<220> FEATURE:
<221> NAME/KEY: MOD_RES
<222> LOCATION: (16)..(16)
<223> OTHER INFORMATION: AMIDATION

<400> SEQUENCE: 1

Gly Cys Arg Asp Gly Pro Gln Gly Ile Trp Gly Gln Asp Arg Cys Gly
1               5                   10                  15

<210> SEQ ID NO 2
<211> LENGTH: 14
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: cross-linkable acrylaminde group
<220> FEATURE:
<221> NAME/KEY: MOD_RES
<222> LOCATION: (14)..(14)
<223> OTHER INFORMATION: AMIDATION

<400> SEQUENCE: 2

Asn Gln Glu Gln Val Ser Pro Leu Gly Gly Glu Arg Cys Gly
1               5                   10

<210> SEQ ID NO 3
<211> LENGTH: 8
<212> TYPE: PRT
<213> ORGANISM: Artificial Sequence
<220> FEATURE:
<223> OTHER INFORMATION: synthetic peptide
<220> FEATURE:
```

-continued

```
<221> NAME/KEY: MOD_RES
<222> LOCATION: (1)..(1)
<223> OTHER INFORMATION: cross-linkable acrylamide group
<220> FEATURE:
<221> NAME/KEY: MOD_RES
<222> LOCATION: (8)..(8)
<223> OTHER INFORMATION: AMIDATION

<400> SEQUENCE: 3

Phe Lys Gly Gly Glu Arg Cys Gly
1               5
```